(12) United States Patent  
Grumelard et al.

(10) Patent No.: US 9,764,169 B2
(45) Date of Patent: Sep. 19, 2017

(54) UV FILTER COMBINATIONS COMPRISING BENZYLIDENE MALONATES

(75) Inventors: Julie Grumelard, Huningue (FR); Thomas Ehlis, Freiburg (DE); Markus Hansch, Speyer (DE); Myriam Sohn, Saint-Louis (FR)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/381,965

(22) PCT Filed: Jun. 29, 2010

(86) PCT No.: PCT/EP2010/059181
§ 371 (c)(1),
(2), (4) Date: Jan. 31, 2012

(87) PCT Pub. No.: WO2011/003774
PCT Pub. Date: Jan. 13, 2011

(65) Prior Publication Data
US 2012/0128611 A1   May 24, 2012

(30) Foreign Application Priority Data
Jul. 7, 2009 (EP) ..................................... 09164739

(51) Int. Cl.
*A61Q 17/04* (2006.01)
*A61K 8/37* (2006.01)

(52) U.S. Cl.
CPC ............... *A61Q 17/04* (2013.01); *A61K 8/37* (2013.01)

(58) Field of Classification Search
CPC .................................. A61Q 17/04; A61K 8/37
(Continued)

(56) References Cited

U.S. PATENT DOCUMENTS 3,706,700 A   12/1972   Kirchmayr et al.
4,284,621 A * 8/1981   Preuss ....................... A61K 8/37
                                                       424/47
(Continued)

FOREIGN PATENT DOCUMENTS

EP   0278914 A2   8/1988
EP   0 848 947 A   6/1998
(Continued)

OTHER PUBLICATIONS

Hoshino et al., JP 9087234, Machine Translation.*
(Continued)

Primary Examiner — Yanzhi Zhang
(74) Attorney, Agent, or Firm — Marshall, Gerstein & Borun LLP

(57) ABSTRACT

Disclosed is the use of a UV filter combination, comprising (a) a first UV filter selected from benzylidene malonates of formula (1), wherein $R_1$ methyl; ethyl; propyl; or n-butyl; if $R_1$ is methyl, then R is tert. butyl; formula (II); formula (III); a radical of formula (1a); or a radical of formula (1b); wherein $R_2$ and $R_3$, independently from each other are hydrogen; or methyl; $R_4$ is methyl; ethyl; or n-propyl; $R_5$ and $R_6$ independently from each other are hydrogen; or $C_1$-$C_3$alkyl; if $R_1$ is ethyl; propyl; or n-butyl, then R is isopropyl; and (b) a second UV filter selected from ($b_1$) Bis-Ethylhexyloxyphenol Methoxyphenyl Triazine; ($b_2$) Butyl Methoxydibenzoylmethane; ($b_3$) Diethylhexyl Butamido Triazone; ($b_4$) Ethylhexyl Triazone; ($b_5$) Diethylamino Hydroxy Benzoyl Hexyl Benzoate; ($b_6$) Ethylhexyl Methoxycinnamate; ($b_7$) Ethylhexyl Salicylate; ($b_8$) Homosalate; ($b_9$) Octocrylene; ($b_{10}$) micronized Methylene Bis-Benzotriazolyl Tetramethylbutylphenol; ($b_{11}$) Phenylbenzimidazole Sulfonic Acid; ($b_{12}$) Titanium Dioxide; ($b_{13}$) micronized Tris-Biphenyl Triazine; and ($b_{14}$) micronized (2-{4-[2-(4-Diethylamino-2-hydroxy-benzoyl)-benzoyl]-piperazine-1-carbonyl}-phenyl)-(4-diethylamino-2-hydroxy-phenyl)-methanone;($b_{15}$) benzoicacid,4,4-[[3-[1,3,3,3-tetramethyl-1-[trimethylsilyl)oxy]-1-disiloxanyl]propyl]amino]-1,3,5-triazine-2,4-diyl]diimino]bis-, dibutyl ester wherein the UV filter combination comprises at least 2 UV filters of component ($b_1$)-($b_{14}$); for the protection of human and animal hair and skin against UV radiation.

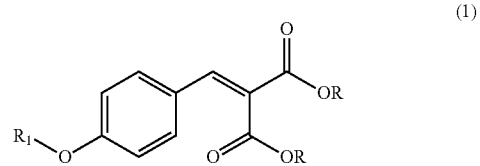

(1)

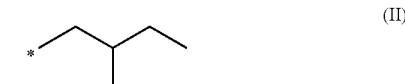

(II)

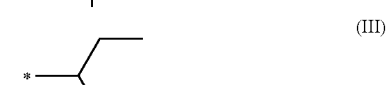

(III)

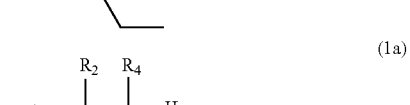

(1a)

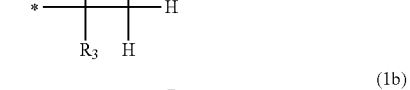

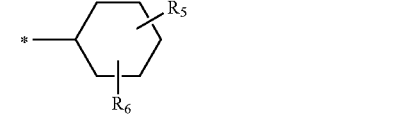

(1b)

13 Claims, No Drawings

(58) Field of Classification Search
USPC .................................................. 424/60, 59
See application file for complete search history.

(56) References Cited

U.S. PATENT DOCUMENTS

| | | | |
|---|---|---|---|
| 4,457,911 A | 7/1984 | Conner | |
| 4,749,774 A | 6/1988 | Weaver et al. | |
| 4,904,814 A | 2/1990 | Frei et al. | |
| 5,302,740 A | 4/1994 | Krutak et al. | |
| 5,624,663 A | 4/1997 | Deflandre et al. | |
| 5,670,140 A * | 9/1997 | Deflandre et al. | 424/59 |
| 5,882,634 A * | 3/1999 | Allard et al. | 424/59 |
| 7,354,571 B2 | 4/2008 | Richard | |
| 2010/0003207 A1* | 1/2010 | Candau et al. | 424/60 |
| 2011/0038815 A1 | 2/2011 | Hansch | |
| 2012/0128745 A1 | 5/2012 | Hansch et al. | |

FOREIGN PATENT DOCUMENTS

| | | | |
|---|---|---|---|
| EP | 1927343 A1 | | 6/2008 |
| FR | 2908988 A1 | | 5/2008 |
| JP | 09-087234 | | 3/1997 |
| JP | 9087234 | * | 3/1997 |
| JP | 2000136176 A | | 5/2000 |
| WO | WO 2010043588 | * | 4/2010 |
| WO | 2010/136360 A2 | | 12/2010 |

OTHER PUBLICATIONS

English Language Abstract of FR 2 908 988 May 30, 2008.
PAJ 09-087234 Mar. 31, 1997.
English Language Abstract of JP 2000/136176 May 16, 2000.
Bhatt et al., J. Inst. Chemists (India) XLVII, 1975 pp. 21-24.

* cited by examiner

UV FILTER COMBINATIONS COMPRISING BENZYLIDENE MALONATES

The present invention relates to the use of specific UV filter combinations comprising benzylidene malonates for cosmetic preparations.

It is well known that ultraviolet radiation (light) is harmful to human skin. Depending on the wavelength UV radiation causes different types of skin damage. UV-B radiation (about 290 to about 320 nm) is responsible for sunburn and can cause skin cancer. UV-A radiation (about 320 to about 400 nm) while producing tanning of the skin, contributes also to sunburn and the induction of skin cancers. Moreover, the harmful effects of the UV-B radiation may be aggravated by UV-A radiation.

Therefore, an effective sunscreen formulation preferably comprises both at least one UV-A and UV-B filter and a broad band UV filter covering the full range from about 290 nm to about 40 nm to prevent the human skin from the damage of sunlight.

Besides their screening power on solar radiation UV filters must also have good resistance to water and perspiration and also satisfactory photostability.

Unfortunately, many effective organic UV filters have a poor oil-solubility at a certain concentration and tend to crystallization. As a consequence the UV protection efficacy is significantly decreased.

It is known that there are lipophilic UV filters like Butyl Methoxydibenzoylmethane (sold under the tradename "Parsol 1789" by DSM) which have the particularity and also the disadvantage of being solid at ambient temperature. As a result, their use in sunscreen cosmetic compositions implies certain constraints in terms of their formulation and their use, in particular the selection of specific suitable cosmetic solvents that afford a proper solubility of these UV filters. Thus, a UV filter should show high solubility in common cosmetic oils or should be a good solvent for other UV filters that show poor oil solubility.

Moreover the oil soluble UV filters should be included in cosmetic sun care products without any impact on the sensorial characteristic of the emulsion. For that reason the optimal distribution of the UV absorber within the hydrolipid film left on the skin after spreading should be guaranteed.

It is therefore an object of the present invention to find UV absorber formulations which have improved properties regarding the UV absorber.

Surprisingly it has been found that specific monomeric benzylidene malonates have very good properties as cosmetic UV-B absorbers.

Therefore, the present invention relates to the use of a UV filter combination, comprising (a) a first UV filter selected from benzylidene malonates of formula

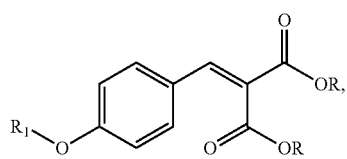

(1)

wherein
$R_1$ methyl; ethyl; propyl; or n-butyl;
if $R_1$ is methyl, then
R is tert. butyl;

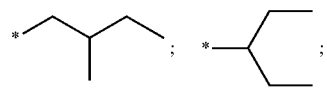

a radical of formula

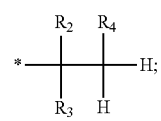

(1a)

or a or a radical of formula

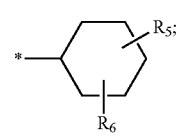

(1b)

wherein
$R_2$ and $R_3$, independently from each other are hydrogen; or methyl;
$R_4$ is methyl; ethyl; or n-propyl;
$R_5$ and $R_6$ independently from each other are hydrogen; or $C_1$-$C_3$alkyl;
if $R_1$ is ethyl; propyl; or n-butyl, then
R is isopropyl; and (b) a second UV filter selected from
($b_1$) Bis-Ethylhexyloxyphenol Methoxyphenyl Triazine;
($b_2$) Butyl Methoxydibenzoylmethane;
($b_3$) Diethylhexyl Butamido Triazone;
($b_4$) Ethylhexyl Triazone;
($b_5$) Diethylamino Hydroxy Benzoyl Hexyl Benzoate;
($b_6$) Ethylhexyl Methoxycinnamate;
($b_7$) Ethylhexyl Salicylate;
($b_8$) Homosalate;
($b_9$) Octocrylene;
($b_{10}$) micronized Methylene Bis-Benzotriazolyl Tetramethylbutylphenol;
($b_{11}$) Phenylbenzimidazole Sulfonic Acid;
($b_{12}$) Titanium Dioxide;
($b_{13}$) micronized Tris-Biphenyl Triazine; and
($b_{14}$) micronized (2-{4-[2-(4-Diethylamino-2-hydroxy-benzoyl)-benzoyl]-piperazine-1-carbonyl}-phenyl)-(4-diethylamino-2-hydroxy-phenyl)-methanone;
($b_{15}$) benzoic acid,4,4'-[[3-[1,3,3,3-tetramethyl-1-[trimethylsilyl)oxy]-1-disiloxanyl]-propyl]amino]-1,3,5-triazine-2,4-diyl]diimino]bis-, dibutyl ester (Bis(butyl-benzoate) diaminotriazine aminopropylsiloxane; BBDAPT); CAS Regno. 207562-42-3 corresponding to the formula wherein the UV filter combination comprises at least 2 UV filters of component $(b_1)$-$(b_{15})$; for the protection of human and animal hair and skin against UV radiation.

Prefereably, in formula (1)

R is a radical of formula and $R_1$ is methyl.

Most preferred are compounds of formula (1), wherein in formula (1a) at least one of $R_2$ or $R_3$ is methyl.

Most preferred are also compounds of formula (1), wherein in formula (1a) $R_2$ and $R_3$ are methyl.

Preferred are also compounds, wherein $R_1$ is ethyl; propyl; or n-butyl; and

R is isopropyl.

Examples of compounds of formula (1) are listed in the Table 1 below:

TABLE 1

Examples of monomeric benzylidene malonates according to the present invention

| | $R_1$ | R |
|---|---|---|
| MBM-01 | methyl | tert-butyl |
| MBM-02 | methyl | n-propyl |
| MBM-03 | methyl | n-pentyl |
| MBM-04 | methyl | n-hexyl |
| MBM-05 | methyl | sec-pentyl |
| MBM-06 | methyl | isobutyl |
| MBM-07 | methyl | isopentyl |
| MBM-08 | methyl | tert-pentyl |
| MBM-09 | methyl | isopropyl-methyl |
| MBM-10 | ethyl | isopropyl |
| MBM-11 | propyl | isopropyl |
| MBM-12 | n-butyl | isopropyl |
| MBM-13 | methyl | 2-ethylhexyl branched |

Preferably the present UV filter combination comprises two of components $(b_1)$-$(b_{15})$.

Preferably the UV filter combinations comprise
(a) a first UV filter selected from a benzylidene malonate of formula (1) as defined in claim 1;
(b) a second UV filter ($b_1$) Bis-Ethylhexyloxyphenol Methoxyphenyl Triazine; and
(c) a third UV-filter ($b_5$) Diethylamino Hydroxy Benzoyl Hexyl Benzoate or ($b_2$) Butyl Methoxydibenzoylmethane.

Preferred are also UV filter combinations comprising
(a) a first UV filter selected from a benzylidene malonate of formula (1) as defined in claim 1;
(b) a second UV filter ($b_{10}$) micronized Methylene Bis-Benzotriazolyl Tetramethylbutylphenol; and
(c) a third UV-filter ($b_1$) Bis-Ethylhexyloxyphenol Methoxyphenyl Triazine or ($b_5$) Diethylamino Hydroxy Benzoyl Hexyl Benzoate or ($b_2$) Butyl Methoxydibenzoylmethane.

Preferred are also UV filter combinations comprising
(a) a first UV filter selected from a benzylidene malonate of formula (1) as defined in claim 1;
(b) a second UV filter ($b_5$) Diethylamino Hydroxy Benzoyl Hexyl Benzoate; and
(c) a third UV-filter ($b_2$) Butyl Methoxydibenzoylmethane.

Preferred are also UV filter combinations comprising
(a) a first UV filter selected from a benzylidene malonate of formula (1) as defined in claim 1;
(b) a second UV filter ($b_4$) Ethylhexyl Triazone and/or ($b_{15}$) benzoic acid,4,4'-[[3-[1,3,3,3-tetramethyl-1-[trimethylsilyl)oxy]-1-disiloxanyl]propyl]amino]-1,3,5-triazine-2,4-diyl]diimino]bis-, dibutyl ester; and
(c) a third UV-filter ($b_{10}$) micronized Methylene Bis-Benzotriazolyl Tetramethylbutylphenol or ($b_1$) Bis-Ethylhexyloxyphenol Methoxyphenyl Triazine or ($b_5$) Diethylamino Hydroxy Benzoyl Hexyl Benzoate or ($b_2$) Butyl Methoxydibenzoylmethane.

Preferred are also UV filter combinations comprising
(a) a first UV filter selected from a benzylidene malonate of formula (1) as defined in claim 1;
(b) a second UV filter ($b_{15}$) Bis(butylbenzoate) diaminotriazine aminopropylsiloxane; and
(c) a third UV-filter ($b_{10}$) micronized Methylene Bis-Benzotriazolyl Tetramethylbutylphenol or ($b_1$) Bis-Ethylhexyloxyphenol Methoxyphenyl Triazine or ($b_5$) Diethylamino Hydroxy Benzoyl Hexyl Benzoate or ($b_2$) Butyl Methoxydibenzoylmethane.

Preferred are also UV filter combinations comprising three of components ($b_1$)-($b_{15}$).

Preferred are UV filter combinations comprising
(a) a first UV filter selected from a benzylidene malonate of formula (1) as defined in claim 1;
(b) a second UV filter ($b_{10}$) micronized Methylene Bis-Benzotriazolyl Tetramethylbutylphenol;
(c) a third UV filter ($b_1$) Bis-Ethylhexyloxyphenol Methoxyphenyl Triazine or ($b_5$) Diethylamino Hydroxy Benzoyl Hexyl Benzoate or ($b_2$) Butyl Methoxydibenzoylmethane; and
(d) a fourth UV filter ($b_4$) Ethylhexyl Triazone.

Preferred are UV filter combinations comprising
(a) a first UV filter selected from a benzylidene malonate of formula (1) as defined in claim 1;
(b) a second UV filter ($b_{10}$) micronized Methylene Bis-Benzotriazolyl Tetramethylbutylphenol;
(c) a third UV filter ($b_1$) Bis-Ethylhexyloxyphenol Methoxyphenyl Triazine or ($b_5$) Diethylamino Hydroxy Benzoyl Hexyl Benzoate or ($b_2$) Butyl Methoxydibenzoylmethane; and
(d) a fourth UV filter ($b_{15}$) Bis(butylbenzoate) diaminotriazine aminopropylsiloxane.

Preferred are also UV filter combinations comprising
(a) a first UV filter selected from a benzylidene malonate of formula (1) as defined in claim 1;
(b) a second UV filter ($b_1$) Bis-Ethylhexyloxyphenol Methoxyphenyl Triazine;
(c) a third UV filter ($b_5$) Diethylamino Hydroxy Benzoyl Hexyl Benzoate or ($b_2$) Butyl Methoxydibenzoylmethane; and
(d) a fourth UV filter ($b_4$) Ethylhexyl Triazone.

Preferred are also UV filter combinations comprising
(a) a first UV filter selected from a benzylidene malonate of formula (1) as defined in claim 1;
(b) a second UV filter ($b_1$) Bis-Ethylhexyloxyphenol Methoxyphenyl Triazine;
(c) a third UV filter ($b_5$) Diethylamino Hydroxy Benzoyl Hexyl Benzoate or ($b_2$) Butyl Methoxydibenzoylmethane; and
(d) a fourth UV filter ($b_{15}$) Bis(butylbenzoate) diaminotriazine aminopropylsiloxane.

Preferred are also UV filter combination comprising
(a) a first UV filter selected from a benzylidene malonate of formula (1) as defined in claim 1;
(b) a second UV filter ($b_5$) Diethylamino Hydroxy Benzoyl Hexyl Benzoate;
(c) a third UV filter ($b_2$) Butyl Methoxydibenzoylmethane; and
(d) a fourth UV filter ($b_4$) Ethylhexyl Triazone.

Preferred are also UV filter combination comprising
(a) a first UV filter selected from a benzylidene malonate of formula (1) as defined in claim 1;
(b) a second UV filter ($b_5$) Diethylamino Hydroxy Benzoyl Hexyl Benzoate;
(c) a third UV filter ($b_2$) Butyl Methoxydibenzoylmethane; and
(d) a fourth UV filter ($b_4$) Bis(butylbenzoate) diaminotriazine aminopropylsiloxane.

Preferred are also UV filter combinations comprising four or more than four of components ($b_1$)-($b_{14}$).

Preferred are UV filter combination comprising
(a) a first UV filter selected from a benzylidene malonate of formula (1) as defined in claim 1;
(b) a second UV filter ($b_1$) Bis-Ethylhexyloxyphenol Methoxyphenyl Triazine;
(c) a third filter ($b_{10}$) micronized Methylene Bis-Benzotriazolyl Tetramethylbutylphenyl or ($b_5$) Diethylamino Hydroxy Benzoyl Hexyl Benzoate or ($b_2$) Butyl Methoxydibenzoylmethane;
(d) a fourth filter ($b_4$) Ethylhexyl Triazone; and
(e) further filters ($b_7$) Ethylhexyl Salicylate and/or ($b_{13}$) micronized Tris-Biphenyl Triazine and/or ($b_9$) Octocrylene and/or ($b_3$) Diethylhexyl Butamido Triazone and/or ($b_{11}$) Phenylbenzimidazole Sulfonic Acid and/or ($b_{12}$) Titanium Dioxide and/or ($b_8$) Homosalate and/or micronized (2-{4-[2-(4-Diethylamino-2-hydroxy-benzoyl)-benzoyl]-piperazine-1-carbonyl}-phenyl)-(4-diethylamino-2-hydroxy-phenyl)-methanone and/or ($b_{15}$) Bis(butylbenzoate) diaminotriazine aminopropylsiloxane; and (a) a first UV filter selected from a benzylidene malonate of formula (1) as defined in claim 1;
(b) a second UV filter ($b_1$) Bis-Ethylhexyloxyphenol Methoxyphenyl Triazine;
(c) a third filter ($b_{10}$) micronized Methylene Bis-Benzotriazolyl Tetramethylbutylphenyl or ($b_5$) Diethylamino Hydroxy Benzoyl Hexyl Benzoate or ($b_2$) Butyl Methoxydibenzoylmethane;
(d) a fourth filter ($b_{15}$) Bis(butylbenzoate) diaminotriazine aminopropylsiloxane; and (e) further filters (b$_7$) Ethylhexyl Salicylate and/or (b$_{13}$) micronized Tris-Biphenyl Triazine and/or (b$_9$) Octocrylene and/or (b$_3$) Diethylhexyl Butamido Triazone and/or (b$_{11}$) Phenylbenzimidazole Sulfonic Acid and/or (b$_{12}$) Titanium Dioxide and/or (b$_8$%) Homosalate and/or micronized (2-{4-[2-(4-Diethylamino-2-hydroxy-benzoyl)-benzoyl]-piperazine-1-carbonyl}-phenyl)-(4-diethylamino-2-hydroxy-phenyl)-methanone.

Preferred are also UV filter combinations comprising (a) a first UV filter selected from a benzylidene malonate of formula (1) as defined in claim 1;

(b) a second UV filter (b$_{10}$) micronized Methylene Bis-Benzotriazolyl Tetramethylbutylphenol;

(c) a third filter (b$_5$) Diethylamino Hydroxy Benzoyl Hexyl Benzoate or (b$_2$) Butyl Methoxydibenzoylmethane;

(d) a fourth filter (b$_4$) Ethylhexyl Triazone and/or (b$_{15}$) benzoic acid,4,4'-[[3-[1,3,3,3-tetramethyl-1-[trimethylsilyl)oxy]-1-disiloxanyl]propyl]amino]-1,3,5-triazine-2,4-diyl]diimino]bis-, dibutyl ester; and (e) further filters (b$_7$) Ethylhexyl Salicylate and/or (b$_{13}$) micronized Tris-Biphenyl Triazine and/or (b$_9$) Octocrylene and/or (b$_3$) Diethylhexyl Butamido Triazone and/or (b$_{11}$) Phenyl-benzimidazole Sulfonic Acid and/or (b$_{12}$) Titanium Dioxide and/or (b$_8$) Homosalate and/or micronized (2-{4-[2-(4-Diethylamino-2-hydroxy-benzoyl)-benzoyl]-piperazine-1-carbonyl}-phenyl)-(4-diethylamino-2-hydroxy-phenyl)-methanone, and (a) a first UV filter selected from a benzylidene malonate of formula (1) as defined in claim 1, (b) a second UV filter (b$_{10}$) micronized Methylene Bis-Benzotriazolyl Tetramethylbutylphenol;

(c) a third filter (b$_5$) Diethylamino Hydroxy Benzoyl Hexyl Benzoate or (b$_2$) Butyl Methoxydibenzoylmethane;

(d) a fourth filter (b$_{15}$) Bis(butylbenzoate) diaminotriazine aminopropylsiloxane; and (e) further filters (b$_7$) Ethylhexyl Salicylate and/or (b$_{13}$) micronized Tris-Biphenyl Triazine and/or (b$_9$) Octocrylene and/or (b$_3$) Diethylhexyl Butamido Triazone and/or (b$_{11}$) Phenylbenzimidazole Sulfonic Acid and/or (b$_{12}$) Titanium Dioxide and/or (b$_8$) Homosalate and/or micronized (2-{4-[2-(4-Diethylamino-2-hydroxy-benzoyl)-benzoyl]-piperazine-1-carbonyl}-phenyl)-(4-diethylamino-2-hydroxy-phenyl)-methanone and/or BEMT (Tinosorb S, Bis-Ethylhexyloxyphenol Methoxyphenyl Triazine) encapsulated in a polymer matrix, as described in IP.com Journal (2009), 9(1B), 17 (Tinosorb S aqua, BASF)

In Table 2 the preferred UV filter combinations according to the present invention are summarized:

TABLE 2 preferred UV filter combinations according to the present invention

| | | UV filter Component (a) | UV filter Component (b$_1$)-(b$_{15}$) | | | |
|---|---|---|---|---|---|---|
| | | 1 | 2 | 3 | 4 | ≥5 |
| Combination of 3 UV filters | 1 | MBM | MBBT | BEMT DHHB BMBM | | |
| | 2 | MBM | BEMT | DHHB BMBM | | |
| | 3 | MBM | DHHB | BMBM | | |
| | 4 | MBM | EHT BBDAPT | MBBT BEMT DHHB BMBM | | |

TABLE 2-continued preferred UV filter combinations according to the present invention

| | | UV filter Component (a) | UV filter Component (b$_1$)-(b$_{15}$) | | | |
|---|---|---|---|---|---|---|
| | | 1 | 2 | 3 | 4 | ≥5 |
| Combination of 4 UV filters | 5 | MBM | MBBT | BEMT DHHB BMBM | EHT BBDAPT | |
| | 6 | MBM | BEMT | DHHB BMBM | EHT BBDAPT | |
| | 7 | MBM | DHHB | BMBM | EHT BBDAPT | |
| Combination of ≥5 UV filters | 8 | MBM | BEMT | MBBT DHHB BMBM | EHT | EHS TBT OCR DBT PBSA TiO$_2$ HMS DHHM BBDAPT |
| | 9 | MBM | MBBT | DHHB BMBM | EHT BBDAPT | EHS TBT OCR DBT PBSA TiO$_2$ HMS DHHM |
| | 10 | MBM | MBBT | DHHB BMBM | BBDAPT | EHS TBT OCR DBT PBSA TiO$_2$ HMS DHHM BEMT* |

MBM MONOMERIC Benzylidene Malonate
BEMT Bis-Ethylhexyloxyphenol Methoxyphenyl Triazine
BMBM Butyl Methoxydibenzoylmethane
DBT Diethylhexyl Butamido Triazone
EHT Ethylhexyl Triazone
BBDAPT Bis(butylbenzoate) diaminotriazine aminopropylsiloxane
DHHB Diethylamino Hydroxy Benzoyl Hexyl Benzoate
EHS Ethylhexyl Salicylate
HMS Homosalate
OCR Octocrylene
MBBT Micronized Methylene Bis-Benzotriazolyl Tetramethylbutylphenol
PBSA Phenylbenzimidazole Sulfonic Acid
TiO$_2$ Titanium Dioxide
TBT Micronized Tris-Biphenyl Triazine
DHHM Micronized (2-{4-[2-(4-Diethylamino-2-hydroxy-benzoyl)-benzoyl]-piperazine-1-carbonyl}-phenyl)-(4-diethylamino-2-hydroxy-phenyl)-methanone
BEMT* Tinosorb S, Bis-Ethylhexyloxyphenol Methoxyphenyl Triazine) encapsulated in a polymer matrix, as described in IP.com Journal (2009), 9(1B), 17 (Tinosorb S aqua, BASF)

The present invention also refers to novel monomeric benzylidene compounds. These compounds correspond to formula

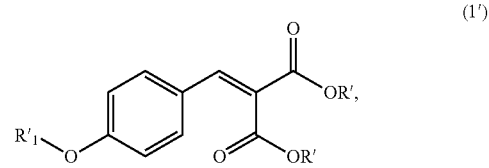

wherein
R'$_1$ methyl; ethyl; propyl; or n-butyl;
if R'$_1$ is methyl, then
R' is tert. butyl; or a radical of formula

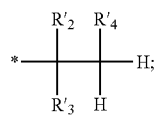 (1'a)

or a radical of formula

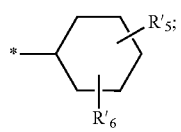 (1'b)

wherein
R'$_2$ and R'$_3$, independently from each other are hydrogen; or methyl;
R'$_4$ is methyl; ethyl; or n-propyl;
if R'$_1$ is ethyl; or propyl; then
R' is isopropyl.

Preferred are benzylidene malonates according of formula (1'), wherein R'$_1$ is methyl.

Most preferred are benzylidene malonates according of formula (1'), wherein R'$_2$ and R'$_3$ are methyl.

Even more preferred are benzylidene malonates according of formula (1'), wherein R' is a radical of formula

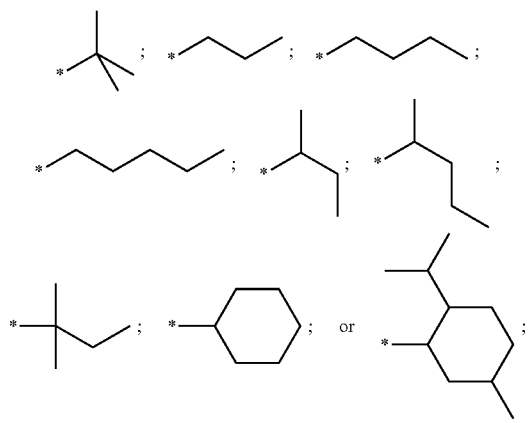

and
R'$_1$ is methyl.

Preferred are also benzylidene malonates of formula (1'), wherein
R'$_1$ is ethyl, ethyl; propyl; or n-butyl; and
R' is isopropyl.

The benzylidene malonates according to the present invention are prepared in a manner known per se according to the following reaction scheme:

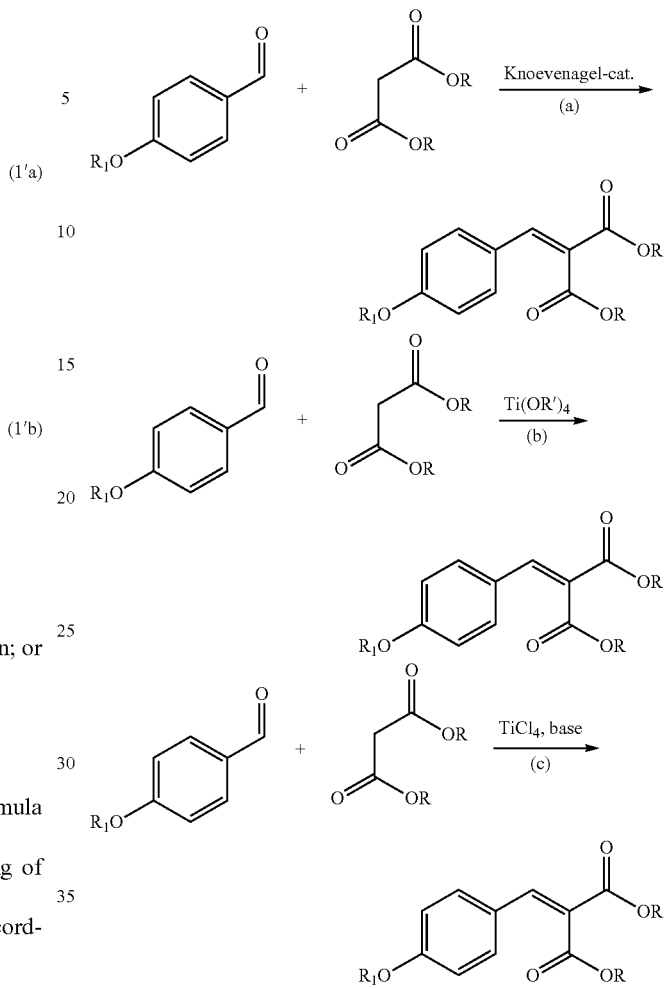

The Knoevenagel condensation under conditions (a) is carried out under azeotropic removal of water in the presence of a catalyst (literature: Jones, Gurnos. Knoevenagel condensation. Organic Reactions (New York) 15, 204-599 (1967).

Solvents used in this step are for example benzene, toluene, o-xylene, m-xylene, p-xylene, chloroform, dichloromethane, ethanol, methanol, tetrahydrofurane, acetonitrile, ethyl acetate, CCl$_4$, cyclohexane, n-hexane, n-pentane, or ionic liquids as for example 1-methyl-3-butyl imidazolium bromide. Mixtures of solvents can also be used.

The reaction temperature is preferably between 0° C. and the reflux temperature of the solvent mixture, preferably between 0° C. and 180° C., and more preferably between 20° and 150° C. The reaction time is preferably from 5 min to 72 h, and more preferably from 1 to 10 h.

The catalysts used in this reaction step are preferably primary, secondary or tertiary amines like piperidine, n-hexylamine, pyridine or triethylamine. The basic amines can be used as such or in combination with an acidic compound like acetic acid, benzoic acid or HCl. Suitable catalysts are any catalysts which are normally used in Knoevenagel reactions. Preferably are used catalysts such as a salt of an organic base with an organic acid, such as piperidinium acetate.

The Knoevenagel condensation under conditions (b) is carried out in the presence of a tetraalkyl orthotitanate Ti(OR') (0.5 req. to 5 eq. with respect to the aldehyde) as described for example in K. Yamashita et al., *Tetrahedron* 2005, 61, 7981-7985. Solvents used in this step are alcohols R'OH, for example ethanol, methanol, isopropanol, n-propanol, n-butanol, 2-methyl-1-butanol, isobutanol, 2-butanol, 2-pentanol. Other suitable solvents are benzene, toluene, o-xylene, m-xylene, p-xylene, chloroform, dichloromethane, tetrahydrofurane, acetonitrile, ethyl acetate, $CCl_4$, cyclohexane, n-hexane, n-pentane, or ionic liquids as for example 1-methyl-3-butyl imidazolium bromide. Mixtures of solvents can also be used. The reaction temperature is preferably between −10° C. and the reflux temperature of the solvent mixture, preferably between 0° C. and 180° C., and more preferably between 20° and 150° C.

The Knoevenagel condensation under conditions (c) is carried out in the presence of a titanium tetrachloride $TiCl_4$ (0.5 req. to 5 eq. with respect to the aldehyde) as described for example in W. Lehnert, *Tetrahedron Letters* 1970, 54, 4723-4724 or in H. Chen et al., *Eur. J. Org. Chem.* 2006, 2329-2335. Solvents used in this step are ethers like tetrahydrofurane, dioxane, tert-butyl-methylether, diethyl ether, or alcohols R'OH, for example ethanol, methanol, isopropanol, n-propanol, n-butanol, 2-methyl-1-butanol, isobutanol, 2-butanol, 2-pentanol. Other suitable solvents are benzene, toluene, o-xylene, m-xylene, p-xylene, chloroform, dichloromethane, tetrahydrofurane, acetonitrile, ethyl acetate, $CCl_4$, cyclohexane, n-hexane, n-pentane, or ionic liquids as for example 1-methyl-3-butyl imidazolium bromide. Mixtures of solvents can also be used.

The reaction temperature is preferably between −10° C. and the reflux temperature of the solvent mixture, preferably between 0° C. and 180° C., and more preferably between 20° and 150° C.

The UV filter combination according to the present invention is especially useful for the protection of organic materials that are sensitive to ultraviolet light, especially human and animal skin and hair, against the action of UV radiation. Such UV filter combinations are accordingly suitable as light-protective agents in cosmetic, pharmaceutical and veterinary medicine preparations. Such compounds are preferably used in the dissolved state.

The invention accordingly relates also to a cosmetic preparation comprising the UV filter combination according to the present invention and cosmetically tolerable carriers or adjuvants.

The cosmetic preparation may also comprise, in addition to the UV absorber combination according to the invention, one or more further UV protective agents of the following substance classes:

p-aminobenzoic acid derivatives, benzophenone derivatives, 3-imidazol-4-yl acrylic acid and esters; benzofuran derivatives, polymeric UV absorbers, cinnamic acid derivatives, camphor derivatives, menthyl o-aminobenzoate; merocyanine derivatives; or encapsulated UV absorbers.

The UV absorbers described in "Sunscreens", Eds. N.J. Lowe, N. A. Shaath, Marcel Dekker, Inc., New York and Basle or in Cosmetics & Toiletries (107), 50ff (1992) also can be used as additional UV protective substances.

Special preference is given to the light-protective agents indicated in the following Table 2:

TABLE 3

Suitable UV filter substances and adjuvants which can be additionally used with the UV absorbers of formula MBM-01-MBM-12 according to the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts (Mexoryl SL) | 56039-58-8 |
| 12 | Methyl N,N,N-trimethyl-4-[(4,7,7-trimethyl-3-oxobicyclo[2,2,1]hept-2-ylidene)methyl]anilinium sulphate (Mexoryl SO) | 52793-97-2 |
| 13 | Isopentyl p-methoxycinnamate; isoamyl methoxy cinnamate | 71617-10-2 |
| 14 | 2-ethylhexyl 4-(dimethylamino)benzoate | 21245-02-3 |
| 15 | 2-ethylhexyl 4-methoxycinnamate; Octyl Methoxy Cinnamate | 5466-77-3 |
| 16 | 4-aminobenzoic acid | 150-13-0 |
| 17 | Benzoic acid, 4-amino-, ethyl ester, polymer with oxirane | 113010-52-9 |
| 18 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 19 | Triethanolamine salicylate | 2174-16-5 |
| 20 | 3,3'-(1,4-phenylenedimethylene)bis[7,7-dimethyl-2-oxo-bicyclo[2.2.1]heptane-1 methanesulfonic acid] (Cibafast H) | 90457-82-2 |
| 21 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester; diethylhexyl butamido triazone (Uvasorb HEB) | 154702-15-5 |
| 22 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane (Mexoryl XL) | 155633-54-8 |
| 23 | Dimethicodiethylbenzalmalonate; Polysilicone 15 (Parsol SLX) | 207574-74-1 |
| 24 | Benzenesulfonic acid, 3-(2H-benzotriazol-2-yl)-4-hydroxy-5-(1-methylpropyl)-, monosodium salt (Tinogard HS) | 92484-48-5 |

TABLE 3-continued

Suitable UV filter substances and adjuvants which can be additionally used with the UV absorbers of formula MBM-01-MBM-12 according to the present invention

| No. | Chemical Name | CAS No. |
|---|---|---|
| 25 | 1-Dodecanaminium, N-[3-[[4-(dimethylamino)benzoyl]amino]propyl]-N,N-dimethyl-, salt with 4-methylbenzenesulfonic acid (1:1) (Escalol HP610) | 156679-41-3 |
| 26 | 1-Propanaminium, N,N,N-trimethyl-3-[(1-oxo-3-phenyl-2-propenyl)-amino]-, chloride | 177190-98-6 |
| 27 | 1H-Benzimidazole-4,6-disulfonic acid, 2,2'-(1,4-phenylene)bis- | 170864-82-1 |
| 28 | 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 29 | 2-Propenoic acid, 3-(1H-imidazol-4-yl)- | 104-98-3 |
| 30 | Benzoic acid, 2-hydroxy-, [4-(1-methylethyl)phenyl]methyl ester | 94134-93-7 |
| 31 | 1,2,3-Propanetriol, 1-(4-aminobenzoate) (Glyceryl PABA) | 136-44-7 |
| 32 | Benzeneacetic acid, 3,4-dimethoxy-a-oxo- | 4732-70-1 |
| 33 | 2-Propenoic acid, 2-cyano-3,3-diphenyl-, ethyl ester | 5232-99-5 |
| 34 | Anthralinic acid, p-menth-3-yl ester | 134-09-8 |
| 35 | sterols (cholesterol, lanosterol, phytosterols), as described in WO0341675 | |
| 36 | mycosporines and/or mycosporine-like amino acids as described in WO2002039974, e.g. Helioguard 365 from Milbelle AG, isolated mycosporine like amino acids from the red alga *porphyra umbilicalis* (INCI: *Porphyra Umbilicalis*) that are encapsulated into liposomes) | |
| 37 | alpha-lipoic-acid as described in DE 10229995 | |
| 38 | synthetic organic polymers as described in EP 1 371 358, [0033]-[0041] | |
| 39 | phyllosilicates as described in EP 1371357 [0034]-[0037] | |
| 40 | silica compounds as described in EP1371356, [0033]-[0041] | |
| 41 | inorganic particles as described in DE10138496 [0043]-[0055] | |
| 42 | latex particles as described in DE10138496 [0027]-[0040] | |
| 43 | 1H-Benzimidazole-4,6-disulfonic acid, 2,2'-(1,4-phenylene)bis-, disodium salt; Bisimidazylate (Neo Heliopan APC) | 180898-37-7 |
| 44 | Di-2-ethylhexyl-3,5-dimethoxy-4-hydroxy-benzalmalonate (Oxynex ST, EMD Chemicals, as described in US 20040247536) | |
| 45 | T-LiteTM MAX: Titanium Dioxide (and) Dimethoxydiphenylsilane (and) Triethoxycaprylylsilane Crosspolymer (and) Hydrated Silica (and) Aluminum Hydroxyde | |
| 46 | T-Lite SF: Titanium Dioxide (and) Aluminum Hydroxide (and) Dimethicone/Methicone Copolymer | |
| 47 | T-Lite SF-S: Titanium Dioxide (and) Hydrated Silica (and) Dimethicone/Methicone Copolymer (and) Aluminum Hydroxide | |
| 48 | Z-COTE ® MAX: Zinc Oxide (and) Diphenyl Capryl Methicone | |
| 49 | Z-COTE HP1: Zinc Oxide (and) Triethoxycaprylylsilane | |
| 50 | 1,1-[(2,2'-Dimethylpropoxy)carbonyl]-4,4-diphenyl-1,3-butadiene | 363602-15-7 |
| 51 | UV filter capsules containing an organic sunscreen as described in DE102007035567 or WO 2009012871 | |

In addition, BEMT (Tinosorb S, Bis-Ethylhexyloxyphenol Methoxyphenyl Triazine) encapsulated in a polymer matrix, for example in PMMA, as described in IP.com Journal (2009), 9(1B), 17, can also be used as additional UV protective substance.

The following compounds can also be used as additional UV protective substances:

Merocyanine derivatives as described in WO 2004/006878:

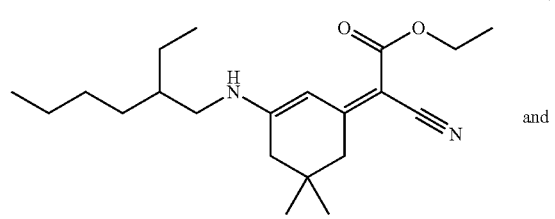

(A)

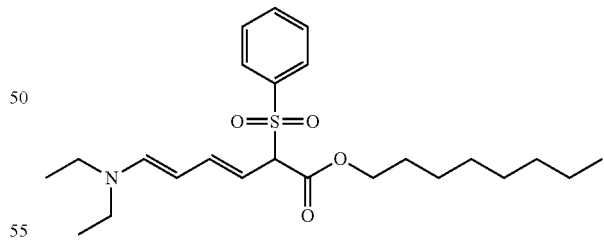

(B)

(A) and (B) can be either in E- or Z-configuration.

Each of the above-mentioned light-protective agents, especially the light-protective agents in the above Tables indicated as being preferred, can be used in admixture with the UV absorber combination according to the invention. It will be understood in that connection that, in addition to the UV absorber combination according to the invention, it is also possible for more than one of the additional light-protective agents to be used, for example, two, three, four, five or six further light-protective agents. Preference is given to the use of mixing ratios of UV absorbers according to the invention/further light-protective agents of from 1:99 to 99:1, especially from 1:95 to 95:1 and preferably from 10:90 to 90:10, based on weight. Of special interest are mixing ratios of from 20:80 to 80:20, especially from 40:60 to 60:40 and preferably of approximately 50:50. Such mixtures can be used, inter alia, to improve solubility or to increase UV absorption.

Appropriate mixtures can be used especially advantageously in a cosmetic composition according to the invention.

The cosmetic compositions contain, for example, from 0.1 to 30% by weight, preferably from 0.1 to 15% by weight and especially from 0.5 to 10% by weight, based on the total weight of the composition, of the UV absorber composition according to the present invention and at least one cosmetically tolerable adjuvant.

The cosmetic compositions can be prepared by physically mixing the UV absorbers with the adjuvant using customary methods, for example by simply stirring together the individual components, especially by making use of the dissolution properties of already known cosmetic UV absorbers, for example OMC, salicylic acid isooctyl ester, inter alia. The UV absorber can be used, for example, without further treatment.

The cosmetic compositions may be, for example, creams, gels, lotions, alcoholic and aqueous/alcoholic solutions, emulsions, wax/fat compositions, stick preparations, powders or ointments.

The compositions according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, pearlescent waxes, consistency regulators, thickeners, polymers, silicone compounds, fats, waxes, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Cosmetic formulations according to the invention are contained in a wide variety of cosmetic preparations. There come into consideration, for example, especially the following preparations: skin-care preparations, bath preparations, skin-care preparations, cosmetic personal care preparations, foot-care preparations, light-protective preparations, skin-tanning preparations, depigmenting preparations, insect-repellents, deodorants, antiperspirants, preparations for cleansing and caring for blemished skin, hair-removal preparations in chemical form (depilation), shaving preparations, fragrance preparations, cosmetic hair-treatment preparations.

The final formulations listed may exist in a wide variety of presentation forms, for example:
in the form of liquid preparations as a W/O, O/W, O/W/O, W/O/W or PIT emulsion and all kinds of microemulsions,
in the form of a gel,
in the form of an oil, a cream, milk or lotion,
in the form of a powder, a lacquer, a tablet or make-up,
in the form of a stick,
in the form of a spray (spray with propellent gas or pump-action spray) or an aerosol,
in the form of a foam, or
in the form of a paste.

Of special importance as cosmetic compositions for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection oils, sun protection milk and sun protection preparations in the form of a spray.

Of special importance as cosmetic compositions for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

The cosmetic preparation according to the invention contains from 0.1 to 15% by weight, preferably from 0.5 to 10% by weight, based on the total weight of the composition, of a UV absorber of formula (1) or of a mixture of UV absorbers and a cosmetically tolerable adjuvant.

The cosmetic preparation can be prepared by physically mixing the UV absorber or UV absorbers with the adjuvant using conventional methods, for example by simply stirring the individual components together.

The cosmetic preparation according to the invention can be formulated as a water-in-oil or oil-in-water emulsion, as an oil-in-alcohol lotion, as a vesicular dispersion of an ionic or non-ionic amphiphilic lipid, as a gel, solid stick or as an aerosol formulation.

As a water-in-oil or oil-in-water emulsion, the cosmetically tolerable adjuvant preferably contains from 5 to 50% of an oil phase, from 5 to 20% of an emulsifier and from 30 to 90% water. The oil phase can comprise any oil suitable for cosmetic formulations, for example one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

For the cosmetic preparation according to the invention it is possible to use any conventionally usable emulsifier, for example one or more ethoxylated esters of natural derivatives, for example polyethoxylated esters of hydrogenated castor oil, or a silicone oil emulsifier, for example silicone polyol; an unethoxylated or ethoxylated fatty acid soap; an ethoxylated fatty alcohol; an unethoxylated or ethoxylated sorbitan ester; an ethoxylated fatty acid; or an ethoxylated glyceride.

The cosmetic preparation according to the invention is distinguished by excellent protection of human skin against the damaging effect of sunlight.

In the following Examples percentages relate to weight. The amounts of the benzylidene malonates compounds used relate to the pure substance.

Method for SPF Measurement

Method to Assess In Vitro Sun Protection Factor Measurement (SPF)

End-product application rate 1.4 mg/cm$^2$ on PMMA plates (Helioplates®)

UV Transmittance analysis with Labsphere UV-1000S Transmittance Analyser $$SPF = \frac{\int_{290nm}^{400nm} E_\lambda \cdot S_\lambda \cdot d\lambda}{\int_{290nm}^{400nm} E_\lambda \cdot S_\lambda \cdot T_\lambda \cdot d\lambda}$$

wherein $E_\lambda$=erythema action spectrum; $S_\lambda$=solar spectral irradiance and $T_\lambda$=spectral transmittance of the sample.

Method to Assess In Vitro UVA Protection Factor (UVA PF)

End-product application rate 1.2 mg/cm² on PMMA plates (Helioplates®)

UV Transmittance analysis with Labsphere UV-1000S Transmittance Analyser

Pre-irradiation step (to take the sun care product photostability into account) via a solar simulator such as Atlas Suntest CPS+

$$PFUVA = \frac{\sum_{320}^{400} \Delta\lambda}{\sum_{320}^{400} T_\lambda \cdot \Delta\lambda} = \frac{1}{T_m}$$

Wherein $T_\lambda$, =sunscreen product transmittance at wave length λ and $T_m$=mean arithmetical value of Transmittance data in the UVA range.

particulate organic filter 50-200 nm, aqueous dispersion, active ingredient particulate organic filter 50-200 nm, encapsulated active ingredient particulate inorganic filter 10-200 nm, active ingredient

| | Example 1: O/W FORMULATION—Anionic System emulsifier | | | | | | | | | |
|---|---|---|---|---|---|---|---|---|---|---|
| | Emulsion high Protection INCI-Name | A % w/w | B % w/w | C % w/w | D % w/w | E % w/w | F % w/w | G % w/w | H % w/w | I % w/w |
| Part A | Cyclomethicone | 2.00 | 2.00 | 2.00 | 2.00 | 2.00 | 2.00 | 2.00 | 2.00 | 2.00 |
| | Phenethyl Benzoate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Ethylhexyl Palmitate | 3.00 | 3.00 | 3.00 | 3.00 | 3.00 | 3.00 | 3.00 | 3.00 | 3.00 |
| | Glyceryl Stearate | 1.50 | 1.50 | 1.50 | 1.50 | 1.50 | 1.50 | 1.50 | 1.50 | 1.50 |
| | Potassium Cetyl Phosphate | 1.80 | 1.80 | 1.80 | 1.80 | 1.80 | 1.80 | 1.80 | 1.80 | 1.80 |
| | VP/Eicosene Copolymer | 0.60 | 0.60 | 0.60 | 0.60 | 0.60 | 0.60 | 0.60 | 0.60 | 0.60 |
| Part B | Aqua | Qs to 100 | Qs to 100 | Qs to 100 | Qs to 100 | Qs to 100 | Qs to 100 | Qs to 100 | Qs to 100 | Qs to 100 |
| | Acrylates/Palmeth-25 Acrylate Copolymer | 0.25 | 0.25 | 0.25 | 0.25 | 0.25 | 0.25 | 0.25 | 0.25 | 0.25 |
| | Glycerin | 6.00 | 6.00 | 6.00 | 6.00 | 6.00 | 6.00 | 6.00 | 6.00 | 6.00 |
| | Disodium EDTA | 0.20 | 0.20 | 0.20 | 0.20 | 0.20 | 0.20 | 0.20 | 0.20 | 0.20 |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.30 | 0.30 | 0.30 | 0.30 | 0.30 | 0.30 | 0.30 | 0.30 | 0.30 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | |
| | Methylene Bis-Benzotriazolyl Tetramethylbutylphenol * | 3.00 | | | 3.00 | 3.00 | 3.00 | | | 3.00 |
| | Diethylamino Hydroxy Benzoyl Hexyl Benzoate | | 4.00 | | 4.00 | | | 4.00 | | 4.00 |
| | Butyl Methoxydibenzoylmethane | | | 3.00 | | 3.00 | | | 3.00 | |
| | Ethylhexyl Triazone | | | | | | 2.00 | 2.00 | 2.00 | 2.00 |
| | In vitro SPF measured according the method described | 25.5 | 20.3 | 16.3 | 23.5 | 19.2 | 33 | 28.6 | 22.2 | 31.6 |
| | UVA PF measured according the method described | 10.7 | 10.6 | 6 | 15.3 | 8.8 | 10.8 | 10.6 | 6 | 15.6 |

Example 2: Sun Milk

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | C12-15 Alkyl Benzoate | 2.00 | 2.00 | 2.00 | 2.00 | 2.00 | 2.00 | 2.00 | 2.00 | 2.00 |
| | Phenethyl Benzoate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Isohexadecane | 3.00 | 3.00 | 3.00 | 3.00 | 3.00 | 3.00 | 3.00 | 3.00 | 3.00 |
| | Cyclopentasiloxane | 4.00 | 4.00 | 4.00 | 4.00 | 4.00 | 4.00 | 4.00 | 4.00 | 4.00 |
| | Stearic Acid | 0.50 | 0.50 | 0.50 | 0.50 | 0.50 | 0.50 | 0.50 | 0.50 | 0.50 |
| | PEG-100 Stearate (and) Glyceryl Stearate | 0.80 | 0.80 | 0.80 | 0.80 | 0.80 | 0.80 | 0.80 | 0.80 | 0.80 |
| | Potassium Cetyl Phosphate | 1.30 | 1.30 | 1.30 | 1.30 | 1.30 | 1.30 | 1.30 | 1.30 | 1.30 |
| | PVP/Eicosene Copolymer | 1.00 | 1.00 | 1.00 | 1.00 | 1.00 | 1.00 | 1.00 | 1.00 | 1.00 |
| Part B | Aqua | Qs to 100 | Qs to 100 | Qs to 100 | Qs to 100 | Qs to 100 | Qs to 100 | Qs to 100 | Qs to 100 | Qs to 100 |
| | Propylene Glycol | 5.00 | 5.00 | 5.00 | 5.00 | 5.00 | 5.00 | 5.00 | 5.00 | 5.00 |
| | Xanthan Gum | 0.20 | 0.20 | 0.20 | 0.20 | 0.20 | 0.20 | 0.20 | 0.20 | 0.20 |
| | Acrylates/C10-30 Alkyl Acrylate Crosspolymer | 0.15 | 0.15 | 0.15 | 0.15 | 0.15 | 0.15 | 0.15 | 0.15 | 0.15 |
| | Disodium EDTA | 0.15 | 0.15 | 0.15 | 0.15 | 0.15 | 0.15 | 0.15 | 0.15 | 0.15 |
| Part C | Triethanolamine | Qs | Qs | Qs | Qs | Qs | Qs | Qs | Qs | Qs |
| | Dimethicone | 0.40 | 0.40 | 0.40 | 0.40 | 0.40 | 0.40 | 0.40 | 0.40 | 0.40 |
| | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.90 | 0.90 | 0.90 | 0.90 | 0.90 | 0.90 | 0.90 | 0.90 | 0.90 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | 2.00 | 2.00 | 2.00 | | | 2.00 | 2.00 | 2.00 |
| | Methylene Bis-Benzotriazolyl Tetramethylbutylphenol * | 3.00 | 3.00 | | | 3.00 | 3.00 | 3.00 | | |
| | Diethylamino Hydroxy Benzoyl Hexyl Benzoate | | | 4.00 | | 4.00 | | | 4.00 | |
| | Butyl Methoxydibenzoyl-methane | 3.00 | | | 3.00 | | 3.00 | | | 3.00 |
| | Ethylhexyl Triazone | 2.00 | 2.00 | 2.00 | 2.00 | 2.00 | 2.00 | 2.00 | 2.00 | 2.00 |
| | Ethylhexyl Salicylate | | 5.00 | | | | | | | |
| | Tris-Biphenyl Triazine * | | | 2.00 | | | | | | |
| | Octocrylene | | | | 8.00 | | | | | |
| | Diethylhexyl Butamido Triazone | | | | | 1.00 | | | | |
| | Phenylbenzimidazole Sulfonic Acid | | | | | | 2.00 | | | |
| | Titanium Dioxide *** | | | | | | | 2.00 | | |
| | Homosalate | | | | | | | | 10.00 | |
| | Methanone, 1,1'-(1,4-piperazine-diyl)bis[1-[2-[4-(diethylamino)-2-hydroxybenzoyl]phenyl]- CAS number (919803-06-8) * | | | | | | | | | 2.00 |
| | In vitro SPF measured according the method described | 25.4 | 35.7 | 38.1 | 33.5 | 36.3 | 31.7 | 38.5 | 34.8 | 25 |
| | UVA PF measured according the method described | 8.9 | 10.8 | 14.6 | 7.8 | 15.6 | 8.9 | 11.6 | 10.7 | 7.6 |

Example 3: Every Day Lotion

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Stearyl Phosphate | 5.00 | 5.00 | 5.00 | 5.00 | 5.00 | 5.00 | 5.00 | 5.00 | 5.00 |
| | Phenethyl Benzoate | 3.00 | 3.00 | 3.00 | 3.00 | 3.00 | 3.00 | 3.00 | 3.00 | 3.00 |
| | Triisodecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Tricontanyl PVP | 1.00 | 1.00 | 1.00 | 1.00 | 1.00 | 1.00 | 1.00 | 1.00 | 1.00 |
| | Ethoxydiglycol Oleate | 1.50 | 1.50 | 1.50 | 1.50 | 1.50 | 1.50 | 1.50 | 1.50 | 1.50 |
| | Squalane | 3.00 | 3.00 | 3.00 | 3.00 | 3.00 | 3.00 | 3.00 | 3.00 | 3.00 |

Example 3: Every Day Lotion

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| | C12-15 Alkyl Benzoate | 2.00 | 2.00 | 2.00 | 2.00 | 2.00 | 2.00 | 2.00 | 2.00 | 2.00 |
| | Glyceryl Stearate | 2.00 | 2.00 | 2.00 | 2.00 | 2.00 | 2.00 | 2.00 | 2.00 | 2.00 |
| | Cetyl Alcohol | 2.00 | 2.00 | 2.00 | 2.00 | 2.00 | 2.00 | 2.00 | 2.00 | 2.00 |
| Part B | Aqua | qs to 100 | qs to 100 | qs to 100 | qs to 100 | qs to 100 | qs to 100 | qs to 100 | qs to 100 | qs to 100 |
| | Steareth-10 Allyl Ether/Acrylates Copolymer | 0.50 | 0.50 | 0.50 | 0.50 | 0.50 | 0.50 | 0.50 | 0.50 | 0.50 |
| | Glycerin | 2.50 | 2.50 | 2.50 | 2.50 | 2.50 | 2.50 | 2.50 | 2.50 | 2.50 |
| | Diazolidinyl Urea (and) Iodopropynyl Butylcarbamate | 0.15 | 0.15 | 0.15 | 0.15 | 0.15 | 0.15 | 0.15 | 0.15 | 0.15 |
| | Sodium Lauroyl Glutamate | 0.70 | 0.70 | 0.70 | 0.70 | 0.70 | 0.70 | 0.70 | 0.70 | 0.70 |
| Part C | Cyclopentasiloxane (and) Dimethiconol | 1.50 | 1.50 | 1.50 | 1.50 | 1.50 | 1.50 | 1.50 | 1.50 | 1.50 |
| | Triethanolamine | 1.85 | 1.85 | 1.85 | 1.85 | 1.85 | 1.85 | 1.85 | 1.85 | 1.85 |
| | Citric Acid (and) Silver Citrate | 0.10 | 0.10 | 0.10 | 0.10 | 0.10 | 0.10 | 0.10 | 0.10 | 0.10 |
| | Sclerotium Gum | 0.10 | 0.10 | 0.10 | 0.10 | 0.10 | 0.10 | 0.10 | 0.10 | 0.10 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | | 2.00 | 2.00 | 2.00 | 2.00 | 2.00 | 2.00 | 2.00 |
| | Methylene Bis-Benzotriazolyl Tetramethylbutylphenol * | 3.00 | 3.00 | 3.00 | 3.00 | 3.00 | 3.00 | 3.00 | 3.00 | 3.00 |
| | Diethylamino Hydroxy Benzoyl Hexyl Benzoate | 4.00 | | | 4.00 | 4.00 | 4.00 | 4.00 | 4.00 | 4.00 |
| | Butyl Methoxydibenzoyl-methane | | 3.00 | | | 3.00 | | | | |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | 2.00 | | | 2.00 |
| | Methanone, 1,1'-(1,4-piperazine-diyl)bis[1-[2-[4-(diethylamino)-2-hydroxybenzoyl]phenyl]- CAS number (919803-06-8) * | | | | | | | 2.00 | | |
| | Ethylhexyl Methoxycinnamate | 7.00 | | | | | | | | 5.00 |
| | Bis-Ethylhexyloxyphenol Methoxyphenyl Triazine ** | | 2.00 | | | | | | 2.00 | |
| | Merocyanine A or B | | | 1.00 | | | | | | 0.50 |
| | In vitro SPF measured according the method described | 39.6 | 32.9 | 36 | 39.8 | 36.4 | 50.7 | 42.3 | 49.2 | 59 |
| | UVA PF measured according the method described | 15.9 | 10.9 | 13.8 | 20.1 | 17.6 | 23.2 | 22 | 24.7 | 26.2 |

Example 4: Every Day Lotion—Nonionic System emulsifier—O/W FORMULATION

| | Sun Cream INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Tribehenin PEG-20 esters | 5.00 | 5.00 | 5.00 | 5.00 | 5.00 | 5.00 | 5.00 | 5.00 | 5.00 |
| | Phenethyl Benzoate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Dibutyl adipate | 2.00 | 2.00 | 2.00 | 2.00 | 2.00 | 2.00 | 2.00 | 2.00 | 2.00 |
| | PPG-2 Myristyl Ether Propionate | 2.00 | 2.00 | 2.00 | 2.00 | 2.00 | 2.00 | 2.00 | 2.00 | 2.00 |
| Part B | Aqua | Qs to 100 | Qs to 100 | Qs to 100 | Qs to 100 | Qs to 100 | Qs to 100 | Qs to 100 | Qs to 100 | Qs to 100 |
| | PVP/dimethylconylacrylate/polycarbamyl/polyglycol ester | 3.00 | 3.00 | 3.00 | 3.00 | 3.00 | 3.00 | 3.00 | 3.00 | 3.00 |
| | Disodium EDTA | 0.20 | 0.20 | 0.20 | 0.20 | 0.20 | 0.20 | 0.20 | 0.20 | 0.20 |
| | Sclerotium Gum | 2.00 | 2.00 | 2.00 | 2.00 | 2.00 | 2.00 | 2.00 | 2.00 | 2.00 |
| | Ammonium Acryldimethyltaurate/Beneth-25 Methacrylate Crosspolymer. | 0.50 | 0.50 | 0.50 | 0.50 | 0.50 | 0.50 | 0.50 | 0.50 | 0.50 |

| Example 4: Every Day Lotion—Nonionic System emulsifier—O/W FORMULATION | | | | | | | | | | |
|---|---|---|---|---|---|---|---|---|---|---|
| | Sun Cream INCI-Name | A % w/w | B % w/w | C % w/w | D % w/w | E % w/w | F % w/w | G % w/w | H % w/w | I % w/w |
| Part C | Cyclopentasiloxane (and) cyclohexasiloxane | 4.00 | 4.00 | 4.00 | 4.00 | 4.00 | 4.00 | 4.00 | 4.00 | 4.00 |
| | Phenoxyethanol (and) Methylparaben (and) Ethyl-paraben (and) Butylparaben (and) Propylparaben (and) Isobutylparaben | 1.00 | 1.00 | 1.00 | 1.00 | 1.00 | 1.00 | 1.00 | 1.00 | 1.00 |
| | Sodium Hydroxide (and) Aqua | Qsp | Qsp | Qsp | Qsp | Qsp | Qsp | Qsp | Qsp | Qsp |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | 2.00 |
| | Methylene Bis-Benzotriazolyl Tetramethylbutylphenol * | 3.00 | | | 3.00 | 3.00 | | | | |
| | Diethylamino Hydroxy Benzoyl Hexyl Benzoate | | 4.00 | | 4.00 | | 4.00 | 4.00 | | 4.00 |
| | Butyl Methoxydibenzoyl-methane | | | 3.00 | | 3.00 | | | 3.00 | 3.00 |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | | 2.00 | | |
| | Methanone, 1,1'-(1,4-piperazine-diyl)bis[1-[2-[4-(diethylamino)-2-hydroxybenzoyl]phenyl]- CAS number (919803-06-8) * | | | | | | | | 2.00 | |
| | Zinc Oxide | 4.00 | | | | | | | | |
| | Isoamyl p-Methoxycinnamate | | 3.00 | | | | | | | |
| | Polysilicone-15 | | | 5.00 | | | | | | |
| | Disodium Phenyl Dibenzylmidazole Tetrasulfonate | | | | 2.00 | | | | | |
| | Benzophenone-3 | | | | | 3.00 | | | | |
| | Terephthalylidene Dicamphor Sulfonic Acid | | | | | | 1.00 | 1.00 | 1.00 | 1.00 |
| | Drometrizole Trisiloxane | | | | | | 1.00 | 1.00 | 1.00 | 1.00 |
| | Bis-Ethylhexyloxyphenol Methoxyphenyl Triazine ** | | | | | | | | | 2.00 |
| | In vitro SPF measured according the method described | 37.6 | 33.3 | 24.2 | 25.2 | 29.7 | 32.5 | 42.4 | 28.8 | 37.3 |
| | UVA PF measured according the method described | 13.5 | 10.7 | 6.1 | 10.6 | 10 | 14.7 | 17.8 | 10.5 | 16.2 |

| Example 5: Every Day Lotion—Nonionic System emulsifier—O/W FORMULATION | | | | | | | | | | |
|---|---|---|---|---|---|---|---|---|---|---|
| | UV-A/UV-B Daily Care UV Protection Lotion INCI-Name | A % w/w | B % w/w | C % w/w | D % w/w | E % w/w | F % w/w | G % w/w | H % w/w | I % w/w |
| Part A | Oleth-3 Phosphate | 0.60 | 0.60 | 0.60 | 0.60 | 0.60 | 0.60 | 0.60 | 0.60 | 0.60 |
| | Steareth-21 | 2.50 | 2.50 | 2.50 | 2.50 | 2.50 | 2.50 | 2.50 | 2.50 | 2.50 |
| | Steareth-2 | 1.00 | 1.00 | 1.00 | 1.00 | 1.00 | 1.00 | 1.00 | 1.00 | 1.00 |
| | Phenethyl Benzoate | 4.00 | 4.00 | 4.00 | 4.00 | 4.00 | 4.00 | 4.00 | 4.00 | 4.00 |
| | Triisodecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Cetyl Alcohol | 0.80 | 0.80 | 0.80 | 0.80 | 0.80 | 0.80 | 0.80 | 0.80 | 0.80 |
| | Stearyl Alcohol | 1.50 | 1.50 | 1.50 | 1.50 | 1.50 | 1.50 | 1.50 | 1.50 | 1.50 |
| | Tribehenin | 0.80 | 0.80 | 0.80 | 0.80 | 0.80 | 0.80 | 0.80 | 0.80 | 0.80 |
| | Isohexadecane | 4.00 | 4.00 | 4.00 | 4.00 | 4.00 | 4.00 | 4.00 | 4.00 | 4.00 |
| Part B | Aqua | qs to 100 | qs to 100 | qs to 100 | qs to 100 | qs to 100 | qs to 100 | qs to 100 | qs to 100 | qs to 100 |
| | Glycerin | 2.00 | 2.00 | 2.00 | 2.00 | 2.00 | 2.00 | 2.00 | 2.00 | 2.00 |
| | Disodium EDTA | 0.10 | 0.10 | 0.10 | 0.10 | 0.10 | 0.10 | 0.10 | 0.10 | 0.10 |
| Part C | Aqua | 20.00 | 20.00 | 20.00 | 20.00 | 20.00 | 20.00 | 20.00 | 20.00 | 20.00 |
| | Diazolidinyl Urea (and) iodopropynyl Butyl-carbamate | 0.15 | 0.15 | 0.15 | 0.15 | 0.15 | 0.15 | 0.15 | 0.15 | 0.15 |
| | Propylene Glycol | 4.00 | 4.00 | 4.00 | 4.00 | 4.00 | 4.00 | 4.00 | 4.00 | 4.00 |

-continued

Example 5: Every Day Lotion—Nonionic System emulsifier—O/W FORMULATION

| | UV-A/UV-B Daily Care UV Protection Lotion INCI-Name | A % w/w | B % w/w | C % w/w | D % w/w | E % w/w | F % w/w | G % w/w | H % w/w | I % w/w |
|---|---|---|---|---|---|---|---|---|---|---|
| Part D | Sodium Acrylates Co-polymer (and) Paraffinium Liquidum (and) PPG-1 Trideceth-6 | 1.50 | 1.50 | 1.50 | 1.50 | 1.50 | 1.50 | 1.50 | 1.50 | 1.50 |
| | Cyclopentasiloxane | 4.00 | 4.00 | 4.00 | 4.00 | 4.00 | 4.00 | 4.00 | 4.00 | 4.00 |
| | PEG-12 Dimethicone | 2.00 | 2.00 | 2.00 | 2.00 | 2.00 | 2.00 | 2.00 | 2.00 | 2.00 |
| | Tocopheryl Acetate | 0.45 | 0.45 | 0.45 | 0.45 | 0.45 | 0.45 | 0.45 | 0.45 | 0.45 |
| | Water (and) Citric Acid | Qs | Qs | Qs | Qs | Qs | Qs | Qs | Qs | Qs |
| | Fragrance | Qs | Qs | Qs | Qs | Qs | Qs | Qs | Qs | Qs |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | |
| | Methylene Bis-Benzotriazolyl Tetramethylbutylpheno * | 3.00 | | | 3.00 | 3.00 | 3.00 | | | 3.00 |
| | Diethylamino Hydroxy Benzoyl Hexyl Benzoate | | 4.00 | | 4.00 | | | 4.00 | | 4.00 |
| | Butyl Methoxydibenzoyl-methane | | | 3.00 | | 3.00 | | | 3.00 | |
| | Ethylhexyl Triazone | | | | | | 2.00 | 2.00 | 2.00 | 2.00 |
| | In vitro SPF measured according the method described | 25.5 | 20.3 | 16.3 | 23.5 | 19.2 | 33 | 28.6 | 22.2 | 31.6 |
| | UVA PF measured according the method described | 10.7 | 10.6 | 6 | 15.3 | 8.8 | 10.8 | 10.6 | 6 | 15.6 |

Example 6: Daily Care Lotion

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Polyglyceryl Methyl Glucose Distearate | 2.50 | 2.50 | 2.50 | 2.50 | 2.50 | 2.50 | 2.50 | 2.50 | 2.50 |
| | Phenethyl Benzoate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Cetearyl Alcohol | 2.00 | 2.00 | 2.00 | 2.00 | 2.00 | 2.00 | 2.00 | 2.00 | 2.00 |
| | Octyl Stearate | 3.00 | 3.00 | 3.00 | 3.00 | 3.00 | 3.00 | 3.00 | 3.00 | 3.00 |
| | Caprylic/Capric Triglyceride | 1.00 | 1.00 | 1.00 | 1.00 | 1.00 | 1.00 | 1.00 | 1.00 | 1.00 |
| | Isohexadecane | 2.00 | 2.00 | 2.00 | 2.00 | 2.00 | 2.00 | 2.00 | 2.00 | 2.00 |
| Part B | Aqua | 64.80 | 64.80 | 64.80 | 64.80 | 64.80 | 64.80 | 64.80 | 64.80 | 64.80 |
| | Glycerin | 5.00 | 5.00 | 5.00 | 5.00 | 5.00 | 5.00 | 5.00 | 5.00 | 5.00 |
| Part C | Phenoxyethanol (and) Methylparaben (and) Butylparaben (and) Ethylparaben (and) Propylparaben | 0.50 | 0.50 | 0.50 | 0.50 | 0.50 | 0.50 | 0.50 | 0.50 | 0.50 |
| | Cyclomethicone (and) Dimethicone | 3.00 | 3.00 | 3.00 | 3.00 | 3.00 | 3.00 | 3.00 | 3.00 | 3.00 |
| | Steareth-10 Allyl Ether/Acrylates Copolymer | 0.50 | 0.50 | 0.50 | 0.50 | 0.50 | 0.50 | 0.50 | 0.50 | 0.50 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | 2.00 | 2.00 | 2.00 | | | 2.00 | 2.00 | 2.00 |
| | Methylene Bis-Benzotriazolyl Tetramethylbutylphenol * | 3.00 | 3.00 | | | 3.00 | 3.00 | 3.00 | | |
| | Diethylamino Hydroxy Benzoyl Hexyl Benzoate | | | 4.00 | | 4.00 | | | 4.00 | |
| | Butyl Methoxydibenzoyl-methane | 3.00 | | | 3.00 | | 3.00 | | | 3.00 |
| | Ethylhexyl Triazone | 2.00 | 2.00 | 2.00 | 2.00 | 2.00 | 2.00 | 2.00 | 2.00 | 2.00 |
| | Ethylhexyl Salicylate | | 5.00 | | | | | | | |
| | Tris-Biphenyl Triazine * | | | 2.00 | | | | | | |

Example 6: Daily Care Lotion

| INCI-Name | A % w/w | B % w/w | C % w/w | D % w/w | E % w/w | F % w/w | G % w/w | H % w/w | I % w/w |
|---|---|---|---|---|---|---|---|---|---|
| Octocrylene | | | | 8.00 | | | | | |
| Diethylhexyl Butamido Triazone | | | | | | 1.00 | | | |
| Phenylbenzimidazole Sulfonic Acid | | | | | | | 2.00 | | |
| Titanium Dioxide *** | | | | | | | | 2.00 | |
| Homosalate | | | | | | | | | 10.00 |
| Methanone, 1,1'-(1,4-piperazine-diyl)bis[1-[2-[4-(diethylamino)-2-hydroxybenzoyl]phenyl]- CAS number (919803-06-8) * | | | | | | | | | 2.00 |
| In vitro SPF measured according the method described | 25.4 | 35.7 | 38.1 | 33.5 | 36.3 | 31.7 | 38.5 | 34.8 | 25 |
| UVA PF measured according the method described | 8.9 | 10.8 | 14.6 | 7.8 | 15.6 | 8.9 | 11.6 | 10.7 | 7.6 |

Example 7: O/W FORMULATION—Sunscreen Gel

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| | Alcohol Denatured | Qs to 100 | Qs to 100 | Qs to 100 | Qs to 100 | Qs to 100 | Qs to 100 | Qs to 100 | Qs to 100 | Qs to 100 |
| | Phenethyl Benzoate | 2.00 | 2.00 | 2.00 | 2.00 | 2.00 | 2.00 | 2.00 | 2.00 | 2.00 |
| | Triisodecyl Trimellitate | 1.00 | 1.00 | 1.00 | 1.00 | 1.00 | 1.00 | 1.00 | 1.00 | 1.00 |
| | Dimethyl Capramide | 0.50 | 0.50 | 0.50 | 0.50 | 0.50 | 0.50 | 0.50 | 0.50 | 0.50 |
| | Hydroxypropyl Cellulose | 1.00 | 1.00 | 1.00 | 1.00 | 1.00 | 1.00 | 1.00 | 1.00 | 1.00 |
| | Acrylates/Octylacrylamide Copolymer | 1.00 | 1.00 | 1.00 | 1.00 | 1.00 | 1.00 | 1.00 | 1.00 | 1.00 |
| | C12-15 Alkyl Benzoate | 10.00 | 10.00 | 10.00 | 10.00 | 10.00 | 10.00 | 10.00 | 10.00 | 10.00 |
| | Cyclotetrasiloxane (and) Cyclopentasiloxane | 3.00 | 3.00 | 3.00 | 3.00 | 3.00 | 3.00 | 3.00 | 3.00 | 3.00 |
| | PEG/PPG-4/12 Dimethicone | 1.00 | 1.00 | 1.00 | 1.00 | 1.00 | 1.00 | 1.00 | 1.00 | 1.00 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | | 2.00 | 2.00 | 2.00 | 2.00 | 2.00 | 2.00 | 2.00 |
| | Methylene Bis-Benzotriazolyl Tetramethylbutylphenol * | 3.00 | 3.00 | 3.00 | 3.00 | 3.00 | 3.00 | 3.00 | 3.00 | 3.00 |
| | Diethylamino Hydroxy Benzoyl Hexyl Benzoate | 4.00 | | | 4.00 | 4.00 | 4.00 | 4.00 | 4.00 | 4.00 |
| | Butyl Methoxydibenzoyl-methane | | 3.00 | | | 3.00 | | | | |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | | 2.00 | | 2.00 |
| | Methanone, 1,1'-(1,4-piperazine-diyl)bis[1-[2-[4-(diethylamino)-2-hydroxybenzoyl]phenyl]- CAS number (919803-06-8) * | | | | | | | 2.00 | | |
| | Ethylhexyl Methoxycinnamate | 7.00 | | | | | | | | 5.00 |
| | Bis-Ethylhexyloxyphenol Methoxyphenyl Triazine ** | | 2.00 | | | | | | 2.00 | |
| | Merocyanine A or B | | | 1.00 | | | | | | 0.50 |
| | In vitro SPF measured according the method described | 39.6 | 32.9 | 36 | 39.8 | 36.4 | 50.7 | 42.3 | 49.2 | 59 |
| | UVA PF measured according the method described | 15.9 | 10.9 | 13.8 | 20.1 | 17.6 | 23.2 | 22 | 24.7 | 26.2 |

| Example 8: Gel Cream | | | | | | | | | | |
|---|---|---|---|---|---|---|---|---|---|---|
| | Gel Cream<br>INCI-Name | A<br>% w/w | B<br>% w/w | C<br>% w/w | D<br>% w/w | E<br>% w/w | F<br>% w/w | G<br>% w/w | H<br>% w/w | I<br>% w/w |
| | Acrylate/C10-30 Alkyl-acrylate Crosspolymer | 0.40 | 0.40 | 0.40 | 0.40 | 0.40 | 0.40 | 0.40 | 0.40 | 0.40 |
| | Polyacrylic Acid | 0.20 | 0.20 | 0.20 | 0.20 | 0.20 | 0.20 | 0.20 | 0.20 | 0.20 |
| | Phenethyl Benzoate | 2.00 | 2.00 | 2.00 | 2.00 | 2.00 | 2.00 | 2.00 | 2.00 | 2.00 |
| | Dimethyl Capramide | 0.50 | 0.50 | 0.50 | 0.50 | 0.50 | 0.50 | 0.50 | 0.50 | 0.50 |
| | Xanthan Gum | 0.10 | 0.10 | 0.10 | 0.10 | 0.10 | 0.10 | 0.10 | 0.10 | 0.10 |
| | Cetearyl alcohol | 3.00 | 3.00 | 3.00 | 3.00 | 3.00 | 3.00 | 3.00 | 3.00 | 3.00 |
| | C12-15 Alkylbenzoate | 2.00 | 2.00 | 2.00 | 2.00 | 2.00 | 2.00 | 2.00 | 2.00 | 2.00 |
| | Caprylic/Capric Triglyceride | 1.00 | 1.00 | 1.00 | 1.00 | 1.00 | 1.00 | 1.00 | 1.00 | 1.00 |
| | Dimethicone | 5.00 | 5.00 | 5.00 | 5.00 | 5.00 | 5.00 | 5.00 | 5.00 | 5.00 |
| | Dimethiconol | 1.00 | 1.00 | 1.00 | 1.00 | 1.00 | 1.00 | 1.00 | 1.00 | 1.00 |
| | Glycerin | 3.00 | 3.00 | 3.00 | 3.00 | 3.00 | 3.00 | 3.00 | 3.00 | 3.00 |
| | Sodium Hydroxyde | q.s. | q.s. | q.s. | q.s. | q.s. | q.s. | q.s. | q.s. | q.s. |
| | Preservative | .q.s. | .q.s. | .q.s. | .q.s. | .q.s. | .q.s. | .q.s. | .q.s. | .q.s. |
| | Parfum | q.s. | q.s. | q.s. | q.s. | q.s. | q.s. | q.s. | q.s. | q.s. |
| | Aqua | ad 100.0 | ad 100.0 | ad 100.0 | ad 100.0 | ad 100.0 | ad 100.0 | ad 100.0 | ad 100.0 | ad 100.0 |
| | PH-value adjusted to 6.0 | | | | | | | | | |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | 2.00 |
| | Methylene Bis-Benzotriazolyl Tetramethylbutylphenol * | 3.00 | | | 3.00 | 3.00 | | | | |
| | Diethylamino Hydroxy Benzoyl Hexyl Benzoate | | 4.00 | | 4.00 | | 4.00 | 4.00 | | 4.00 |
| | Butyl Methoxydibenzoyl-methane | | | 3.00 | | 3.00 | | | 3.00 | 3.00 |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | | 2.00 | | |
| | Methanone, 1,1'-(1,4-piperazine-diyl)bis[1-[2-[4-(diethylamino)-2-hydroxybenzoyl]phenyl]- CAS number (919803-06-8) * | | | | | | | | 2.00 | |
| | Zinc Oxide | 4.00 | | | | | | | | |
| | Isoamyl p-Methoxycinnamate | | 3.00 | | | | | | | |
| | Polysilicone-15 | | | 5.00 | | | | | | |
| | Disodium Phenyl Dibenzylimidazole Tetrasulfonate | | | | 2.00 | | | | | |
| | Benzophenone-3 | | | | | 3.00 | | | | |
| | Terephthalylidene Di-camphor Sulfonic Acid | | | | | | 1.00 | 1.00 | 1.00 | 1.00 |
| | Drometrizole Trisiloxane | | | | | | 1.00 | 1.00 | 1.00 | 1.00 |
| | Bis-Ethylhexyloxyphenol Methoxyphenyl Triazine ** | | | | | | | | | 2.00 |
| | In vitro SPF measured according the method described | 37.6 | 33.3 | 24.2 | 25.2 | 29.7 | 32.5 | 42.4 | 28.8 | 37.3 |
| | UVA PF measured according the method described | 13.5 | 10.7 | 6.1 | 10.6 | 10 | 14.7 | 17.8 | 10.5 | 16.2 |

| Example 9: O/W FORMULATION—Emulsifier free | | | | | | | | | |
|---|---|---|---|---|---|---|---|---|---|
| INCI-Name | A<br>% w/w | B<br>% w/w | C<br>% w/w | D<br>% w/w | E<br>% w/w | F<br>% w/w | G<br>% w/w | H<br>% w/w | I<br>% w/w |
| Acrylates/C10-30 Alkyl Acrylate Crosspolymer | 0.40 | 0.40 | 0.40 | 0.40 | 0.40 | 0.40 | 0.40 | 0.40 | 0.40 |
| Xanthan Gum | 0.15 | 0.15 | 0.15 | 0.15 | 0.15 | 0.15 | 0.15 | 0.15 | 0.15 |
| Ethylhexyloxyglycerine | 1.00 | 1.00 | 1.00 | 1.00 | 1.00 | 1.00 | 1.00 | 1.00 | 1.00 |
| Butylene Glycol | 10.00 | 10.00 | 10.00 | 10.00 | 10.00 | 10.00 | 10.00 | 10.00 | 10.00 |
| *Glycine Soja* | 1.00 | 1.00 | 1.00 | 1.00 | 1.00 | 1.00 | 1.00 | 1.00 | 1.00 |
| Tocopheryl Acetate | 0.25 | 0.25 | 0.25 | 0.25 | 0.25 | 0.25 | 0.25 | 0.25 | 0.25 |
| PETP | 1.00 | 1.00 | 1.00 | 1.00 | 1.00 | 1.00 | 1.00 | 1.00 | 1.00 |
| Trisodium EDTA | 0.10 | 0.10 | 0.10 | 0.10 | 0.10 | 0.10 | 0.10 | 0.10 | 0.10 |
| Ethanol | 3.50 | 3.50 | 3.50 | 3.50 | 3.50 | 3.50 | 3.50 | 3.50 | 3.50 |

-continued

Example 9: O/W FORMULATION—Emulsifier free

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| | Parfume | 0.20 | 0.20 | 0.20 | 0.20 | 0.20 | 0.20 | 0.20 | 0.20 | 0.20 |
| | Watersoluble Dyes | 0.02 | 0.02 | 0.02 | 0.02 | 0.02 | 0.02 | 0.02 | 0.02 | 0.02 |
| | Aqua | ad 100 | ad 100 | ad 100 | ad 100 | ad 100 | ad 100 | ad 100 | ad 100 | ad 100 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | |
| | Methylene Bis-Benzotriazolyl Tetramethylbutylphenol * | 3.00 | | | 3.00 | 3.00 | 3.00 | | | 3.00 |
| | Diethylamino Hydroxy Benzoyl Hexyl Benzoate | | 4.00 | | 4.00 | | | 4.00 | | 4.00 |
| | Butyl Methoxydibenzoyl-methane | | | 3.00 | | 3.00 | | | 3.00 | |
| | Ethylhexyl Triazone | | | | | | 2.00 | 2.00 | 2.00 | 2.00 |
| | In vitro SPF measured according the method described | 25.5 | 20.3 | 16.3 | 23.5 | 19.2 | 33 | 28.6 | 22.2 | 31.6 |
| | UVA PF measured according the method described | 10.7 | 10.6 | 6 | 15.3 | 8.8 | 10.8 | 10.6 | 6 | 15.6 |

Example 10: SPRAY FORMULATION—Classic

| | Sprayable Sunscreen Lotion INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Potassium Cetyl Phosphate | 0.20 | 0.20 | 0.20 | 0.20 | 0.20 | 0.20 | 0.20 | 0.20 | 0.20 |
| | Isohexadecane | 5.00 | 5.00 | 5.00 | 5.00 | 5.00 | 5.00 | 5.00 | 5.00 | 5.00 |
| | Phenethyl Benzoate | 4.00 | 4.00 | 4.00 | 4.00 | 4.00 | 4.00 | 4.00 | 4.00 | 4.00 |
| | Triisodecyl Trimellitate | 2.00 | 2.00 | 2.00 | 2.00 | 2.00 | 2.00 | 2.00 | 2.00 | 2.00 |
| | Dimethyl Capramide | 1.00 | 1.00 | 1.00 | 1.00 | 1.00 | 1.00 | 1.00 | 1.00 | 1.00 |
| | VP/Eicosene Copolymer | 1.50 | 1.50 | 1.50 | 1.50 | 1.50 | 1.50 | 1.50 | 1.50 | 1.50 |
| | Di-C12-13 Alkyl Tartrate | 4.00 | 4.00 | 4.00 | 4.00 | 4.00 | 4.00 | 4.00 | 4.00 | 4.00 |
| | C12-15 Alkyl Benzoate | 1.50 | 1.50 | 1.50 | 1.50 | 1.50 | 1.50 | 1.50 | 1.50 | 1.50 |
| Part B | Aqua | qs to 100 | qs to 100 | qs to 100 | qs to 100 | qs to 100 | qs to 100 | qs to 100 | qs to 100 | qs to 100 |
| | Sorbeth-30 | 2.00 | 2.00 | 2.00 | 2.00 | 2.00 | 2.00 | 2.00 | 2.00 | 2.00 |
| | Sorbitan Stearate (and) Sucrose Cocoate | 4.00 | 4.00 | 4.00 | 4.00 | 4.00 | 4.00 | 4.00 | 4.00 | 4.00 |
| | Aqua | 30.00 | 30.00 | 30.00 | 30.00 | 30.00 | 30.00 | 30.00 | 30.00 | 30.00 |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| Part D | Water (and) Citric Acid | qs | qs | qs | qs | qs | qs | qs | qs | qs |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | 2.00 | 2.00 | 2.00 | | | 2.00 | 2.00 | 2.00 |
| | Methylene Bis-Benzotriazolyl Tetramethylbutylphenol * | 3.00 | 3.00 | | | 3.00 | 3.00 | 3.00 | | |
| | Diethylamino Hydroxy Benzoyl Hexyl Benzoate | | | 4.00 | | 4.00 | | | 4.00 | |
| | Butyl Methoxydibenzoyl-methane | 3.00 | | | 3.00 | | 3.00 | | | 3.00 |
| | Ethylhexyl Triazone | 2.00 | 2.00 | 2.00 | 2.00 | 2.00 | 2.00 | 2.00 | 2.00 | 2.00 |
| | Ethylhexyl Salicylate | | 5.00 | | | | | | | |
| | Tris-Biphenyl Triazine * | | | 2.00 | | | | | | |
| | Octocrylene | | | | 8.00 | | | | | |
| | Diethylhexyl Butamido Triazone | | | | | 1.00 | | | | |
| | Phenylbenzimidazole Sulfonic Acid | | | | | | 2.00 | | | |
| | Titanium Dioxide *** | | | | | | | 2.00 | | |
| | Homosalate | | | | | | | | 10.00 | |

Example 10: SPRAY FORMULATION—Classic

| Sprayable Sunscreen Lotion INCI-Name | A % w/w | B % w/w | C % w/w | D % w/w | E % w/w | F % w/w | G % w/w | H % w/w | I % w/w |
|---|---|---|---|---|---|---|---|---|---|
| Methanone, 1,1'-(1,4-piperazine-diyl)bis[1-[2-[4-(diethylamino)-2-hydroxybenzoyl]phenyl]- CAS number (919803-06-8) * | | | | | | | | | 2.00 |
| In vitro SPF measured according the method described | 25.4 | 35.7 | 38.1 | 33.5 | 36.3 | 31.7 | 38.5 | 34.8 | 25 |
| UVA PF measured according the method described | 8.9 | 10.8 | 14.6 | 7.8 | 15.6 | 8.9 | 11.6 | 10.7 | 7.6 |

Example 11: COLD PROCESS SPRAY

| | COLD PROCESS SPRAY INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Sorbitan-30 | 3.00 | 3.00 | 3.00 | 3.00 | 3.00 | 3.00 | 3.00 | 3.00 | 3.00 |
| Part B | Isostearyl Alcohol | 2.00 | 2.00 | 2.00 | 2.00 | 2.00 | 2.00 | 2.00 | 2.00 | 2.00 |
| | Phenethyl Benzoate | 4.00 | 4.00 | 4.00 | 4.00 | 4.00 | 4.00 | 4.00 | 4.00 | 4.00 |
| | Tridecyl Trimellitate | 2.00 | 2.00 | 2.00 | 2.00 | 2.00 | 2.00 | 2.00 | 2.00 | 2.00 |
| | Dimethyl Capramide | 1.00 | 1.00 | 1.00 | 1.00 | 1.00 | 1.00 | 1.00 | 1.00 | 1.00 |
| | Sorbitan Oleate (and) Polyglycerol 3-Polyricinoleate | 2.00 | 2.00 | 2.00 | 2.00 | 2.00 | 2.00 | 2.00 | 2.00 | 2.00 |
| | Polysorbate-20 | 1.00 | 1.00 | 1.00 | 1.00 | 1.00 | 1.00 | 1.00 | 1.00 | 1.00 |
| | Dimethicone | 1.00 | 1.00 | 1.00 | 1.00 | 1.00 | 1.00 | 1.00 | 1.00 | 1.00 |
| Part C | DMDM Hydantoin | 1.00 | 1.00 | 1.00 | 1.00 | 1.00 | 1.00 | 1.00 | 1.00 | 1.00 |
| | Aqua | Qsp 100 | Qsp 100 | Qsp 100 | Qsp 100 | Qsp 100 | Qsp 100 | Qsp 100 | Qsp 100 | Qsp 100 |
| | Hydroxypropyl Starch Phosphate | 4.00 | 4.00 | 4.00 | 4.00 | 4.00 | 4.00 | 4.00 | 4.00 | 4.00 |
| | Acrylates Copolymer | 3.35 | 3.35 | 3.35 | 3.35 | 3.35 | 3.35 | 3.35 | 3.35 | 3.35 |
| | Citric Acid (and) Silver Citrate | 0.10 | 0.10 | 0.10 | 0.10 | 0.10 | 0.10 | 0.10 | 0.10 | 0.10 |
| | Sclerotium Gum | 0.10 | 0.10 | 0.10 | 0.10 | 0.10 | 0.10 | 0.10 | 0.10 | 0.10 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | | 2.00 | 2.00 | 2.00 | 2.00 | 2.00 | 2.00 | 2.00 |
| | Methylene Bis-Benzotriazolyl Tetramethylbutylphenol * | 3.00 | 3.00 | 3.00 | 3.00 | 3.00 | 3.00 | 3.00 | 3.00 | 3.00 |
| | Diethylamino Hydroxy Benzoyl Hexyl Benzoate | 4.00 | | | 4.00 | 4.00 | 4.00 | 4.00 | 4.00 | 4.00 |
| | Butyl Methoxydibenzoyl-methane | | 3.00 | | | 3.00 | | | | |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | | 2.00 | | 2.00 |
| | Methanone, 1,1'-(1,4-piperazine-diyl)bis[1-[2-[4-(diethylamino)-2-hydroxybenzoyl]phenyl]- CAS number (919803-06-8) * | | | | | | | | 2.00 | |
| | Ethylhexyl Methoxycinnamate | 7.00 | | | | | | | | 5.00 |
| | Bis-Ethylhexyloxyphenol Methoxyphenyl Triazine ** | | 2.00 | | | | | | 2.00 | |
| | Merocyanine A or B | | | 1.00 | | | | | | 0.50 |
| | In vitro SPF measured according the method described | 39.6 | 32.9 | 36 | 39.8 | 36.4 | 50.7 | 42.3 | 49.2 | 59 |
| | UVA PF measured according the method described | 15.9 | 10.9 | 13.8 | 20.1 | 17.6 | 23.2 | 22 | 24.7 | 26.2 |

| Example 12: SPRAY FORMULATION—Foaming |||||||||||
|---|---|---|---|---|---|---|---|---|---|---|
| | Sun spray foaming INCI-Name | A % w/w | B % w/w | C % w/w | D % w/w | E % w/w | F % w/w | G % w/w | H % w/w | I % w/w |
| Part A | Behenyl Alcohol (and) Glyceryl Stearate (and) Glyceryl Stearate Citrate (and) Disodium Ethylene Di(Cocamide PEG-15 Disulfate) | 0.50 | 0.50 | 0.50 | 0.50 | 0.50 | 0.50 | 0.50 | 0.50 | 0.50 |
| | Phenethyl Benzoate | 4.00 | 4.00 | 4.00 | 4.00 | 4.00 | 4.00 | 4.00 | 4.00 | 4.00 |
| | Triisodecyl Trimellitate | 2.00 | 2.00 | 2.00 | 2.00 | 2.00 | 2.00 | 2.00 | 2.00 | 2.00 |
| | Dimethyl Capramide | 1.00 | 1.00 | 1.00 | 1.00 | 1.00 | 1.00 | 1.00 | 1.00 | 1.00 |
| | Isotrideceth-12 | 0.50 | 0.50 | 0.50 | 0.50 | 0.50 | 0.50 | 0.50 | 0.50 | 0.50 |
| | Ethylhexyl Salicylate | 2.00 | 2.00 | 2.00 | 2.00 | 2.00 | 2.00 | 2.00 | 2.00 | 2.00 |
| | Hydrogenated Coco-glycerides | 1.50 | 1.50 | 1.50 | 1.50 | 1.50 | 1.50 | 1.50 | 1.50 | 1.50 |
| | C12-15 Alkyl Benzoate | 5.00 | 5.00 | 5.00 | 5.00 | 5.00 | 5.00 | 5.00 | 5.00 | 5.00 |
| Part B | Aqua | 5.00 | 5.00 | 5.00 | 5.00 | 5.00 | 5.00 | 5.00 | 5.00 | 5.00 |
| | Glycerin | 4.00 | 4.00 | 4.00 | 4.00 | 4.00 | 4.00 | 4.00 | 4.00 | 4.00 |
| | Galactoarabinan | 0.25 | 0.25 | 0.25 | 0.25 | 0.25 | 0.25 | 0.25 | 0.25 | 0.25 |
| Part C | Disodium Ethylene Di-(Cocamide PEG-15 Di-sulfate) (and) Sodium Lauroyl Lactylate | 1.00 | 1.00 | 1.00 | 1.00 | 1.00 | 1.00 | 1.00 | 1.00 | 1.00 |
| | Aqua | Qs to 100 | Qs to 100 | Qs to 100 | Qs to 100 | Qs to 100 | Qs to 100 | Qs to 100 | Qs to 100 | Qs to 100 |
| Part D | Phenoxyethanol (and) Methylparaben (and) Ethyl-paraben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.60 | 0.60 | 0.60 | 0.60 | 0.60 | 0.60 | 0.60 | 0.60 | 0.60 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | 2.00 |
| | Methylene Bis-Benzotriazolyl Tetramethylbutylphenol * | 3.00 | | | 3.00 | 3.00 | | | | |
| | Diethylamino Hydroxy Benzoyl Hexyl Benzoate | | 4.00 | | 4.00 | | 4.00 | 4.00 | | 4.00 |
| | Butyl Methoxydibenzoyl-methane | | | 3.00 | | 3.00 | | | 3.00 | 3.00 |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | | 2.00 | | |
| | Methanone, 1,1'-(1,4-piperazine-diyl)bis[1-[2-[4-(diethylamino)-2-hydroxybenzoyl]phenyl]-CAS number (919803-06-8) * | | | | | | | | 2.00 | |
| | Zinc Oxide | 4.00 | | | | | | | | |
| | Isoamyl p-Methoxycinnamate | | 3.00 | | | | | | | |
| | Polysilicone-15 | | | 5.00 | | | | | | |
| | Disodium Phenyl Dibenzylmidazole Tetrasulfonate | | | | 2.00 | | | | | |
| | Benzophenone-3 | | | | | 3.00 | | | | |
| | Terephthalylidene Di-camphor Sulfonic Acid | | | | | | 1.00 | 1.00 | 1.00 | 1.00 |
| | Drometrizole Trisiloxane | | | | | | 1.00 | 1.00 | 1.00 | 1.00 |
| | Bis-Ethylhexyloxyphenol Methoxyphenyl Triazine ** | | | | | | | | | 2.00 |
| | In vitro SPF measured according the method described | 37.6 | 33.3 | 24.2 | 25.2 | 29.7 | 32.5 | 42.4 | 28.8 | 37.3 |
| | UVA PF measured according the method described | 13.5 | 10.7 | 6.1 | 10.6 | 10 | 14.7 | 17.8 | 10.5 | 16.2 |

Example 13: SPRAY FORMULATION—Foaming

| Foameous O/W Lotion INCI-Name | | A % w/w | B % w/w | C % w/w | D % w/w | E % w/w | F % w/w | G % w/w | H % w/w | I % w/w |
|---|---|---|---|---|---|---|---|---|---|---|
| | Stearic Acid | 2.00 | 2.00 | 2.00 | 2.00 | 2.00 | 2.00 | 2.00 | 2.00 | 2.00 |
| | Phenethyl Benzoate | 2.00 | 2.00 | 2.00 | 2.00 | 2.00 | 2.00 | 2.00 | 2.00 | 2.00 |
| | Triisodecyl Trimellitate | 1.00 | 1.00 | 1.00 | 1.00 | 1.00 | 1.00 | 1.00 | 1.00 | 1.00 |
| | Dimethyl Capramide | 0.50 | 0.50 | 0.50 | 0.50 | 0.50 | 0.50 | 0.50 | 0.50 | 0.50 |
| | Cetearyl Alcohol | 2.50 | 2.50 | 2.50 | 2.50 | 2.50 | 2.50 | 2.50 | 2.50 | 2.50 |
| | PEG-30-Stearate | 3.00 | 3.00 | 3.00 | 3.00 | 3.00 | 3.00 | 3.00 | 3.00 | 3.00 |
| | Aluminium Starch Octenylisuccinate | 3.00 | 3.00 | 3.00 | 3.00 | 3.00 | 3.00 | 3.00 | 3.00 | 3.00 |
| | Talc | 0.50 | 0.50 | 0.50 | 0.50 | 0.50 | 0.50 | 0.50 | 0.50 | 0.50 |
| | Polyurethane | 0.10 | 0.10 | 0.10 | 0.10 | 0.10 | 0.10 | 0.10 | 0.10 | 0.10 |
| | Magnese silicate | 0.10 | 0.10 | 0.10 | 0.10 | 0.10 | 0.10 | 0.10 | 0.10 | 0.10 |
| | PEG-180/Octoxynol-40/TMMG Copolymer | 0.25 | 0.25 | 0.25 | 0.25 | 0.25 | 0.25 | 0.25 | 0.25 | 0.25 |
| | Cyclomethicone | 5.00 | 5.00 | 5.00 | 5.00 | 5.00 | 5.00 | 5.00 | 5.00 | 5.00 |
| | Dimethicone | 1.00 | 1.00 | 1.00 | 1.00 | 1.00 | 1.00 | 1.00 | 1.00 | 1.00 |
| | Phenyl Trimethicone | 1.00 | 1.00 | 1.00 | 1.00 | 1.00 | 1.00 | 1.00 | 1.00 | 1.00 |
| | Dimethicone/Vinyl Dimethicone Crosspolymer | 1.00 | 1.00 | 1.00 | 1.00 | 1.00 | 1.00 | 1.00 | 1.00 | 1.00 |
| | Cetyl Palmitate | 1.00 | 1.00 | 1.00 | 1.00 | 1.00 | 1.00 | 1.00 | 1.00 | 1.00 |
| | Cera Microcristallina | 1.00 | 1.00 | 1.00 | 1.00 | 1.00 | 1.00 | 1.00 | 1.00 | 1.00 |
| | Hydrated Polyisobutene | 5.00 | 5.00 | 5.00 | 5.00 | 5.00 | 5.00 | 5.00 | 5.00 | 5.00 |
| | Citric Acid | 0.10 | 0.10 | 0.10 | 0.10 | 0.10 | 0.10 | 0.10 | 0.10 | 0.10 |
| | glycerin | 5.00 | 5.00 | 5.00 | 5.00 | 5.00 | 5.00 | 5.00 | 5.00 | 5.00 |
| | Parfume, Preservatives | q.s. | q.s. | q.s. | q.s. | q.s. | q.s. | q.s. | q.s. | q.s. |
| | Sodium Hydroxide | q.s. | q.s. | q.s. | q.s. | q.s. | q.s. | q.s. | q.s. | q.s. |
| | Dyes etc. | q.s. | q.s. | q.s. | q.s. | q.s. | q.s. | q.s. | q.s. | q.s. |
| | Aqua | ad 100 | ad 100 | ad 100 | ad 100 | ad 100 | ad 100 | ad 100 | ad 100 | ad 100 |
| | pH-value adjusted to 6.0-7.5 | | | | | | | | | |
| | Propellent | Qs | Qs | Qs | Qs | Qs | Qs | Qs | Qs | Qs |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | |
| | Methylene Bis-Benzotriazolyl Tetramethylbutylphenol * | 3.00 | | | 3.00 | 3.00 | 3.00 | | | 3.00 |
| | Diethylamino Hydroxy Benzoyl Hexyl Benzoate | | 4.00 | | 4.00 | | | 4.00 | | 4.00 |
| | Butyl Methoxydibenzoyl-methane | | | 3.00 | | 3.00 | | | 3.00 | |
| | Ethylhexyl Triazone | | | | | | 2.00 | 2.00 | 2.00 | 2.00 |
| | In vitro SPF measured according the method described | 25.5 | 20.3 | 16.3 | 23.5 | 19.2 | 33 | 28.6 | 22.2 | 31.6 |
| | UVA PF measured according the method described | 10.7 | 10.6 | 6 | 15.3 | 8.8 | 10.8 | 10.6 | 6 | 15.6 |

Example 14: SPRAY FORMULATION—Continuous

| Continuous Spray sport sunscreen INCI-Name | | A % w/w | B % w/w | C % w/w | D % w/w | E % w/w | F % w/w | G % w/w | H % w/w | I % w/w |
|---|---|---|---|---|---|---|---|---|---|---|
| | SD-Alcohol 40 | 63.0 | 63.0 | 63.0 | 63.0 | 63.0 | 63.0 | 63.0 | 63.0 | 63.0 |
| | Phenethyl Benzoate | 4.00 | 4.00 | 4.00 | 4.00 | 4.00 | 4.00 | 4.00 | 4.00 | 4.00 |
| | Tridecyl Trimellitate | 2.00 | 2.00 | 2.00 | 2.00 | 2.00 | 2.00 | 2.00 | 2.00 | 2.00 |
| | Dimethyl Capramide | 1.00 | 1.00 | 1.00 | 1.00 | 1.00 | 1.00 | 1.00 | 1.00 | 1.00 |
| | Acrylates/Octylacryl-amide Copolymer | 3.00 | 3.00 | 3.00 | 3.00 | 3.00 | 3.00 | 3.00 | 3.00 | 3.00 |
| | Parfume | q.s. | q.s. | q.s. | q.s. | q.s. | q.s. | q.s. | q.s. | q.s. |
| | Propellent | Qs | Qs | Qs | Qs | Qs | Qs | Qs | Qs | Qs |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | 2.00 | 2.00 | 2.00 | | | 2.00 | 2.00 | 2.00 |
| | Methylene Bis-Benzotriazolyl Tetramethylbutylphenol * | 3.00 | 3.00 | | | 3.00 | 3.00 | 3.00 | | |

Example 14: SPRAY FORMULATION—Continued

| Continuous Spray sport sunscreen INCI-Name | A % w/w | B % w/w | C % w/w | D % w/w | E % w/w | F % w/w | G % w/w | H % w/w | I % w/w |
|---|---|---|---|---|---|---|---|---|---|
| Diethylamino Hydroxy Benzoyl Hexyl Benzoate | | | 4.00 | | 4.00 | | | 4.00 | |
| Butyl Methoxydibenzoyl-methane | 3.00 | | | 3.00 | | 3.00 | | | 3.00 |
| Ethylhexyl Triazone | 2.00 | 2.00 | 2.00 | 2.00 | 2.00 | 2.00 | 2.00 | 2.00 | 2.00 |
| Ethylhexyl Salicylate | | 5.00 | | | | | | | |
| Tris-Biphenyl Triazine * | | | 2.00 | | | | | | |
| Octocrylene | | | | 8.00 | | | | | |
| Diethylhexyl Butamido Triazone | | | | | 1.00 | | | | |
| Phenylbenzimidazole Sulfonic Acid | | | | | | 2.00 | | | |
| Titanium Dioxide *** | | | | | | | 2.00 | | |
| Homosalate | | | | | | | | 10.00 | |
| Methanone, 1,1'-(1,4-piperazine-diyl)bis[1-[2-[4-(diethylamino)-2-hydroxybenzoyl]phenyl]- CAS number (919803-06-8) * | | | | | | | | | 2.00 |
| In vitro SPF measured according the method described | 25.4 | 35.7 | 38.1 | 33.5 | 36.3 | 31.7 | 38.5 | 34.8 | 25 |
| UVA PF measured according the method described | 8.9 | 10.8 | 14.6 | 7.8 | 15.6 | 8.9 | 11.6 | 10.7 | 7.6 |

Example 15: W/O FORMULATION

| | EG-free sunscreen INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Hexyldecanol | 2.00 | 2.00 | 2.00 | 2.00 | 2.00 | 2.00 | 2.00 | 2.00 | 2.00 |
| | Polyglyceryl-3 Methyl-glucose Distearate | 1.40 | 1.40 | 1.40 | 1.40 | 1.40 | 1.40 | 1.40 | 1.40 | 1.40 |
| | Phenethyl Benzoate | 3.00 | 3.00 | 3.00 | 3.00 | 3.00 | 3.00 | 3.00 | 3.00 | 3.00 |
| | Triisodecyl Trimellitate | 1.00 | 1.00 | 1.00 | 1.00 | 1.00 | 1.00 | 1.00 | 1.00 | 1.00 |
| | Dimethyl Capramide | 0.50 | 0.50 | 0.50 | 0.50 | 0.50 | 0.50 | 0.50 | 0.50 | 0.50 |
| | Polyglyceryl-10 poly-hydroxy stearate | 1.40 | 1.40 | 1.40 | 1.40 | 1.40 | 1.40 | 1.40 | 1.40 | 1.40 |
| | Cetyl Ethylhexanoate | 2.00 | 2.00 | 2.00 | 2.00 | 2.00 | 2.00 | 2.00 | 2.00 | 2.00 |
| | Isohexadecane | 3.00 | 3.00 | 3.00 | 3.00 | 3.00 | 3.00 | 3.00 | 3.00 | 3.00 |
| | Phenoxyethanol (and) Methylparaben (and) Ethylparaben (and) Butylparaben (and) Propylparaben (and) Isobutylparaben | 0.60 | 0.60 | 0.60 | 0.60 | 0.60 | 0.60 | 0.60 | 0.60 | 0.60 |
| Part B | Aqua | Qs 100 | Qs 100 | Qs 100 | Qs 100 | Qs 100 | Qs 100 | Qs 100 | Qs 100 | Qs 100 |
| | Glycerin | 3.00 | 3.00 | 3.00 | 3.00 | 3.00 | 3.00 | 3.00 | 3.00 | 3.00 |
| Part C | Sodium Acrylates Copolymer (and) Mineral Oil (and) PPG-1 Trideceth-6 | 1.50 | 1.50 | 1.50 | 1.50 | 1.50 | 1.50 | 1.50 | 1.50 | 1.50 |
| | Cyclopentasiloxane | 1.50 | 1.50 | 1.50 | 1.50 | 1.50 | 1.50 | 1.50 | 1.50 | 1.50 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | | 2.00 | 2.00 | 2.00 | 2.00 | 2.00 | 2.00 | 2.00 |
| | Methylene Bis-Benzotriazolyl Tetramethylbutylphenol * | 3.00 | 3.00 | 3.00 | 3.00 | 3.00 | 3.00 | 3.00 | 3.00 | 3.00 |
| | Diethylamino Hydroxy Benzoyl Hexyl Benzoate | 4.00 | | | 4.00 | 4.00 | 4.00 | 4.00 | 4.00 | 4.00 |
| | Butyl Methoxydibenzoyl-methane | | 3.00 | | | 3.00 | | | | |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | 2.00 | | | 2.00 |
| | Methanone, 1,1'-(1,4-piperazine-diyl)bis[1-[2-[4-(diethylamino)-2-hydroxybenzoyl]phenyl]- CAS number (919803-06-8) * | | | | | | | 2.00 | | |
| | Ethylhexyl Methoxycinnamate | 7.00 | | | | | | | | 5.00 |

Example 15: W/O FORMULATION

| EG-free sunscreen INCI-Name | A % w/w | B % w/w | C % w/w | D % w/w | E % w/w | F % w/w | G % w/w | H % w/w | I % w/w |
|---|---|---|---|---|---|---|---|---|---|
| Bis-Ethylhexyloxyphenol Methoxyphenyl Triazine ** | | 2.00 | | | | | | 2.00 | |
| Merocyanine A or B | | | 1.00 | | | | | | 0.50 |
| In vitro SPF measured according the method described | 39.6 | 32.9 | 36 | 39.8 | 36.4 | 50.7 | 42.3 | 49.2 | 59 |
| UVA PF measured according the method described | 15.9 | 10.9 | 13.8 | 20.1 | 17.6 | 23.2 | 22 | 24.7 | 26.2 |

Example 16: Water resistant W/O emulsion

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Polyglyceryl-10 Penta-stearate (and) Behenyl Alcohol (and) Sodium Stearoyl Lactylate | 2.50 | 2.50 | 2.50 | 2.50 | 2.50 | 2.50 | 2.50 | 2.50 | 2.50 |
| | VP/Eicosene Copolymer | 1.50 | 1.50 | 1.50 | 1.50 | 1.50 | 1.50 | 1.50 | 1.50 | 1.50 |
| | Phenethyl Benzoate | 3.00 | 3.00 | 3.00 | 3.00 | 3.00 | 3.00 | 3.00 | 3.00 | 3.00 |
| | Tridecyl Trimellitate | 1.50 | 1.50 | 1.50 | 1.50 | 1.50 | 1.50 | 1.50 | 1.50 | 1.50 |
| | Dimethyl Capramide | 0.50 | 0.50 | 0.50 | 0.50 | 0.50 | 0.50 | 0.50 | 0.50 | 0.50 |
| | Stearyl Alcohol | 1.50 | 1.50 | 1.50 | 1.50 | 1.50 | 1.50 | 1.50 | 1.50 | 1.50 |
| | Squalane | 4.00 | 4.00 | 4.00 | 4.00 | 4.00 | 4.00 | 4.00 | 4.00 | 4.00 |
| | C12-15 Alkyl Benzoate | 2.50 | 2.50 | 2.50 | 2.50 | 2.50 | 2.50 | 2.50 | 2.50 | 2.50 |
| Part B | Aqua | qs to 100 | qs to 100 | qs to 100 | qs to 100 | qs to 100 | qs to 100 | qs to 100 | qs to 100 | qs to 100 |
| Part C | Glycerin | 1.80 | 1.80 | 1.80 | 1.80 | 1.80 | 1.80 | 1.80 | 1.80 | 1.80 |
| | Steareth-10 Allyl Ether/ Acrylates Copolymer | 0.80 | 0.80 | 0.80 | 0.80 | 0.80 | 0.80 | 0.80 | 0.80 | 0.80 |
| | Citric Acid (and) Silver Citrate | 0.10 | 0.10 | 0.10 | 0.10 | 0.10 | 0.10 | 0.10 | 0.10 | 0.10 |
| | Sclerotium Gum | 0.10 | 0.10 | 0.10 | 0.10 | 0.10 | 0.10 | 0.10 | 0.10 | 0.10 |
| Part D | VP/Hexadecene Copolymer | 2.70 | 2.70 | 2.70 | 2.70 | 2.70 | 2.70 | 2.70 | 2.70 | 2.70 |
| | Cyclomethicone | 1.50 | 1.50 | 1.50 | 1.50 | 1.50 | 1.50 | 1.50 | 1.50 | 1.50 |
| Part E | Aqua (and) Tocopheryl Acetate (and) Caprylic/Capric Triglyceride (and) Polysorbate 80 (and) Lecithin | 3.50 | 3.50 | 3.50 | 3.50 | 3.50 | 3.50 | 3.50 | 3.50 | 3.50 |
| | Fragrance | qs | qs | qs | qs | qs | qs | qs | qs | qs |
| | Water (and) Sodium Hydroxide | qs | qs | qs | qs | qs | qs | qs | qs | qs |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | 2.00 |
| | Methylene Bis-Benzotriazolyl Tetramethylbutylphenol * | 3.00 | | | 3.00 | 3.00 | | | | |
| | Diethylamino Hydroxy Benzoyl Hexyl Benzoate | | 4.00 | | 4.00 | | 4.00 | 4.00 | | 4.00 |
| | Butyl Methoxydibenzoyl-methane | | | 3.00 | | 3.00 | | | 3.00 | 3.00 |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | | 2.00 | | |
| | Methanone, 1,1'-(1,4-piperazine-diyl)bis[1-[2-[4-(diethylamino)-2-hydroxybenzoyl]phenyl]- CAS number (919803-06-8) * | | | | | | | | 2.00 | |
| | Zinc Oxide | 4.00 | | | | | | | | |
| | Isoamyl p-Methoxycinnamate | | 3.00 | | | | | | | |
| | Polysilicone-15 | | | 5.00 | | | | | | |
| | Disodium Phenyl Dibenzylmidazole Tetrasulfonate | | | | 2.00 | | | | | |
| | Benzophenone-3 | | | | | 3.00 | | | | |
| | Terephthalylidene Dicamphor Sulfonic Acid | | | | | | 1.00 | 1.00 | 1.00 | 1.00 |
| | Drometrizole Trisiloxane | | | | | | 1.00 | 1.00 | 1.00 | 1.00 |
| | Bis-Ethylhexyloxyphenol Methoxyphenyl Triazine ** | | | | | | | | | 2.00 |

| | Example 16: Water resistant W/O emulsion | | | | | | | | |
|---|---|---|---|---|---|---|---|---|---|
| INCI-Name | A % w/w | B % w/w | C % w/w | D % w/w | E % w/w | F % w/w | G % w/w | H % w/w | I % w/w |
| In vitro SPF measured according the method described | 37.6 | 33.3 | 24.2 | 25.2 | 29.7 | 32.5 | 42.4 | 28.8 | 37.3 |
| UVA PF measured according the method described | 13.5 | 10.7 | 6.1 | 10.6 | 10 | 14.7 | 17.8 | 10.5 | 16.2 |

| | | Example 17: Skin Protection Sunscreen W/O | | | | | | | | |
|---|---|---|---|---|---|---|---|---|---|---|
| | INCI-Name | A % w/w | B % w/w | C % w/w | D % w/w | E % w/w | F % w/w | G % w/w | H % w/w | I % w/w |
| Part A | Glyceryl Oleate | 3.00 | 3.00 | 3.00 | 3.00 | 3.00 | 3.00 | 3.00 | 3.00 | 3.00 |
| | PEG-7 Hydrogenated Castor Oil | 1.50 | 1.50 | 1.50 | 1.50 | 1.50 | 1.50 | 1.50 | 1.50 | 1.50 |
| | Phenethyl Benzoate | 4.00 | 4.00 | 4.00 | 4.00 | 4.00 | 4.00 | 4.00 | 4.00 | 4.00 |
| | Triisodecyl Trimellitate | 2.00 | 2.00 | 2.00 | 2.00 | 2.00 | 2.00 | 2.00 | 2.00 | 2.00 |
| | Dimethyl Capramide | 0.50 | 0.50 | 0.50 | 0.50 | 0.50 | 0.50 | 0.50 | 0.50 | 0.50 |
| | Hydrogenated Castor Oil | 0.50 | 0.50 | 0.50 | 0.50 | 0.50 | 0.50 | 0.50 | 0.50 | 0.50 |
| | Microcrystalline Wax | 2.00 | 2.00 | 2.00 | 2.00 | 2.00 | 2.00 | 2.00 | 2.00 | 2.00 |
| | Beeswax | 1.50 | 1.50 | 1.50 | 1.50 | 1.50 | 1.50 | 1.50 | 1.50 | 1.50 |
| | C12-15 Alkyl Benzoate | 2.00 | 2.00 | 2.00 | 2.00 | 2.00 | 2.00 | 2.00 | 2.00 | 2.00 |
| | Isopropyl Isostearate | 2.00 | 2.00 | 2.00 | 2.00 | 2.00 | 2.00 | 2.00 | 2.00 | 2.00 |
| | Mineral Oil | 5.00 | 5.00 | 5.00 | 5.00 | 5.00 | 5.00 | 5.00 | 5.00 | 5.00 |
| Part B | Aqua | qs to 100 | qs to 100 | qs to 100 | qs to 100 | qs to 100 | qs to 100 | qs to 100 | qs to 100 | qs to 100 |
| | Magnesium Sulfate | 0.50 | 0.50 | 0.50 | 0.50 | 0.50 | 0.50 | 0.50 | 0.50 | 0.50 |
| Part C | Citric Acid | 0.05 | 0.05 | 0.05 | 0.05 | 0.05 | 0.05 | 0.05 | 0.05 | 0.05 |
| | Citric Acid (and) Silver Citrate | 0.10 | 0.10 | 0.10 | 0.10 | 0.10 | 0.10 | 0.10 | 0.10 | 0.10 |
| | Sclerotium Gum | 0.10 | 0.10 | 0.10 | 0.10 | 0.10 | 0.10 | 0.10 | 0.10 | 0.10 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | |
| | Methylene Bis-Benzotriazolyl Tetramethylbutylphenol * | 3.00 | | | 3.00 | 3.00 | 3.00 | | | 3.00 |
| | Diethylamino Hydroxy Benzoyl Hexyl Benzoate | | 4.00 | | 4.00 | | | 4.00 | | 4.00 |
| | Butyl Methoxydibenzoyl-methane | | | 3.00 | | 3.00 | | | 3.00 | |
| | Ethylhexyl Triazone | | | | | | 2.00 | 2.00 | 2.00 | 2.00 |
| | In vitro SPF measured according the method described | | | | | | | | | |
| | UVA PF measured according the method described | | | | | | | | | |

| | | Example 18: W/Si FORMULATION | | | | | | | | |
|---|---|---|---|---|---|---|---|---|---|---|
| | W/Si Sun Cream INCI-Name | A % w/w | B % w/w | C % w/w | D % w/w | E % w/w | F % w/w | G % w/w | H % w/w | I % w/w |
| Part A | Bis-PEG/PPG-14/14 Dimethicone (and) Cyclopentasiloxane | 2.00 | 2.00 | 2.00 | 2.00 | 2.00 | 2.00 | 2.00 | 2.00 | 2.00 |
| | Phenethyl Benzoate | 1.50 | 1.50 | 1.50 | 1.50 | 1.50 | 1.50 | 1.50 | 1.50 | 1.50 |
| | Triisodecyl Trimellitate | 1.00 | 1.00 | 1.00 | 1.00 | 1.00 | 1.00 | 1.00 | 1.00 | 1.00 |
| | Dimethyl Capramide | 0.50 | 0.50 | 0.50 | 0.50 | 0.50 | 0.50 | 0.50 | 0.50 | 0.50 |
| | Cetyl PEG/PPG-10/1 Dimethicone | 1.70 | 1.70 | 1.70 | 1.70 | 1.70 | 1.70 | 1.70 | 1.70 | 1.70 |
| | Cyclopentasiloxane (and) Cyclohexasiloxane | 13.00 | 13.00 | 13.00 | 13.00 | 13.00 | 13.00 | 13.00 | 13.00 | 13.00 |

Example 18: W/Si FORMULATION

| | W/Si Sun Cream INCI-Name | A % w/w | B % w/w | C % w/w | D % w/w | E % w/w | F % w/w | G % w/w | H % w/w | I % w/w |
|---|---|---|---|---|---|---|---|---|---|---|
| Part B | Ethylhexyl Palmitate | 1.50 | 1.50 | 1.50 | 1.50 | 1.50 | 1.50 | 1.50 | 1.50 | 1.50 |
| | Cetyl Dimethicone | 1.00 | 1.00 | 1.00 | 1.00 | 1.00 | 1.00 | 1.00 | 1.00 | 1.00 |
| | Ethylhexyl methoxycinnamate | 3.00 | 3.00 | 3.00 | 3.00 | 3.00 | 3.00 | 3.00 | 3.00 | 3.00 |
| | Propylene Glycol | 27.00 | 27.00 | 27.00 | 27.00 | 27.00 | 27.00 | 27.00 | 27.00 | 27.00 |
| | Magnesium Sulfate Heptahydrate | 2.50 | 2.50 | 2.50 | 2.50 | 2.50 | 2.50 | 2.50 | 2.50 | 2.50 |
| | Glycerin | 26.00 | 26.00 | 26.00 | 26.00 | 26.00 | 26.00 | 26.00 | 26.00 | 26.00 |
| | Alcohol Denatured | 1.00 | 1.00 | 1.00 | 1.00 | 1.00 | 1.00 | 1.00 | 1.00 | 1.00 |
| | Aqua | Qs to 100 | Qs to 100 | Qs to 100 | Qs to 100 | Qs to 100 | Qs to 100 | Qs to 100 | Qs to 100 | Qs to 100 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | 2.00 | 2.00 | 2.00 | | | 2.00 | 2.00 | 2.00 |
| | Methylene Bis-Benzotriazolyl Tetramethylbutylphenol * | 3.00 | 3.00 | | | 3.00 | 3.00 | 3.00 | | |
| | Diethylamino Hydroxy Benzoyl Hexyl Benzoate | | | 4.00 | | 4.00 | | | 4.00 | |
| | Butyl Methoxydibenzoyl-methane | 3.00 | | | 3.00 | | 3.00 | | | 3.00 |
| | Ethylhexyl Triazone | 2.00 | 2.00 | 2.00 | 2.00 | 2.00 | 2.00 | 2.00 | 2.00 | 2.00 |
| | Ethylhexyl Salicylate | | 5.00 | | | | | | | |
| | Tris-Biphenyl Triazine * | | | 2.00 | | | | | | |
| | Octocrylene | | | | 8.00 | | | | | |
| | Diethylhexyl Butamido Triazone | | | | | 1.00 | | | | |
| | Phenylbenzimidazole Sulfonic Acid | | | | | | 2.00 | | | |
| | Titanium Dioxide *** | | | | | | | 2.00 | | |
| | Homosalate | | | | | | | | 10.00 | |
| | Methanone, 1,1'-(1,4-piperazine-diyl)bis[1-[2-[4-(diethylamino)-2-hydroxybenzoyl]phenyl]- CAS number (919803-06-8) * | | | | | | | | | 2.00 |
| | In vitro SPF measured according the method described | 25.4 | 35.7 | 38.1 | 33.5 | 36.3 | 31.7 | 38.5 | 34.8 | 25 |
| | UVA PF measured according the method described | 8.9 | 10.8 | 14.6 | 7.8 | 15.6 | 8.9 | 11.6 | 10.7 | 7.6 |

Example 19: W/Si FORMULATION

| | W/Si emulsion INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Tetrabutoxypropyl Trisiloxane | 0.90 | 0.90 | 0.90 | 0.90 | 0.90 | 0.90 | 0.90 | 0.90 | 0.90 |
| | Benzyl Laurate | 2.00 | 2.00 | 2.00 | 2.00 | 2.00 | 2.00 | 2.00 | 2.00 | 2.00 |
| | Phenethyl Benzoate | 2.00 | 2.00 | 2.00 | 2.00 | 2.00 | 2.00 | 2.00 | 2.00 | 2.00 |
| | Tridecyl Trimellitate | 1.00 | 1.00 | 1.00 | 1.00 | 1.00 | 1.00 | 1.00 | 1.00 | 1.00 |
| | Dimethyl Capramide | 0.50 | 0.50 | 0.50 | 0.50 | 0.50 | 0.50 | 0.50 | 0.50 | 0.50 |
| | Cetyl dimethicone | 2.00 | 2.00 | 2.00 | 2.00 | 2.00 | 2.00 | 2.00 | 2.00 | 2.00 |
| | Polyglyceryl-4, isostearate, cetyl dimethicone copolyol and hexyl laurate | 6.00 | 6.00 | 6.00 | 6.00 | 6.00 | 6.00 | 6.00 | 6.00 | 6.00 |
| | polyglyceryl-3 dioleate | 0.60 | 0.60 | 0.60 | 0.60 | 0.60 | 0.60 | 0.60 | 0.60 | 0.60 |
| | Glyceryl tribehenate | 3.00 | 3.00 | 3.00 | 3.00 | 3.00 | 3.00 | 3.00 | 3.00 | 3.00 |
| | cyclomethicone | 8.85 | 8.85 | 8.85 | 8.85 | 8.85 | 8.85 | 8.85 | 8.85 | 8.85 |
| Part B | Aqua | Qsp 100 | Qsp 100 | Qsp 100 | Qsp 100 | Qsp 100 | Qsp 100 | Qsp 100 | Qsp 100 | Qsp 100 |
| | Xanthan gum | 0.10 | 0.10 | 0.10 | 0.10 | 0.10 | 0.10 | 0.10 | 0.10 | 0.10 |
| | Disodium EDTA | 0.10 | 0.10 | 0.10 | 0.10 | 0.10 | 0.10 | 0.10 | 0.10 | 0.10 |
| | Sodium chloride | 1.00 | 1.00 | 1.00 | 1.00 | 1.00 | 1.00 | 1.00 | 1.00 | 1.00 |
| | Glycerin | 3.00 | 3.00 | 3.00 | 3.00 | 3.00 | 3.00 | 3.00 | 3.00 | 3.00 |

-continued

Example 19: W/Si FORMULATION

| | W/Si emulsion INCI-Name | A % w/w | B % w/w | C % w/w | D % w/w | E % w/w | F % w/w | G % w/w | H % w/w | I % w/w |
|---|---|---|---|---|---|---|---|---|---|---|
| Part C | Citric Acid (and) Silver Citrate | 0.10 | 0.10 | 0.10 | 0.10 | 0.10 | 0.10 | 0.10 | 0.10 | 0.10 |
| | Sclerotium Gum | 0.10 | 0.10 | 0.10 | 0.10 | 0.10 | 0.10 | 0.10 | 0.10 | 0.10 |
| | panthenol | 0.10 | 0.10 | 0.10 | 0.10 | 0.10 | 0.10 | 0.10 | 0.10 | 0.10 |
| | Sodium ascorbyl phosphate | 0.20 | 0.20 | 0.20 | 0.20 | 0.20 | 0.20 | 0.20 | 0.20 | 0.20 |
| | tocopheryl acetate | 0.50 | 0.50 | 0.50 | 0.50 | 0.50 | 0.50 | 0.50 | 0.50 | 0.50 |
| | Phytantriol | 0.30 | 0.30 | 0.30 | 0.30 | 0.30 | 0.30 | 0.30 | 0.30 | 0.30 |
| | Fragrance/preservative | q.s. | q.s. | q.s. | q.s. | q.s. | q.s. | q.s. | q.s. | q.s. |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | | 2.00 | 2.00 | 2.00 | 2.00 | 2.00 | 2.00 | 2.00 |
| | Methylene Bis-Benzotriazolyl Tetramethylbutylphenol * | 3.00 | 3.00 | 3.00 | 3.00 | 3.00 | 3.00 | 3.00 | 3.00 | 3.00 |
| | Diethylamino Hydroxy Benzoyl Hexyl Benzoate | 4.00 | | | 4.00 | 4.00 | 4.00 | 4.00 | 4.00 | 4.00 |
| | Butyl Methoxydibenzoyl-methane | | 3.00 | | | 3.00 | | | | |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | 2.00 | | | 2.00 |
| | Methanone, 1,1'-(1,4-piperazine-diyl)bis[1-[2-[4-(diethylamino)-2-hydroxybenzoyl]phenyl]- CAS number (919803-06-8) * | | | | | | | 2.00 | | |
| | Ethylhexyl Methoxycinnamate | 7.00 | | | | | | | | 5.00 |
| | Bis-Ethylhexyloxyphenol Methoxyphenyl Triazine ** | | 2.00 | | | | | | 2.00 | |
| | Merocyanine A or B | | | 1.00 | | | | | | 0.50 |
| | In vitro SPF measured according the method described | 39.6 | 32.9 | 36 | 39.8 | 36.4 | 50.7 | 42.3 | 49.2 | 59 |
| | UVA PF measured according the method described | 15.9 | 10.9 | 13.8 | 20.1 | 17.6 | 23.2 | 22 | 24.7 | 26.2 |

Example 20: Lipstick FORMULATION

| Lipstick Composition INCI-Name | A % w/w | B % w/w | C % w/w | D % w/w | E % w/w | F % w/w | G % w/w | H % w/w | I % w/w |
|---|---|---|---|---|---|---|---|---|---|
| Phenethyl Benzoate | 4.00 | 3.00 | 2.00 | 1.00 | 4.00 | 4.00 | 4.00 | 3.00 | 5.00 |
| Dimethyl Capramide | 1.00 | 1.00 | 1.00 | 1.00 | 0.50 | 1.00 | 2.00 | 0.50 | 0.50 |
| Isoeicosane | 8.00 | | 13.00 | | | | | | |
| Isododecane | | | | | | | | 15.00 | 15.00 |
| polyisobutene | 5.00 | | 10.00 | | | | | | |
| polybutene | | 15.00 | | | | | | | |
| Tridecyl Trimellitate | 15.00 | 15.00 | 15.00 | | | | | | |
| Diisostearate Dimerate | | | | | | | | 15.00 | 15.00 |
| Octyl palmitate | 15.00 | | 12.00 | | | | | | |
| Caprylic/Capric Triglycerides | | | | | 16.00 | 20.00 | | | |
| PEG-4 Diheptanoate | 6.00 | | | | | | | | |
| Polyglyceryl-3 Diisostearate | | | | | | | | 3.00 | 3.00 |
| Castor (Ricinus communis) oil (and) colorants | 10.00 | | | | | | | | |
| Castor (Ricinus communis) oil | | | 4.00 | 60.00 | 22.00 | 35.00 | | | |
| Trihydroxystearin | | 1.00 | | | | | | | |
| Ozokerite | | | | | 4.50 | 1.50 | | | |
| Octyldodecanol (and) Quaternium-18 Hectorite (and) Propylene carbonate | | 12.00 | | | | | | | |
| Synthetic wax | | | | | | | | 9.40 | 9.40 |
| Microcrystalline wax | | | | | 2.00 | | | | |
| Bees wax | 12.00 | | 7.00 | | | | 25.00 | | |
| Candellila wax | 5.50 | | 7.00 | 15.00 | 7.00 | 8.00 | | | |
| Carnauba wax | 10.00 | | 8.00 | 5.00 | 3.00 | 3.50 | | | |

Example 20: Lipstick FORMULATION

| | Lipstick Composition INCI-Name | A % w/w | B % w/w | C % w/w | D % w/w | E % w/w | F % w/w | G % w/w | H % w/w | I % w/w |
|---|---|---|---|---|---|---|---|---|---|---|
| | Cera Alba | | 5.00 | | | | | | | |
| | Ceresine wax | | 5.00 | | | | 5.00 | | | |
| | Tribehenin | | 12.00 | | | | | | | |
| | Octyldodecanol | | 12.00 | 10.00 | | 17.00 | | 55.00 | | |
| | polyethylene | 1.50 | | | | | | | | |
| | Calcium Aluminum Borosilicate | | | 1.00 | | | | | | |
| | Cetearyl Alcohol | | 10.00 | | | | | | | |
| | Paraffin | | | | | | | | 7.60 | 7.60 |
| | Acetylated Lanolin Alcohol | | | | 5.00 | 5.00 | 10.00 | | | |
| | Pigments/pearls | | | | | | | | 13.00 | 13.00 |
| | Colorants | | | | 12.00 | 13.00 | 13.00 | 9.50 | | |
| | Tocopherol Acetate | | 0.40 | 0.30 | | | | | 0.20 | 0.20 |
| | Preservative | | 0.10 | 0.30 | | | | | 0.10 | 0.10 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | 2.00 |
| | Methylene Bis-Benzotriazolyl Tetramethylbutylphenol * | 3.00 | | | 3.00 | 3.00 | | | | |
| | Diethylamino Hydroxy Benzoyl Hexyl Benzoate | | 4.00 | | 4.00 | | 4.00 | 4.00 | | 4.00 |
| | Butyl Methoxydibenzoyl-methane | | | 3.00 | | 3.00 | | | 3.00 | 3.00 |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | | 2.00 | | |
| | Methanone, 1,1'-(1,4-piperazine-diyl)bis[1-[2-[4-(diethylamino)-2-hydroxybenzoyl]phenyl]- CAS number (919803-06-8) * | | | | | | | | 2.00 | |
| | Zinc Oxide | 4.00 | | | | | | | | |
| | Isoamyl p-Methoxycinnamate | | 3.00 | | | | | | | |
| | Polysilicone-15 | | | 5.00 | | | | | | |
| | Disodium Phenyl Dibenzylmidazole Tetrasulfonate | | | | 2.00 | | | | | |
| | Benzophenone-3 | | | | | 3.00 | | | | |
| | Terephthalylidene Dicamphor Sulfonic Acid | | | | | | 1.00 | 1.00 | 1.00 | 1.00 |
| | Drometrizole Trisiloxane | | | | | | 1.00 | 1.00 | 1.00 | 1.00 |
| | Bis-Ethylhexyloxyphenol Methoxyphenyl Triazine ** | | | | | | | | | 2.00 |
| | In vitro SPF measured according the method described | 37.6 | 33.3 | 24.2 | 25.2 | 29.7 | 32.5 | 42.4 | 28.8 | 37.3 |
| | UVA PF measured according the method described | 13.5 | 10.7 | 6.1 | 10.6 | 10 | 14.7 | 17.8 | 10.5 | 16.2 |

Example 21: Oleogel FORMULATION

| SUNSCREEN Oleogel INCI-Name | A % w/w | B % w/w | C % w/w | D % w/w | E % w/w | F % w/w | G % w/w | H % w/w | I % w/w |
|---|---|---|---|---|---|---|---|---|---|
| Mineral Oil | Qs to 100 | Qs to 100 | Qs to 100 | Qs to 100 | Qs to 100 | Qs to 100 | Qs to 100 | Qs to 100 | Qs to 100 |
| Phenethyl Benzoate | 2.00 | 2.00 | 2.00 | 2.00 | 2.00 | 2.00 | 2.00 | 2.00 | 2.00 |
| Triisodecyl Trimellitate | 1.00 | 1.00 | 1.00 | 1.00 | 1.00 | 1.00 | 1.00 | 1.00 | 1.00 |
| Dimethyl Capramide | 0.50 | 0.50 | 0.50 | 0.50 | 0.50 | 0.50 | 0.50 | 0.50 | 0.50 |
| Polyethylene | 9.75 | 9.75 | 9.75 | 9.75 | 9.75 | 9.75 | 9.75 | 9.75 | 9.75 |
| C12-15 Alkyl Benzoate | 10.00 | 10.00 | 10.00 | 10.00 | 10.00 | 10.00 | 10.00 | 10.00 | 10.00 |
| Isopropyl Palmitate | 9.00 | 9.00 | 9.00 | 9.00 | 9.00 | 9.00 | 9.00 | 9.00 | 9.00 |
| Petrolatum | 5.25 | 5.25 | 5.25 | 5.25 | 5.25 | 5.25 | 5.25 | 5.25 | 5.25 |
| *Aleurites Moluccana* Seed Oil | 4.00 | 4.00 | 4.00 | 4.00 | 4.00 | 4.00 | 4.00 | 4.00 | 4.00 |
| Cetearyl Alcohol (and) Ceteareth-20 | 3.00 | 3.00 | 3.00 | 3.00 | 3.00 | 3.00 | 3.00 | 3.00 | 3.00 |
| *Macadamia Ternifolia* Seed Oil | 2.00 | 2.00 | 2.00 | 2.00 | 2.00 | 2.00 | 2.00 | 2.00 | 2.00 |

-continued

Example 21: Oleogel FORMULATION

| | SUNSCREEN Oleogel INCI-Name | A % w/w | B % w/w | C % w/w | D % w/w | E % w/w | F % w/w | G % w/w | H % w/w | I % w/w |
|---|---|---|---|---|---|---|---|---|---|---|
| | *Arachis Hypogaea* (Peanut) Oil | 1.00 | 1.00 | 1.00 | 1.00 | 1.00 | 1.00 | 1.00 | 1.00 | 1.00 |
| | Dimethicone | 0.95 | 0.95 | 0.95 | 0.95 | 0.95 | 0.95 | 0.95 | 0.95 | 0.95 |
| | BHT | 0.05 | 0.05 | 0.05 | 0.05 | 0.05 | 0.05 | 0.05 | 0.05 | 0.05 |
| | Fragrance | q.s. | q.s. | q.s. | q.s. | q.s. | q.s. | q.s. | q.s. | q.s. |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | |
| | Methylene Bis-Benzotriazolyl Tetramethylbutylphenol * | 3.00 | | | 3.00 | 3.00 | 3.00 | | | 3.00 |
| | Diethylamino Hydroxy Benzoyl Hexyl Benzoate | | 4.00 | | 4.00 | | | 4.00 | | 4.00 |
| | Butyl Methoxydibenzoyl-methane | | | 3.00 | | 3.00 | | | 3.00 | |
| | Ethylhexyl Triazone | | | | | | 2.00 | 2.00 | 2.00 | 2.00 |
| | In vitro SPF measured according the method described | 25.5 | 20.3 | 16.3 | 23.5 | 19.2 | 33 | 28.6 | 22.2 | 31.6 |
| | UVA PF measured according the method described | 10.7 | 10.6 | 6 | 15.3 | 8.8 | 10.8 | 10.6 | 6 | 15.6 |

Example 22: Make-up FORMULATION

| | Foundations; O/W forms INCI-Name | A % w/w | B % w/w | C % w/w | D % w/w | E % w/w | F % w/w | G % w/w | H % w/w | I % w/w |
|---|---|---|---|---|---|---|---|---|---|---|
| | Butylene Glycol | 6.50 | 6.50 | 6.50 | 6.50 | 6.50 | 6.50 | 6.50 | 6.50 | 6.50 |
| | Magnesium Aluminum Silicate | 0.50 | 0.50 | 0.50 | 0.50 | 0.50 | 0.50 | 0.50 | 0.50 | 0.50 |
| | Sodium Carboxymethyl-cellulose | 0.30 | 0.30 | 0.30 | 0.30 | 0.30 | 0.30 | 0.30 | 0.30 | 0.30 |
| | Xanthan Gum | 0.10 | 0.10 | 0.10 | 0.10 | 0.10 | 0.10 | 0.10 | 0.10 | 0.10 |
| | Triethanolamine | 1.00 | 1.00 | 1.00 | 1.00 | 1.00 | 1.00 | 1.00 | 1.00 | 1.00 |
| | Polysorbate 20 | 0.25 | 0.25 | 0.25 | 0.25 | 0.25 | 0.25 | 0.25 | 0.25 | 0.25 |
| | Sericite | 7.00 | 7.00 | 7.00 | 7.00 | 7.00 | 7.00 | 7.00 | 7.00 | 7.00 |
| | Iron oxides | 1.10 | 1.10 | 1.10 | 1.10 | 1.10 | 1.10 | 1.10 | 1.10 | 1.10 |
| | Spherical Silica | 1.00 | 1.00 | 1.00 | 1.00 | 1.00 | 1.00 | 1.00 | 1.00 | 1.00 |
| | Phenethyl Benzoate | 4.00 | 4.00 | 4.00 | 4.00 | 4.00 | 4.00 | 4.00 | 4.00 | 4.00 |
| | Tridecyl Trimellitate | 2.00 | 2.00 | 2.00 | 2.00 | 2.00 | 2.00 | 2.00 | 2.00 | 2.00 |
| | Triisodecyl Trimellitate | 2.00 | 2.00 | 2.00 | 2.00 | 2.00 | 2.00 | 2.00 | 2.00 | 2.00 |
| | Dimethyl Capramide | 1.00 | 1.00 | 1.00 | 1.00 | 1.00 | 1.00 | 1.00 | 1.00 | 1.00 |
| | Cetearyl octanoate | 10.00 | 10.00 | 10.00 | 10.00 | 10.00 | 10.00 | 10.00 | 10.00 | 10.00 |
| | Stearic Acid | 2.50 | 2.50 | 2.50 | 2.50 | 2.50 | 2.50 | 2.50 | 2.50 | 2.50 |
| | Glyceryl stearate | 2.00 | 2.00 | 2.00 | 2.00 | 2.00 | 2.00 | 2.00 | 2.00 | 2.00 |
| | Tridecyl trimellilate | 2.00 | 2.00 | 2.00 | 2.00 | 2.00 | 2.00 | 2.00 | 2.00 | 2.00 |
| | Aqua | qsp | qsp | qsp | qsp | qsp | qsp | qsp | qsp | qsp |
| | Preservative | 0.55 | 0.55 | 0.55 | 0.55 | 0.55 | 0.55 | 0.55 | 0.55 | 0.55 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | 2.00 | 2.00 | 2.00 | | | 2.00 | 2.00 | 2.00 |
| | Methylene Bis-Benzotriazolyl Tetramethylbutylphenol * | 3.00 | 3.00 | | | 3.00 | 3.00 | 3.00 | | |
| | Diethylamino Hydroxy Benzoyl Hexyl Benzoate | | | 4.00 | | 4.00 | | | 4.00 | |
| | Butyl Methoxydibenzoyl-methane | 3.00 | | | 3.00 | | 3.00 | | | 3.00 |
| | Ethylhexyl Triazone | 2.00 | 2.00 | 2.00 | 2.00 | 2.00 | 2.00 | 2.00 | 2.00 | 2.00 |
| | Ethylhexyl Salicylate | | 5.00 | | | | | | | |
| | Tris-Biphenyl Triazine * | | | 2.00 | | | | | | |
| | Octocrylene | | | | 8.00 | | | | | |
| | Diethylhexyl Butamido Triazone | | | | | 1.00 | | | | |
| | Phenylbenzimidazole Sulfonic Acid | | | | | | 2.00 | | | |

| Example 22: Make-up FORMULATION | | | | | | | | | |
|---|---|---|---|---|---|---|---|---|---|
| Foundations; O/W forms<br>INCI-Name | A<br>% w/w | B<br>% w/w | C<br>% w/w | D<br>% w/w | E<br>% w/w | F<br>% w/w | G<br>% w/w | H<br>% w/w | I<br>% w/w |
| Titanium Dioxide *** | | | | | | | 2.00 | | |
| Homosalate | | | | | | | | 10.00 | |
| Methanone, 1,1'-(1,4-piperazine-diyl)bis[1-[2-[4-(diethylamino)-2-hydroxybenzoyl]phenyl]- CAS number (919803-06-8) * | | | | | | | | | 2.00 |
| In vitro SPF measured according the method described | 25.4 | 35.7 | 38.1 | 33.5 | 36.3 | 31.7 | 38.5 | 34.8 | 25 |
| UVA PF measured according the method described | 8.9 | 10.8 | 14.6 | 7.8 | 15.6 | 8.9 | 11.6 | 10.7 | 7.6 |

| | Example 23: Cationic FORMULATION | | | | | | | | | |
|---|---|---|---|---|---|---|---|---|---|---|
| | Cationic O/W sun cream<br>INCI-Name | A<br>% w/w | B<br>% w/w | C<br>% w/w | D<br>% w/w | E<br>% w/w | F<br>% w/w | G<br>% w/w | H<br>% w/w | I<br>% w/w |
| Part A | Distearyldimonium Chloride | 3.50 | 3.50 | 3.50 | 3.50 | 3.50 | 3.50 | 3.50 | 3.50 | 3.50 |
| | Glyceryl Stearate | 1.50 | 1.50 | 1.50 | 1.50 | 1.50 | 1.50 | 1.50 | 1.50 | 1.50 |
| | Stearyl Alcohol | 1.00 | 1.00 | 1.00 | 1.00 | 1.00 | 1.00 | 1.00 | 1.00 | 1.00 |
| | Phenethyl Benzoate | 1.50 | 1.50 | 1.50 | 1.50 | 1.50 | 1.50 | 1.50 | 1.50 | 1.50 |
| | Triisodecyl Trimellitate | 1.00 | 1.00 | 1.00 | 1.00 | 1.00 | 1.00 | 1.00 | 1.00 | 1.00 |
| | Dimethyl Capramide | 0.50 | 0.50 | 0.50 | 0.50 | 0.50 | 0.50 | 0.50 | 0.50 | 0.50 |
| | C12-15 Alkyl Benzoate | 5.00 | 5.00 | 5.00 | 5.00 | 5.00 | 5.00 | 5.00 | 5.00 | 5.00 |
| | Diethylhexyl Carbonate | 3.00 | 3.00 | 3.00 | 3.00 | 3.00 | 3.00 | 3.00 | 3.00 | 3.00 |
| | Cetyl Ricinoleate | 1.00 | 1.00 | 1.00 | 1.00 | 1.00 | 1.00 | 1.00 | 1.00 | 1.00 |
| | Triisostearin | 1.00 | 1.00 | 1.00 | 1.00 | 1.00 | 1.00 | 1.00 | 1.00 | 1.00 |
| Part B | Aqua | Qs to 100 | Qs to 100 | Qs to 100 | Qs to 100 | Qs to 100 | Qs to 100 | Qs to 100 | Qs to 100 | Qs to 100 |
| | Glycerin | 3.00 | 3.00 | 3.00 | 3.00 | 3.00 | 3.00 | 3.00 | 3.00 | 3.00 |
| | Trisodium EDTA | 0.20 | 0.20 | 0.20 | 0.20 | 0.20 | 0.20 | 0.20 | 0.20 | 0.20 |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.80 | 0.80 | 0.80 | 0.80 | 0.80 | 0.80 | 0.80 | 0.80 | 0.80 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | | 2.00 | 2.00 | 2.00 | 2.00 | 2.00 | 2.00 | 2.00 |
| | Methylene Bis-Benzotriazolyl Tetramethylbutylphenol * | 3.00 | 3.00 | 3.00 | 3.00 | 3.00 | 3.00 | 3.00 | 3.00 | 3.00 |
| | Diethylamino Hydroxy Benzoyl Hexyl Benzoate | 4.00 | | | 4.00 | 4.00 | 4.00 | 4.00 | 4.00 | 4.00 |
| | Butyl Methoxydibenzoyl-methane | | 3.00 | | | 3.00 | | | | |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | 2.00 | | | 2.00 |
| | Methanone, 1,1'-(1,4-piperazine-diyl)bis[1-[2-[4-(diethylamino)-2-hydroxybenzoyl]phenyl]- CAS number (919803-06-8) * | | | | | | | 2.00 | | |
| | Ethylhexyl Methoxycinnamate | 7.00 | | | | | | | | 5.00 |
| | Bis-Ethylhexyloxyphenol Methoxyphenyl Triazine ** | | 2.00 | | | | | | 2.00 | |
| | Merocyanine A or B | | | 1.00 | | | | | | 0.50 |
| | In vitro SPF measured according the method described | 39.6 | 32.9 | 36 | 39.8 | 36.4 | 50.7 | 42.3 | 49.2 | 59 |
| | UVA PF measured according the method described | 15.9 | 10.9 | 13.8 | 20.1 | 17.6 | 23.2 | 22 | 24.7 | 26.2 |

Example 24: Cationic FORMULATION—Si/W FORMULATION

| | Si/W sun cream INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Cyclopentasiloxane (and) Dimethicone/Vinyl Dimethicone Crosspolymer | 8.00 | 8.00 | 8.00 | 8.00 | 8.00 | 8.00 | 8.00 | 8.00 | 8.00 |
| | Phenethyl Benzoate | 2.00 | 2.00 | 2.00 | 2.00 | 2.00 | 2.00 | 2.00 | 2.00 | 2.00 |
| | Triisodecyl Trimellitate | 1.00 | 1.00 | 1.00 | 1.00 | 1.00 | 1.00 | 1.00 | 1.00 | 1.00 |
| | Dimethyl Capramide | 0.50 | 0.50 | 0.50 | 0.50 | 0.50 | 0.50 | 0.50 | 0.50 | 0.50 |
| | Dimethicone (and) Dimethicone/Vinyl Dimethicone Crosspolymer | 30.00 | 30.00 | 30.00 | 30.00 | 30.00 | 30.00 | 30.00 | 30.00 | 30.00 |
| | Cyclopentasiloxane | 10.00 | 10.00 | 10.00 | 10.00 | 10.00 | 10.00 | 10.00 | 10.00 | 10.00 |
| Part B | Butylene Glycol | 3.00 | 3.00 | 3.00 | 3.00 | 3.00 | 3.00 | 3.00 | 3.00 | 3.00 |
| | Polyglyceryl-3 Disiloxane Dimethicone | 0.60 | 0.60 | 0.60 | 0.60 | 0.60 | 0.60 | 0.60 | 0.60 | 0.60 |
| | Polyglyceryl-3 Polydimethyl-siloxyethyl Dimethicone | 0.30 | 0.30 | 0.30 | 0.30 | 0.30 | 0.30 | 0.30 | 0.30 | 0.30 |
| | Acrylamide/Sodium Acryloyldimethyltaurate Co-polymer (and) Isohexadecane (and) Polysorbate 80 | 0.60 | 0.60 | 0.60 | 0.60 | 0.60 | 0.60 | 0.60 | 0.60 | 0.60 |
| | Ammonium Acryloyldimethyl-taurate/VP Copolymer | 0.65 | 0.65 | 0.65 | 0.65 | 0.65 | 0.65 | 0.65 | 0.65 | 0.65 |
| | Sodium Chloride | 0.10 | 0.10 | 0.10 | 0.10 | 0.10 | 0.10 | 0.10 | 0.10 | 0.10 |
| | Aqua | Qs to 100 | Qs to 100 | Qs to 100 | Qs to 100 | Qs to 100 | Qs to 100 | Qs to 100 | Qs to 100 | Qs to 100 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | 2.00 |
| | Methylene Bis-Benzotriazolyl Tetramethylbutylphenol * | 3.00 | | | 3.00 | 3.00 | | | | |
| | Diethylamino Hydroxy Benzoyl Hexyl Benzoate | | 4.00 | | 4.00 | | 4.00 | 4.00 | | 4.00 |
| | Butyl Methoxydibenzoyl-methane | | | 3.00 | | 3.00 | | | 3.00 | 3.00 |
| | Ethylhexyl Triazone | 2.00 | 2.00 | 2.00 | 2.00 | 2.00 | 2.00 | 2.00 | 2.00 | 2.00 |
| | Tris-Biphenyl Triazine * | | | | | | | 2.00 | | |
| | Methanone, 1,1'-(1,4-piperazine-diyl)bis[1-[2-[4-(diethylamino)-2-hydroxybenzoyl]phenyl]- CAS number (919803-06-8) * | | | | | | | | 2.00 | |
| | Zinc Oxide | 4.00 | | | | | | | | |
| | Isoamyl p-Methoxycinnamate | | 3.00 | | | | | | | |
| | Polysilicone-15 | | | 5.00 | | | | | | |
| | Disodium Phenyl Dibenzylmidazole Tetrasulfonate | | | | 2.00 | | | | | |
| | Benzophenone-3 | | | | | 3.00 | | | | |
| | Terephthalylidene Dicamphor Sulfonic Acid | | | | | | 1.00 | 1.00 | 1.00 | 1.00 |
| | Drometrizole Trisiloxane | | | | | | 1.00 | 1.00 | 1.00 | 1.00 |
| | Bis-Ethylhexyloxyphenol Methoxyphenyl Triazine ** | | | | | | | | | 2.00 |
| | In vitro SPF measured according the method described | 37.6 | 33.3 | 24.2 | 25.2 | 29.7 | 32.5 | 42.4 | 28.8 | 37.3 |
| | UVA PF measured according the method described | 13.5 | 10.7 | 6.1 | 10.6 | 10 | 14.7 | 17.8 | 10.5 | 16.2 |

Example 25: O/W FORMULATION—Anionic System emulsifier

| | Emulsion high Protection INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Cyclomethicone | 2.00 | 2.00 | 2.00 | 2.00 | 2.00 | 2.00 | 2.00 | 2.00 | 2.00 |
| | Phenethyl Benzoate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Ethylhexyl Palmitate | 3.00 | 3.00 | 3.00 | 3.00 | 3.00 | 3.00 | 3.00 | 3.00 | 3.00 |
| | Glyceryl Stearate | 1.50 | 1.50 | 1.50 | 1.50 | 1.50 | 1.50 | 1.50 | 1.50 | 1.50 |

-continued

| Example 25: O/W FORMULATION—Anionic System emulsifier | | | | | | | | | | |
|---|---|---|---|---|---|---|---|---|---|---|
| | Emulsion high Protection INCI-Name | A % w/w | B % w/w | C % w/w | D % w/w | E % w/w | F % w/w | G % w/w | H % w/w | I % w/w |
| | Potassium Cetyl Phosphate | 1.80 | 1.80 | 1.80 | 1.80 | 1.80 | 1.80 | 1.80 | 1.80 | 1.80 |
| | VP/Eicosene Copolymer | 0.60 | 0.60 | 0.60 | 0.60 | 0.60 | 0.60 | 0.60 | 0.60 | 0.60 |
| Part B | Aqua | Qs to 100 | Qs to 100 | Qs to 100 | Qs to 100 | Qs to 100 | Qs to 100 | Qs to 100 | Qs to 100 | Qs to 100 |
| | Acrylates/Palmeth-25 Acrylate Copolymer | 0.25 | 0.25 | 0.25 | 0.25 | 0.25 | 0.25 | 0.25 | 0.25 | 0.25 |
| | Glycerin | 6.00 | 6.00 | 6.00 | 6.00 | 6.00 | 6.00 | 6.00 | 6.00 | 6.00 |
| | Disodium EDTA | 0.20 | 0.20 | 0.20 | 0.20 | 0.20 | 0.20 | 0.20 | 0.20 | 0.20 |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.30 | 0.30 | 0.30 | 0.30 | 0.30 | 0.30 | 0.30 | 0.30 | 0.30 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | |
| | Methylene Bis-Benzotriazolyl Tetramethylbutylphenol * | 3.00 | | | 3.00 | 3.00 | 3.00 | | | 3.00 |
| | Diethylamino Hydroxy Benzoyl Hexyl Benzoate | | 4.00 | | 4.00 | | | 4.00 | | 4.00 |
| | Butyl Methoxydibenzoyl-methane | | | 3.00 | | 3.00 | | | 3.00 | |
| | Bis(butylbenzoate) diamino-triazine aminopropyl-siloxane (BBDAPT) | 2.0 | 4.0 | 1.0 | 1.0 | 0.5 | 1.0 | 0.5 | 1.0 | 0.5 |
| | Ethylhexyl Triazone | | | | | | 1.00 | 1.00 | | |

| Example 26: Sun Milk | | | | | | | | | | |
|---|---|---|---|---|---|---|---|---|---|---|
| | INCI-Name | A % w/w | B % w/w | C % w/w | D % w/w | E % w/w | F % w/w | G % w/w | H % w/w | I % w/w |
| Part A | C12-15 Alkyl Benzoate | 2.00 | 2.00 | 2.00 | 2.00 | 2.00 | 2.00 | 2.00 | 2.00 | 2.00 |
| | Phenethyl Benzoate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Isohexadecane | 3.00 | 3.00 | 3.00 | 3.00 | 3.00 | 3.00 | 3.00 | 3.00 | 3.00 |
| | Cyclopentasiloxane | 4.00 | 4.00 | 4.00 | 4.00 | 4.00 | 4.00 | 4.00 | 4.00 | 4.00 |
| | Stearic Acid | 0.50 | 0.50 | 0.50 | 0.50 | 0.50 | 0.50 | 0.50 | 0.50 | 0.50 |
| | PEG-100 Stearate (and) Glyceryl Stearate | 0.80 | 0.80 | 0.80 | 0.80 | 0.80 | 0.80 | 0.80 | 0.80 | 0.80 |
| | Potassium Cetyl Phosphate | 1.30 | 1.30 | 1.30 | 1.30 | 1.30 | 1.30 | 1.30 | 1.30 | 1.30 |
| | PVP/Eicosene Copolymer | 1.00 | 1.00 | 1.00 | 1.00 | 1.00 | 1.00 | 1.00 | 1.00 | 1.00 |
| Part B | Aqua | Qs to 100 | Qs to 100 | Qs to 100 | Qs to 100 | Qs to 100 | Qs to 100 | Qs to 100 | Qs to 100 | Qs to 100 |
| | Propylene Glycol | 5.00 | 5.00 | 5.00 | 5.00 | 5.00 | 5.00 | 5.00 | 5.00 | 5.00 |
| | Xanthan Gum | 0.20 | 0.20 | 0.20 | 0.20 | 0.20 | 0.20 | 0.20 | 0.20 | 0.20 |
| | Acrylates/C10-30 Alkyl Acrylate Crosspolymer | 0.15 | 0.15 | 0.15 | 0.15 | 0.15 | 0.15 | 0.15 | 0.15 | 0.15 |
| | Disodium EDTA | 0.15 | 0.15 | 0.15 | 0.15 | 0.15 | 0.15 | 0.15 | 0.15 | 0.15 |
| Part C | Triethanolamine | Qs | Qs | Qs | Qs | Qs | Qs | Qs | Qs | Qs |
| | Dimethicone | 0.40 | 0.40 | 0.40 | 0.40 | 0.40 | 0.40 | 0.40 | 0.40 | 0.40 |
| | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.90 | 0.90 | 0.90 | 0.90 | 0.90 | 0.90 | 0.90 | 0.90 | 0.90 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |

Example 26: Sun Milk

| INCI-Name | A % w/w | B % w/w | C % w/w | D % w/w | E % w/w | F % w/w | G % w/w | H % w/w | I % w/w |
|---|---|---|---|---|---|---|---|---|---|
| Bis-Ethylhexyloxyphenol Methoxyphenyl Triazine | | 2.00 | 2.00 | 2.00 | | | 2.00 | 2.00 | 2.00 |
| Methylene Bis-Benzotriazolyl Tetramethylbutylphenol * | 3.00 | 3.00 | | | 3.00 | 3.00 | 3.00 | | |
| Diethylamino Hydroxy Benzoyl Hexyl Benzoate | | | 4.00 | | 4.00 | | | 4.00 | |
| Butyl Methoxydibenzoyl-methane | 3.00 | | | 3.00 | | 3.00 | | | 3.00 |
| Bis(butylbenzoate) diamino-triazine aminopropyl-siloxane (BBDAPT) | 2.0 | 4.0 | 1.0 | 1.0 | 0.5 | 1.0 | 0.5 | 1.0 | 0.5 |
| Ethylhexyl Triazone | | | | 2.00 | 2.00 | | | | 2.00 |
| Ethylhexyl Salicylate | | 5.00 | | | | | | | |
| Tris-Biphenyl Triazine * | | | 2.00 | | | | | | |
| Octocrylene | | | | 8.00 | | | | | |
| Diethylhexyl Butamido Triazone | | | | | 1.00 | | | | |
| Phenylbenzimidazole Sulfonic Acid | | | | | | 2.00 | | | |
| Titanium Dioxide *** | | | | | | | 2.00 | | |
| Homosalate | | | | | | | | 10.00 | |
| Methanone, 1,1'-(1,4-piperazine-diyl)bis[1-[2-[4-(diethylamino)-2-hydroxybenzoyl]phenyl]- CAS number (919803-06-8) * | | | | | | | | | 2.00 |

Example 27: Every Day Lotion

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Stearyl Phosphate | 5.00 | 5.00 | 5.00 | 5.00 | 5.00 | 5.00 | 5.00 | 5.00 | 5.00 |
| | Phenethyl Benzoate | 3.00 | 3.00 | 3.00 | 3.00 | 3.00 | 3.00 | 3.00 | 3.00 | 3.00 |
| | Triisodecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Tricontanyl PVP | 1.00 | 1.00 | 1.00 | 1.00 | 1.00 | 1.00 | 1.00 | 1.00 | 1.00 |
| | Ethoxydiglycol Oleate | 1.50 | 1.50 | 1.50 | 1.50 | 1.50 | 1.50 | 1.50 | 1.50 | 1.50 |
| | Squalane | 3.00 | 3.00 | 3.00 | 3.00 | 3.00 | 3.00 | 3.00 | 3.00 | 3.00 |
| | C12-15 Alkyl Benzoate | 2.00 | 2.00 | 2.00 | 2.00 | 2.00 | 2.00 | 2.00 | 2.00 | 2.00 |
| | Glyceryl Stearate | 2.00 | 2.00 | 2.00 | 2.00 | 2.00 | 2.00 | 2.00 | 2.00 | 2.00 |
| | Cetyl Alcohol | 2.00 | 2.00 | 2.00 | 2.00 | 2.00 | 2.00 | 2.00 | 2.00 | 2.00 |
| Part B | Aqua | qs to 100 | qs to 100 | qs to 100 | qs to 100 | qs to 100 | qs to 100 | qs to 100 | qs to 100 | qs to 100 |
| | Steareth-10 Allyl Ether/Acrylates Copolymer | 0.50 | 0.50 | 0.50 | 0.50 | 0.50 | 0.50 | 0.50 | 0.50 | 0.50 |
| | Glycerin | 2.50 | 2.50 | 2.50 | 2.50 | 2.50 | 2.50 | 2.50 | 2.50 | 2.50 |
| | Diazolidinyl Urea (and) Iodopropynyl Butylcarbamate | 0.15 | 0.15 | 0.15 | 0.15 | 0.15 | 0.15 | 0.15 | 0.15 | 0.15 |
| | Sodium Lauroyl Glutamate | 0.70 | 0.70 | 0.70 | 0.70 | 0.70 | 0.70 | 0.70 | 0.70 | 0.70 |
| Part C | Cyclopentasiloxane (and) Dimethiconol | 1.50 | 1.50 | 1.50 | 1.50 | 1.50 | 1.50 | 1.50 | 1.50 | 1.50 |
| | Triethanolamine | 1.85 | 1.85 | 1.85 | 1.85 | 1.85 | 1.85 | 1.85 | 1.85 | 1.85 |
| | Citric Acid (and) Silver Citrate | 0.10 | 0.10 | 0.10 | 0.10 | 0.10 | 0.10 | 0.10 | 0.10 | 0.10 |
| | Sclerotium Gum | 0.10 | 0.10 | 0.10 | 0.10 | 0.10 | 0.10 | 0.10 | 0.10 | 0.10 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | 2.00 | 2.00 | 2.00 | 2.00 | 2.00 | 2.00 | 2.00 | 2.00 |
| | Methylene Bis-Benzotriazolyl Tetramethylbutylphenol * | 3.00 | 3.00 | 3.00 | 3.00 | 3.00 | 3.00 | 3.00 | 3.00 | 3.00 |
| | Diethylamino Hydroxy Benzoyl Hexyl Benzoate | 4.00 | | | 4.00 | 4.00 | 4.00 | 4.00 | 4.00 | 4.00 |
| | Butyl Methoxydibenzoyl-methane | | 3.00 | | | 3.00 | | | | |

Example 27: Every Day Lotion

| INCI-Name | A % w/w | B % w/w | C % w/w | D % w/w | E % w/w | F % w/w | G % w/w | H % w/w | I % w/w |
|---|---|---|---|---|---|---|---|---|---|
| Bis(butylbenzoate) diaminotriazine aminopropylsiloxane (BBDAPT) | 2.0 | 4.0 | 1.0 | 1.0 | 0.5 | 1.0 | 0.5 | 1.0 | 0.5 |
| Ethylhexyl Triazone | | | | | 2.00 | | | | 2.00 |
| Tris-Biphenyl Triazine * | | | | | | 2.00 | | | 2.00 |
| Methanone, 1,1'-(1,4-piperazine-diyl)bis[1-[2-[4-(diethylamino)-2-hydroxybenzoyl]phenyl]- CAS number (919803-06-8) * | | | | | | | 2.00 | | |
| Ethylhexyl Methoxycinnamate | 7.00 | | | | | | | | 5.00 |
| Bis-Ethylhexyloxyphenol Methoxyphenyl Triazine ** | | 2.00 | | | | | | 2.00 | |
| Merocyanine A or B | | | 1.00 | | | | | | 0.50 |

Example 28: Every Day Lotion—Nonionic System emulsifier—O/W FORMULATION

| | Sun Cream INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Tribehenin PEG-20 esters | 5.00 | 5.00 | 5.00 | 5.00 | 5.00 | 5.00 | 5.00 | 5.00 | 5.00 |
| | Phenethyl Benzoate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Dibutyl adipate | 2.00 | 2.00 | 2.00 | 2.00 | 2.00 | 2.00 | 2.00 | 2.00 | 2.00 |
| | PPG-2 Myristyl Ether Propionate | 2.00 | 2.00 | 2.00 | 2.00 | 2.00 | 2.00 | 2.00 | 2.00 | 2.00 |
| Part B | Aqua | Qs to 100 | Qs to 100 | Qs to 100 | Qs to 100 | Qs to 100 | Qs to 100 | Qs to 100 | Qs to 100 | Qs to 100 |
| | PVP/dimethylconylacrylate/polycarbamyl/polyglycol ester | 3.00 | 3.00 | 3.00 | 3.00 | 3.00 | 3.00 | 3.00 | 3.00 | 3.00 |
| | Disodium EDTA | 0.20 | 0.20 | 0.20 | 0.20 | 0.20 | 0.20 | 0.20 | 0.20 | 0.20 |
| | Sclerotium Gum | 2.00 | 2.00 | 2.00 | 2.00 | 2.00 | 2.00 | 2.00 | 2.00 | 2.00 |
| | Ammonium Acryldimethyltaurate/Beneth-25 Methacrylate Crosspolymer. | 0.50 | 0.50 | 0.50 | 0.50 | 0.50 | 0.50 | 0.50 | 0.50 | 0.50 |
| Part C | Cyclopentasiloxane (and) cyclohexasiloxane | 4.00 | 4.00 | 4.00 | 4.00 | 4.00 | 4.00 | 4.00 | 4.00 | 4.00 |
| | Phenoxyethanol (and) Methylparaben (and) Ethylparaben (and) Butylparaben (and) Propylparaben (and) Isobutylparaben | 1.00 | 1.00 | 1.00 | 1.00 | 1.00 | 1.00 | 1.00 | 1.00 | 1.00 |
| | Sodium Hydroxide (and) Aqua | Qsp | Qsp | Qsp | Qsp | Qsp | Qsp | Qsp | Qsp | Qsp |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | 2.00 |
| | Methylene Bis-Benzotriazolyl Tetramethylbutylphenol * | 3.00 | | | 3.00 | 3.00 | | | | |
| | Diethylamino Hydroxy Benzoyl Hexyl Benzoate | | 4.00 | | 4.00 | | 4.00 | 4.00 | | 4.00 |
| | Butyl Methoxydibenzoylmethane | | | 3.00 | | 3.00 | | | 3.00 | 3.00 |
| | Bis(butylbenzoate) diaminotriazine aminopropylsiloxane (BBDAPT) | 2.0 | 4.0 | 1.0 | 1.0 | 0.5 | 1.0 | 0.5 | 1.0 | 0.5 |
| | Ethylhexyl Triazone | | 2.00 | | | | | | 2.00 | 2.00 |
| | Tris-Biphenyl Triazine * | | | | | | | 2.00 | | |
| | Methanone, 1,1'-(1,4-piperazine-diyl)bis[1-[2-[4-(diethylamino)-2-hydroxybenzoyl]phenyl]- CAS number (919803-06-8) * | | | | | | | | 2.00 | |
| | Zinc Oxide | 4.00 | | | | | | | | |
| | Isoamyl p-Methoxycinnamate | | 3.00 | | | | | | | |
| | Polysilicone-15 | | | 5.00 | | | | | | |
| | Disodium Phenyl Dibenzylmidazole Tetrasulfonate | | | | 2.00 | | | | | |

Example 28: Every Day Lotion—Nonionic System emulsifier—O/W FORMULATION

| Sun Cream INCI-Name | A % w/w | B % w/w | C % w/w | D % w/w | E % w/w | F % w/w | G % w/w | H % w/w | I % w/w |
|---|---|---|---|---|---|---|---|---|---|
| Benzophenone-3 | | | | | 3.00 | | | | |
| Terephthalylidene Dicamphor Sulfonic Acid | | | | | | 1.00 | 1.00 | 1.00 | 1.00 |
| Drometrizole Trisiloxane | | | | | | 1.00 | 1.00 | 1.00 | 1.00 |
| Bis-Ethylhexyloxyphenol Methoxyphenyl Triazine ** | | | | | | | | | 2.00 |

Example 29: Every Day Lotion—Nonionic System emulsifier—O/W FORMULATION

| | UV-A/UV-B Daily Care UV Protection Lotion INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Oleth-3 Phosphate | 0.60 | 0.60 | 0.60 | 0.60 | 0.60 | 0.60 | 0.60 | 0.60 | 0.60 |
| | Steareth-21 | 2.50 | 2.50 | 2.50 | 2.50 | 2.50 | 2.50 | 2.50 | 2.50 | 2.50 |
| | Steareth-2 | 1.00 | 1.00 | 1.00 | 1.00 | 1.00 | 1.00 | 1.00 | 1.00 | 1.00 |
| | Phenethyl Benzoate | 4.00 | 4.00 | 4.00 | 4.00 | 4.00 | 4.00 | 4.00 | 4.00 | 4.00 |
| | Triisodecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Cetyl Alcohol | 0.80 | 0.80 | 0.80 | 0.80 | 0.80 | 0.80 | 0.80 | 0.80 | 0.80 |
| | Stearyl Alcohol | 1.50 | 1.50 | 1.50 | 1.50 | 1.50 | 1.50 | 1.50 | 1.50 | 1.50 |
| | Tribehenin | 0.80 | 0.80 | 0.80 | 0.80 | 0.80 | 0.80 | 0.80 | 0.80 | 0.80 |
| | Isohexadecane | 4.00 | 4.00 | 4.00 | 4.00 | 4.00 | 4.00 | 4.00 | 4.00 | 4.00 |
| Part B | Aqua | qs to 100 | qs to 100 | qs to 100 | qs to 100 | qs to 100 | qs to 100 | qs to 100 | qs to 100 | qs to 100 |
| | Glycerin | 2.00 | 2.00 | 2.00 | 2.00 | 2.00 | 2.00 | 2.00 | 2.00 | 2.00 |
| | Disodium EDTA | 0.10 | 0.10 | 0.10 | 0.10 | 0.10 | 0.10 | 0.10 | 0.10 | 0.10 |
| Part C | Aqua | 20.00 | 20.00 | 20.00 | 20.00 | 20.00 | 20.00 | 20.00 | 20.00 | 20.00 |
| | Diazolidinyl Urea (and) Iodopropynyl Butylcarbamate | 0.15 | 0.15 | 0.15 | 0.15 | 0.15 | 0.15 | 0.15 | 0.15 | 0.15 |
| | Propylene Glycol | 4.00 | 4.00 | 4.00 | 4.00 | 4.00 | 4.00 | 4.00 | 4.00 | 4.00 |
| Part D | Sodium Acrylates Copolymer (and) Paraffinium Liquidum (and) PPG-1 Trideceth-6 | 1.50 | 1.50 | 1.50 | 1.50 | 1.50 | 1.50 | 1.50 | 1.50 | 1.50 |
| | Cyclopentasiloxane | 4.00 | 4.00 | 4.00 | 4.00 | 4.00 | 4.00 | 4.00 | 4.00 | 4.00 |
| | PEG-12 Dimethicone | 2.00 | 2.00 | 2.00 | 2.00 | 2.00 | 2.00 | 2.00 | 2.00 | 2.00 |
| | Tocopheryl Acetate | 0.45 | 0.45 | 0.45 | 0.45 | 0.45 | 0.45 | 0.45 | 0.45 | 0.45 |
| | Water (and) Citric Acid | Qs | Qs | Qs | Qs | Qs | Qs | Qs | Qs | Qs |
| | Fragrance | Qs | Qs | Qs | Qs | Qs | Qs | Qs | Qs | Qs |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | |
| | Methylene Bis-Benzotriazolyl Tetramethylbutylphenol * | 3.00 | | | 3.00 | 3.00 | 3.00 | | | 3.00 |
| | Diethylamino Hydroxy Benzoyl Hexyl Benzoate | | 4.00 | | 4.00 | | | | 4.00 | 4.00 |
| | Butyl Methoxydibenzoylmethane | | | 3.00 | | 3.00 | | | 3.00 | |
| | Bis(butylbenzoate) diaminotriazine aminopropylsiloxane (BBDAPT) | 2.0 | 4.0 | 1.0 | 1.0 | 0.5 | 1.0 | 0.5 | 1.0 | 0.5 |
| | Ethylhexyl Triazone | | | | | | | 2.00 | 2.00 | 2.00 |

Example 30: Daily Care Lotion

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Polyglyceryl Methyl Glucose Distearate | 2.50 | 2.50 | 2.50 | 2.50 | 2.50 | 2.50 | 2.50 | 2.50 | 2.50 |
| | Phenethyl Benzoate | 4.00 | 4.00 | 4.00 | 4.00 | 4.00 | 4.00 | 4.00 | 4.00 | 4.00 |

Example 30: Daily Care Lotion

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| | Tridecyl Trimellitate | 3.00 | 3.00 | 3.00 | 3.00 | 3.00 | 3.00 | 3.00 | 3.00 | 3.00 |
| | Dimethyl Capramide | 1.00 | 1.00 | 1.00 | 1.00 | 1.00 | 1.00 | 1.00 | 1.00 | 1.00 |
| | Cetearyl Alcohol | 2.00 | 2.00 | 2.00 | 2.00 | 2.00 | 2.00 | 2.00 | 2.00 | 2.00 |
| | Octyl Stearate | 3.00 | 3.00 | 3.00 | 3.00 | 3.00 | 3.00 | 3.00 | 3.00 | 3.00 |
| | Caprylic/Capric Triglyceride | 1.00 | 1.00 | 1.00 | 1.00 | 1.00 | 1.00 | 1.00 | 1.00 | 1.00 |
| | Isohexadecane | 2.00 | 2.00 | 2.00 | 2.00 | 2.00 | 2.00 | 2.00 | 2.00 | 2.00 |
| Part B | Aqua | 64.80 | 64.80 | 64.80 | 64.80 | 64.80 | 64.80 | 64.80 | 64.80 | |
| | Glycerin | 5.00 | 5.00 | 5.00 | 5.00 | 5.00 | 5.00 | 5.00 | 5.00 | 5.00 |
| Part C | Phenoxyethanol (and) Methylparaben (and) Butylparaben (and) Ethylparaben (and) Propylparaben | 0.50 | 0.50 | 0.50 | 0.50 | 0.50 | 0.50 | 0.50 | 0.50 | 0.50 |
| | Cyclomethicone (and) Dimethicone | 3.00 | 3.00 | 3.00 | 3.00 | 3.00 | 3.00 | 3.00 | 3.00 | 3.00 |
| | Steareth-10 Allyl Ether/Acrylates Copolymer | 0.50 | 0.50 | 0.50 | 0.50 | 0.50 | 0.50 | 0.50 | 0.50 | 0.50 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | 2.00 | 2.00 | 2.00 | | | 2.00 | 2.00 | 2.00 |
| | Methylene Bis-Benzotriazolyl Tetramethylbutylphenol * | 3.00 | 3.00 | | | 3.00 | 3.00 | 3.00 | | |
| | Diethylamino Hydroxy Benzoyl Hexyl Benzoate | | | 4.00 | | 4.00 | | | 4.00 | |
| | Butyl Methoxydibenzoyl-methane | 3.00 | | | 3.00 | | 3.00 | | | 3.00 |
| | Bis(butylbenzoate) diamino-triazine aminopropyl-siloxane (BBDAPT) | 2.0 | 4.0 | 1.0 | 1.0 | 0.5 | 1.0 | 0.5 | 1.0 | 0.5 |
| | Ethylhexyl Triazone | 2.00 | 2.00 | | | | | | 0.50 | 2.00 |
| | Ethylhexyl Salicylate | | 5.00 | | | | | | | |
| | Tris-Biphenyl Triazine * | | | 2.00 | | | | | | |
| | Octocrylene | | | | 8.00 | | | | | |
| | Diethylhexyl Butamido Triazone | | | | | 1.00 | | | | |
| | Phenylbenzimidazole Sulfonic Acid | | | | | | 2.00 | | | |
| | Titanium Dioxide *** | | | | | | | 2.00 | | |
| | Homosalate | | | | | | | | 10.00 | |
| | Methanone, 1,1'-(1,4-piperazine-diyl)bis[1-[2-[4-(diethylamino)-2-hydroxybenzoyl]phenyl]-CAS number (919803-06-8) * | | | | | | | | | 2.00 |

Example 31: SPRAY FORMULATION—Classic

| | Sprayable Sunscreen Lotion INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Potassium Cetyl Phosphate | 0.20 | 0.20 | 0.20 | 0.20 | 0.20 | 0.20 | 0.20 | 0.20 | 0.20 |
| | Isohexadecane | 5.00 | 5.00 | 5.00 | 5.00 | 5.00 | 5.00 | 5.00 | 5.00 | 5.00 |
| | Phenethyl Benzoate | 4.00 | 4.00 | 4.00 | 4.00 | 4.00 | 4.00 | 4.00 | 4.00 | 4.00 |
| | Triisodecyl Trimellitate | 2.00 | 2.00 | 2.00 | 2.00 | 2.00 | 2.00 | 2.00 | 2.00 | 2.00 |
| | Dimethyl Capramide | 1.00 | 1.00 | 1.00 | 1.00 | 1.00 | 1.00 | 1.00 | 1.00 | 1.00 |
| | VP/Eicosene Copolymer | 1.50 | 1.50 | 1.50 | 1.50 | 1.50 | 1.50 | 1.50 | 1.50 | 1.50 |
| | Di-C12-13 Alkyl Tartrate | 4.00 | 4.00 | 4.00 | 4.00 | 4.00 | 4.00 | 4.00 | 4.00 | 4.00 |
| | C12-15 Alkyl Benzoate | 1.50 | 1.50 | 1.50 | 1.50 | 1.50 | 1.50 | 1.50 | 1.50 | 1.50 |
| Part B | Aqua | qs to 100 | qs to 100 | qs to 100 | qs to 100 | qs to 100 | qs to 100 | qs to 100 | qs to 100 | qs to 100 |
| | Sorbeth-30 | 2.00 | 2.00 | 2.00 | 2.00 | 2.00 | 2.00 | 2.00 | 2.00 | 2.00 |
| | Sorbitan Stearate (and) Sucrose Cocoate | 4.00 | 4.00 | 4.00 | 4.00 | 4.00 | 4.00 | 4.00 | 4.00 | 4.00 |
| | Aqua | 30.00 | 30.00 | 30.00 | 30.00 | 30.00 | 30.00 | 30.00 | 30.00 | 30.00 |

-continued

| | Example 31: SPRAY FORMULATION—Classic | | | | | | | | | |
|---|---|---|---|---|---|---|---|---|---|---|
| | Sprayable Sunscreen Lotion INCI-Name | A % w/w | B % w/w | C % w/w | D % w/w | E % w/w | F % w/w | G % w/w | H % w/w | I % w/w |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| Part D | Water (and) Citric Acid | qs | qs | qs | qs | qs | qs | qs | qs | qs |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | 2.00 | 2.00 | 2.00 | | | 2.00 | 2.00 | 2.00 |
| | Methylene Bis-Benzotriazolyl Tetramethylbutylphenol * | 3.00 | 3.00 | | | 3.00 | 3.00 | 3.00 | | |
| | Diethylamino Hydroxy Benzoyl Hexyl Benzoate | | | 4.00 | | 4.00 | | | 4.00 | |
| | Butyl Methoxydibenzoyl-methane | 3.00 | | | 3.00 | | 3.00 | | | 3.00 |
| | Bis(butylbenzoate) diamino-triazine aminopropyl-siloxane (BBDAPT) | 2.0 | 4.0 | 1.0 | 1.0 | 0.5 | 1.0 | 0.5 | 1.0 | 6.0 |
| | Ethylhexyl Triazone | | | | 2.00 | 2.00 | 2.00 | 2.00 | 2.00 | |
| | Ethylhexyl Salicylate | | 5.00 | | | | | | | |
| | Tris-Biphenyl Triazine * | | | 2.00 | | | | | | |
| | Octocrylene | | | | 8.00 | | | | | |
| | Diethylhexyl Butamido Triazone | | | | | 1.00 | | | | |
| | Phenylbenzimidazole Sulfonic Acid | | | | | | | 2.00 | | |
| | Titanium Dioxide *** | | | | | | | 2.00 | | |
| | Homosalate | | | | | | | | 10.00 | |
| | Methanone, 1,1'-(1,4-piperazine-diyl)bis[1-[2-[4-(diethylamino)-2-hydroxybenzoyl]phenyl]- CAS number (919803-06-8) * | | | | | | | | | 2.00 |

| | Example 32: SPRAY FORMULATION—Foaming | | | | | | | | | |
|---|---|---|---|---|---|---|---|---|---|---|
| | Foameous O/W Lotion INCI-Name | A % w/w | B % w/w | C % w/w | D % w/w | E % w/w | F % w/w | G % w/w | H % w/w | I % w/w |
| | Stearic Acid | 2.00 | 2.00 | 2.00 | 2.00 | 2.00 | 2.00 | 2.00 | 2.00 | 2.00 |
| | Phenethyl Benzoate | 2.00 | 2.00 | 2.00 | 2.00 | 2.00 | 2.00 | 2.00 | 2.00 | 2.00 |
| | Triisodecyl Trimellitate | 1.00 | 1.00 | 1.00 | 1.00 | 1.00 | 1.00 | 1.00 | 1.00 | 1.00 |
| | Dimethyl Capramide | 0.50 | 0.50 | 0.50 | 0.50 | 0.50 | 0.50 | 0.50 | 0.50 | 0.50 |
| | Cetearyl Alcohol | 2.50 | 2.50 | 2.50 | 2.50 | 2.50 | 2.50 | 2.50 | 2.50 | 2.50 |
| | PEG-30-Stearate | 3.00 | 3.00 | 3.00 | 3.00 | 3.00 | 3.00 | 3.00 | 3.00 | 3.00 |
| | Aluminium Starch Octenylisuccinate | 3.00 | 3.00 | 3.00 | 3.00 | 3.00 | 3.00 | 3.00 | 3.00 | 3.00 |
| | Talc | 0.50 | 0.50 | 0.50 | 0.50 | 0.50 | 0.50 | 0.50 | 0.50 | 0.50 |
| | Polyurethane | 0.10 | 0.10 | 0.10 | 0.10 | 0.10 | 0.10 | 0.10 | 0.10 | 0.10 |
| | Magnese silicate | 0.10 | 0.10 | 0.10 | 0.10 | 0.10 | 0.10 | 0.10 | 0.10 | 0.10 |
| | PEG-180/Octynol-40/TMMG Copolymer | 0.25 | 0.25 | 0.25 | 0.25 | 0.25 | 0.25 | 0.25 | 0.25 | 0.25 |
| | Cyclomethicone | 5.00 | 5.00 | 5.00 | 5.00 | 5.00 | 5.00 | 5.00 | 5.00 | 5.00 |
| | Dimethicone | 1.00 | 1.00 | 1.00 | 1.00 | 1.00 | 1.00 | 1.00 | 1.00 | 1.00 |
| | Phenyl Trimethicone | 1.00 | 1.00 | 1.00 | 1.00 | 1.00 | 1.00 | 1.00 | 1.00 | 1.00 |
| | Dimethicone/Vinyl Dimethicone Crosspolymer | 1.00 | 1.00 | 1.00 | 1.00 | 1.00 | 1.00 | 1.00 | 1.00 | 1.00 |
| | Cetyl Palmitate | 1.00 | 1.00 | 1.00 | 1.00 | 1.00 | 1.00 | 1.00 | 1.00 | 1.00 |
| | Cera Microcristallina | 1.00 | 1.00 | 1.00 | 1.00 | 1.00 | 1.00 | 1.00 | 1.00 | 1.00 |
| | Hydrated Polyisobutene | 5.00 | 5.00 | 5.00 | 5.00 | 5.00 | 5.00 | 5.00 | 5.00 | 5.00 |
| | Citric Acid | 0.10 | 0.10 | 0.10 | 0.10 | 0.10 | 0.10 | 0.10 | 0.10 | 0.10 |

Example 32: SPRAY FORMULATION—Foaming

| | Foameous O/W Lotion INCI-Name | A % w/w | B % w/w | C % w/w | D % w/w | E % w/w | F % w/w | G % w/w | H % w/w | I % w/w |
|---|---|---|---|---|---|---|---|---|---|---|
| | glycerin | 5.00 | 5.00 | 5.00 | 5.00 | 5.00 | 5.00 | 5.00 | 5.00 | 5.00 |
| | Parfume, Preservatives | q.s. | q.s. | q.s. | q.s. | q.s. | q.s. | q.s. | q.s. | q.s. |
| | Sodium Hydroxide | q.s. | q.s. | q.s. | q.s. | q.s. | q.s. | q.s. | q.s. | q.s. |
| | Dyes etc. | q.s. | q.s. | q.s. | q.s. | q.s. | q.s. | q.s. | q.s. | q.s. |
| | Aqua | ad 100 | ad 100 | ad 100 | ad 100 | ad 100 | ad 100 | ad 100 | ad 100 | ad 100 |
| | pH-value adjusted to 6.0-7.5 | | | | | | | | | |
| | Propellent | Qs | Qs | Qs | Qs | Qs | Qs | Qs | Qs | Qs |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 2.00 | 2.00 | 2.00 | | | 2.00 | 2.00 | 2.00 | |
| | Methylene Bis-Benzotriazolyl Tetramethylbutylphenol * | 3.00 | | | 3.00 | 3.00 | 3.00 | | | 3.00 |
| | Diethylamino Hydroxy Benzoyl Hexyl Benzoate | | 4.00 | | 4.00 | | | 4.00 | | 4.00 |
| | Butyl Methoxydibenzoyl-methane | | | 3.00 | | 3.00 | | | 3.00 | |
| | Bis(butylbenzoate) diamino-triazine aminopropyl-siloxane (BBDAPT) | 2.0 | 4.0 | 1.0 | 1.0 | 0.5 | 1.0 | 0.5 | 1.0 | 8.5 |
| | Ethylhexyl Triazone | | | | | | 2.00 | 2.00 | 2.00 | |

Example 33: W/O FORMULATION

| | EG-free sunscreen INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Hexyldecanol | 2.00 | 2.00 | 2.00 | 2.00 | 2.00 | 2.00 | 2.00 | 2.00 | 2.00 |
| | Polyglyceryl-3 Methyl-glucose Distearate | 1.40 | 1.40 | 1.40 | 1.40 | 1.40 | 1.40 | 1.40 | 1.40 | 1.40 |
| | Phenethyl Benzoate | 3.00 | 3.00 | 3.00 | 3.00 | 3.00 | 3.00 | 3.00 | 3.00 | 3.00 |
| | Triisodecyl Trimellitate | 1.00 | 1.00 | 1.00 | 1.00 | 1.00 | 1.00 | 1.00 | 1.00 | 1.00 |
| | Dimethyl Capramide | 0.50 | 0.50 | 0.50 | 0.50 | 0.50 | 0.50 | 0.50 | 0.50 | 0.50 |
| | Polyglyceryl-10 poly-hydroxy stearate | 1.40 | 1.40 | 1.40 | 1.40 | 1.40 | 1.40 | 1.40 | 1.40 | 1.40 |
| | Cetyl Ethylhexanoate | 2.00 | 2.00 | 2.00 | 2.00 | 2.00 | 2.00 | 2.00 | 2.00 | 2.00 |
| | Isohexadecane | 3.00 | 3.00 | 3.00 | 3.00 | 3.00 | 3.00 | 3.00 | 3.00 | 3.00 |
| | Phenoxyethanol (and) Methylparaben (and) Ethyl-paraben (and) Butylparaben (and) Propylparaben (and) Isobutylparaben | 0.60 | 0.60 | 0.60 | 0.60 | 0.60 | 0.60 | 0.60 | 0.60 | 0.60 |
| Part B | Aqua | Qs 100 | Qs 100 | Qs 100 | Qs 100 | Qs 100 | Qs 100 | Qs 100 | Qs 100 | Qs 100 |
| | Glycerin | 3.00 | 3.00 | 3.00 | 3.00 | 3.00 | 3.00 | 3.00 | 3.00 | 3.00 |
| Part C | Sodium Acrylates Co-polymer (and) Mineral Oil (and) PPG-1 Trideceth-6 | 1.50 | 1.50 | 1.50 | 1.50 | 1.50 | 1.50 | 1.50 | 1.50 | 1.50 |
| | Cyclopentasiloxane | 1.50 | 1.50 | 1.50 | 1.50 | 1.50 | 1.50 | 1.50 | 1.50 | 1.50 |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | | 2.00 | 2.00 | 2.00 | 2.00 | 2.00 | 2.00 | 2.00 |
| | Methylene Bis-Benzotriazolyl Tetramethylbutylphenol * | 3.00 | | 3.00 | 3.00 | 3.00 | 3.00 | 3.00 | 3.00 | 3.00 |
| | Diethylamino Hydroxy Benzoyl Hexyl Benzoate | 4.00 | | | 4.00 | 4.00 | 4.00 | 4.00 | 4.00 | 4.00 |
| | Butyl Methoxydibenzoyl-methane | | 3.00 | | | 3.00 | | | | |
| | Bis(butylbenzoate) diamino-triazine aminopropyl-siloxane (BBDAPT) | 2.0 | 4.0 | 1.0 | 1.0 | 0.5 | 1.0 | 0.5 | 1.0 | 0.5 |

Example 33: W/O FORMULATION

| EG-free sunscreen INCI-Name | A % w/w | B % w/w | C % w/w | D % w/w | E % w/w | F % w/w | G % w/w | H % w/w | I % w/w |
|---|---|---|---|---|---|---|---|---|---|
| Ethylhexyl Triazone | 2.00 | 2.00 | | | | | | 2.00 | 2.00 |
| Tris-Biphenyl Triazine * | | | | | | 2.00 | | | 2.00 |
| Methanone, 1,1'-(1,4-piperazine-diyl)bis[1-[2-[4-(diethylamino)-2-hydroxybenzoyl]phenyl]- CAS number (919803-06-8) * | | | | | | | 2.00 | | |
| Ethylhexyl Methoxycinnamate | 7.00 | | | | | | | | 5.00 |
| Bis-Ethylhexyloxyphenol Methoxyphenyl Triazine ** | | 2.00 | | | | | | 2.00 | |
| Merocyanine A or B | | | 1.00 | | | | | | 0.50 |

Example 34: W/Si FORMULATION

| | W/Si emulsion INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Tetrabutoxypropyl Trisiloxane | 0.90 | 0.90 | 0.90 | 0.90 | 0.90 | 0.90 | 0.90 | 0.90 | 0.90 |
| | Benzyl Laurate | 2.00 | 2.00 | 2.00 | 2.00 | 2.00 | 2.00 | 2.00 | 2.00 | 2.00 |
| | Phenethyl Benzoate | 2.00 | 2.00 | 2.00 | 2.00 | 2.00 | 2.00 | 2.00 | 2.00 | 2.00 |
| | Tridecyl Trimellitate | 1.00 | 1.00 | 1.00 | 1.00 | 1.00 | 1.00 | 1.00 | 1.00 | 1.00 |
| | Dimethyl Capramide | 0.50 | 0.50 | 0.50 | 0.50 | 0.50 | 0.50 | 0.50 | 0.50 | 0.50 |
| | Cetyl dimethicone | 2.00 | 2.00 | 2.00 | 2.00 | 2.00 | 2.00 | 2.00 | 2.00 | 2.00 |
| | Polyglyceryl-4, isostearate, cetyl dimethicone copolyol and hexyl laurate | 6.00 | 6.00 | 6.00 | 6.00 | 6.00 | 6.00 | 6.00 | 6.00 | 6.00 |
| | polyglyceryl-3 dioleate | 0.60 | 0.60 | 0.60 | 0.60 | 0.60 | 0.60 | 0.60 | 0.60 | 0.60 |
| | Glyceryl tribehenate | 3.00 | 3.00 | 3.00 | 3.00 | 3.00 | 3.00 | 3.00 | 3.00 | 3.00 |
| | cyclomethicone | 8.85 | 8.85 | 8.85 | 8.85 | 8.85 | 8.85 | 8.85 | 8.85 | 8.85 |
| Part B | Aqua | Qsp 100 | Qsp 100 | Qsp 100 | Qsp 100 | Qsp 100 | Qsp 100 | Qsp 100 | Qsp 100 | Qsp 100 |
| | Xanthan gum | 0.10 | 0.10 | 0.10 | 0.10 | 0.10 | 0.10 | 0.10 | 0.10 | 0.10 |
| | Disodium EDTA | 0.10 | 0.10 | 0.10 | 0.10 | 0.10 | 0.10 | 0.10 | 0.10 | 0.10 |
| | Sodium chloride | 1.00 | 1.00 | 1.00 | 1.00 | 1.00 | 1.00 | 1.00 | 1.00 | 1.00 |
| | Glycerin | 3.00 | 3.00 | 3.00 | 3.00 | 3.00 | 3.00 | 3.00 | 3.00 | 3.00 |
| Part C | Citric Acid (and) Silver Citrate | 0.10 | 0.10 | 0.10 | 0.10 | 0.10 | 0.10 | 0.10 | 0.10 | 0.10 |
| | Sclerotium Gum | 0.10 | 0.10 | 0.10 | 0.10 | 0.10 | 0.10 | 0.10 | 0.10 | 0.10 |
| | panthenol | 0.10 | 0.10 | 0.10 | 0.10 | 0.10 | 0.10 | 0.10 | 0.10 | 0.10 |
| | Sodium ascorbyl phosphate | 0.20 | 0.20 | 0.20 | 0.20 | 0.20 | 0.20 | 0.20 | 0.20 | 0.20 |
| | tocopheryl acetate | 0.50 | 0.50 | 0.50 | 0.50 | 0.50 | 0.50 | 0.50 | 0.50 | 0.50 |
| | Phytantriol | 0.30 | 0.30 | 0.30 | 0.30 | 0.30 | 0.30 | 0.30 | 0.30 | 0.30 |
| | Bis-Ethylhexyloxyphenol Methoxyphenyl Triazine) encapsulated in a polymer matrix, as described in IP.com Journal (2009), 9(1B), 17 (Tinosorb S aqua, BASF) | 4.0 | | 2.00 | | | 6.0 | | | 1.50 |
| | Fragrance/preservative | q.s. | q.s. | q.s. | q.s. | q.s. | q.s. | q.s. | q.s. | q.s. |
| Part D | MBM 1 or MBM 2 or MBM 3 or MBM 4 or MBM 5 or MBM 6 or MBM 7 or MBM 8 or MBM 9 or MBM 10 or MBM 11 or MBM 12 or MBM 13 | 10.00 | 10.00 | 10.00 | 10.00 | 10.00 | 10.00 | 10.00 | 10.00 | 10.00 |
| | Bis-Ethylhexyloxyphenol Methoxyphenyl Triazine | | | 2.00 | 2.00 | 2.00 | 2.00 | 2.00 | 2.00 | 2.00 |
| | Methylene Bis-Benzotriazolyl Tetramethylbutylphenol * | 3.00 | 3.00 | 3.00 | 3.00 | 3.00 | 3.00 | 3.00 | 3.00 | 3.00 |
| | Diethylamino Hydroxy Benzoyl Hexyl Benzoate | 4.00 | | | 4.00 | 4.00 | 4.00 | 4.00 | 4.00 | 4.00 |
| | Butyl Methoxydibenzoyl-methane | | 3.00 | | | 3.00 | | | | |
| | Bis(butylbenzoate) diamino-triazine aminopropyl-siloxane (BBDAPT) | 2.0 | 4.0 | 1.0 | 1.0 | 0.5 | 1.0 | 0.5 | 1.0 | 0.5 |

-continued

| Example 34: W/Si FORMULATION | | | | | | | | | |
|---|---|---|---|---|---|---|---|---|---|
| W/Si emulsion INCI-Name | A % w/w | B % w/w | C % w/w | D % w/w | E % w/w | F % w/w | G % w/w | H % w/w | I % w/w |
| Ethylhexyl Triazone | | | | | 2.00 | 2.00 | | | |
| Tris-Biphenyl Triazine * | | | | | | 2.00 | | | 2.00 |
| Methanone, 1,1'-(1,4-piperazine-diyl)bis[1-[2-[4-(diethylamino)-2-hydroxybenzoyl]phenyl]- CAS number (919803-06-8) * | | | | | | | 2.00 | | |
| Ethylhexyl Methoxycinnamate | 7.00 | | | | | | | | 5.00 |
| Bis-Ethylhexyloxyphenol Methoxyphenyl Triazine ** | | 2.00 | | | | | | 2.00 | |

The invention claimed is:

1. A method for protecting human and animal hair and skin against UV radiation by applying thereto a composition comprising:
   (a) a first UV filter selected from benzylidene malonate of formula

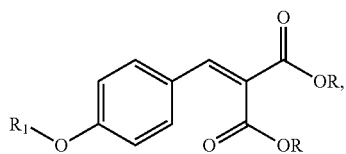

wherein
   R₁ is methyl;
   R is

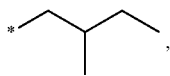 [SMILES: *CC(C)CC]

(b) at least two second UV filters selected from the group consisting of
   (b₁) Bis-Ethylhexyloxyphenol Methoxyphenyl Triazine;
   (b₃) Diethylhexyl Butamido Triazone;
   (b₄) Ethylhexyl Triazone;
   (b₅) Diethylamino Hydroxy Benzoyl Hexyl Benzoate;
   (b₆) Ethylhexyl Methoxycinnamate;
   (b₇) Ethylhexyl Salicylate;
   (b₈) Homosalate;
   (b₉) Octocrylene;
   (b₁₀) micronized Methylene Bis-Benzotriazolyl Tetramethylbutylphenol;
   (b₁₁) Phenylbenzimidazole Sulfonic Acid;
   (b₁₂) Titanium Dioxide;
   (b₁₃) micronized Tris-Biphenyl Triazine;
   (b₁₄) micronized (2-{4-[2-(4-Diethylamino-2-hydroxy-benzoyl)-benzoyl]-piperazine-1-carbonyl}-phenyl)-(4-diethylamino-2-hydroxy-phenyl)-methanone; and
   (b₁₅) Benzoic acid,4,4'-[[3-[1,3,3,3-tetramethyl-1-trimethylsilyl)oxy]-1-disiloxanyl]propyl]amino]-1,3,5-triazine-2,4-diyl]diimino]bis-, dibutyl ester;
   wherein at least one of the second UV filters is selected from component (b₅) and component (b₁₀);
   (c) cosmetically tolerable carriers or adjuvants; and
   (d) optionally one or more further UV agents selected from the group consisting of p-aminobenzoic acid derivatives, benzophenone derivatives, 3-imidazol-4-yl acrylic acid and esters; benzofuran derivatives, polymeric UV absorbers, cinnamic acid derivatives, camphor derivatives, menthyl o-aminobenzoate; and merocyanine derivatives,
   wherein the first UV filter (a), the one or more second UV filters (b), and the one or more further UV agents (d), when present, are the only UV protective agents in the composition,
   wherein the composition contains from 0.1 to 30% by weight of the UV filters (a) and (b) based on the total weight of the composition, and
   wherein the composition contains from 0.1 to 15% by weight of UV filter (a) based on the total weight of the composition.

2. The method according to claim 1, wherein the composition comprises component (b₁).

3. The method according to claim 2, wherein the composition comprises component (b₅).

4. The method according to claim 2, wherein the composition comprises component (b₁₀).

5. The method according to claim 1, wherein the composition comprises component (b₄) and/or (b₁₅).

6. The method according to claim 1, wherein the composition comprises at least three of the second UV filters selected from the group consisting of (b₁) and (b3)-(b15).

7. The method according to claim 6, wherein the composition comprises components (b₁), (b₄), and (b₁₀).

8. The method according to claim 6, wherein the composition comprises components (b₁), (b₄), and (b₅).

9. The method according to claim 1, wherein the composition comprises at least four of the second UV filters selected from the group consisting of (b₁) and (b3)-(b15).

10. The method according to claim 9, wherein the composition comprises component (b₁), component (b₄), at least one of component (b₅) and (b₁₀), and at least one of component (b₃), (b₇)-(b₉), and (b₁₁)-(b₁₅).

11. The method according to claim 9, wherein the composition comprises component (b₅), component (b₁₀), at least one of component (b₄) and (b₁₅), and at least one of component (b₃), (b₇)-(b₉), and (b₁₁)-(b₁₄).

12. The method according to claim 1,
   wherein the composition contains from 0.5 to 10% by weight of the UV filters (a) and (b) based on the total weight of the composition.

13. A method for protecting human and animal hair and skin against UV radiation by applying thereto a composition consisting of:

(a) a first UV filter selected from benzylidene malonate of formula

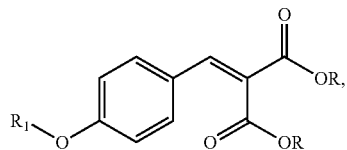
(1)

wherein
R$_1$ is methyl;
R is

, (b) at least two second UV filters selected from the group consisting of
($b_1$) Bis-Ethylhexyloxyphenol Methoxyphenyl Triazine;
($b_3$) Diethylhexyl Butamido Triazone;
($b_4$) Ethylhexyl Triazone;
($b_5$) Diethylamino Hydroxy Benzoyl Hexyl Benzoate;
($b_6$) Ethylhexyl Methoxycinnamate;
($b_7$) Ethylhexyl Salicylate;
($b_8$) Homosalate;
($b_9$) Octocrylene;
($b_{10}$) micronized Methylene Bis-Benzotriazolyl Tetramethylbutylphenol;
($b_{11}$) Phenylbenzimidazole Sulfonic Acid;
($b_{12}$) Titanium Dioxide;
($b_{13}$) micronized Tris-Biphenyl Triazine;
($b_{14}$) micronized (2-{4-[2-(4-Diethylamino-2-hydroxy-benzoyl)-benzoyl]-piperazine-1-carbonyl}-phenyl)-(4-diethylamino-2-hydroxy-phenyl)-methanone; and
($b_{15}$) Benzoic acid,4,4'-[[3-[1,3,3,3-tetramethyl-1-trimethylsilyl)oxy]-1-disiloxanyl]propyl]amino]-1,3,5-triazine-2,4-diyl]diimino]bis-, dibutyl ester;
wherein at least one of the second UV filters is selected from component ($b_5$) and component ($b_{10}$);
(c) cosmetically tolerable carriers or adjuvants selected from the group consisting of creams, gels, lotions, alcoholic solutions, aqueous/alcoholic solutions, emulsions, wax/fat compositions, stick preparations, powders, ointments, mild surfactants, super-fatting agents, pearlescent waxes, consistency regulators, thickeners, polymers, silicone compounds, fats, waxes, stabilisers, biogenic active ingredients, deodorising active ingredients, anti-dandruff agents, film formers, swelling agents, antioxidants, hydrotropic agents, preservatives, insect repellents, self-tanning agents, solubilisers, perfume oils, colourants, bacteria-inhibiting agents, and combinations thereof; and
(d) optionally one or more further UV agents selected from the group consisting of p-aminobenzoic acid derivatives, benzophenone derivatives, 3-imidazol-4-yl acrylic acid and esters;
benzofuran derivatives, polymeric UV absorbers, cinnamic acid derivatives, camphor derivatives, menthyl o-aminobenzoate; and merocyanine derivatives,
wherein the composition contains from 0.1 to 30% by weight of the UV filters (a) and (b) based on the total weight of the composition, and
wherein the composition contains from 0.1 to 15% by weight of UV filter (a) based on the total weight of the composition.

* * * * *